US012576166B2

(12) United States Patent
Pagel

(10) Patent No.: US 12,576,166 B2
(45) Date of Patent: Mar. 17, 2026

(54) CONTRAST AGENTS FOR DETECTION OF ENZYME ACTIVITIES BASED ON MELANIN SYNTHESIS

(71) Applicant: BOARD OF REGENTS, THE UNIVERSITY OF TEXAS SYSTEM, Austin, TX (US)

(72) Inventor: Mark D. Pagel, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 532 days.

(21) Appl. No.: 18/004,827

(22) PCT Filed: Jul. 26, 2021

(86) PCT No.: PCT/US2021/043172

§ 371 (c)(1),
(2) Date: Jan. 9, 2023

(87) PCT Pub. No.: WO2022/026381

PCT Pub. Date: Feb. 3, 2022

(65) Prior Publication Data

US 2023/0248849 A1 Aug. 10, 2023

Related U.S. Application Data

(60) Provisional application No. 63/057,074, filed on Jul. 27, 2020.

(51) Int. Cl.
*A61K 49/00* (2006.01)
*A61K 45/06* (2006.01)
*A61P 35/00* (2006.01)

(52) U.S. Cl.
CPC .......... *A61K 49/0056* (2013.01); *A61K 45/06* (2013.01); *A61P 35/00* (2018.01)

(58) Field of Classification Search
CPC ................ A61K 49/0056; A61K 45/06; A61K 41/0052; A61K 49/006; A61K 47/64; A61P 35/00
See application file for complete search history.

(56) References Cited

U.S. PATENT DOCUMENTS

| | | | |
|---|---|---|---|
| 3,796,723 | A | 3/1974 | Kaiser et al. |
| 6,022,526 | A | 2/2000 | Woodburn et al. |
| 7,036,516 | B1 | 5/2006 | Dees et al. |
| 7,488,749 | B2 | 2/2009 | Schraermeyer |
| 7,803,533 | B2 | 9/2010 | Nishimura et al. |
| 8,017,345 | B2 | 9/2011 | Nishimura et al. |
| 8,414,869 | B2 | 4/2013 | Perricone |
| 8,703,107 | B2 | 4/2014 | Desmurs et al. |
| 2008/0268548 | A1 | 10/2008 | Zuckerman |
| 2011/0052501 | A1 | 3/2011 | Dassa et al. |
| 2014/0356283 | A1 | 12/2014 | Cheng et al. |

FOREIGN PATENT DOCUMENTS

| | | | |
|---|---|---|---|
| AU | 2004202790 | A1 | 7/2004 |
| CA | 2745492 | A1 | 6/2010 |
| JP | 11347014 | A | 12/1999 |
| JP | 5568807 | B2 | 7/2014 |
| JP | 2018057359 | A | 4/2018 |
| KR | 20170124401 | A | 11/2017 |
| WO | 9825886 | A1 | 6/1998 |
| WO | 9855085 | A1 | 12/1998 |
| WO | 2008093323 | A2 | 8/2008 |
| WO | 2011024156 | A1 | 3/2011 |
| WO | 2011067711 | A2 | 6/2011 |

OTHER PUBLICATIONS

Cat B 680 Fast™ Fluorescent Imaging Agent, PerkinElmer, Inc., 2 pages.

Sensolyte—AFC® Urokinase (uPA) Activity Assay Kit Fluorimetic, Available Online at: https://www.anaspec.com/products/product.asp?id=51781, Mar. 2021, 6 pages.

Aggarwal et al., Cathepsin B: Multiple Roles in Cancer, Proteomics. Clinical Applications, vol. 8, No. 5-6, Jun. 2014, pp. 1-19.

Agrup et al., 5 Years' Experience of 5-S-Cysteinyldopa in Melanoma Diagnosis, Acta Dermato-Venereologica, vol. 59, No. 5, Jan. 1, 1979, pp. 381-388.

Alfieri et al., Gelatin-Based Hydrogels for the Controlled Release of 5,6-Dihydroxyindole-2-Carboxylic Acid, a Melanin-Related Metabolite with Potent Antioxidant Activity, Antioxidants, vol. 9, No. 3, Mar. 18, 2020, pp. 1-15.

Alford et al., Toxicity of Organic Fluorophores Used in Molecular Imaging: Literature Review, Molecular Imaging, vol. 8, No. 6, Nov.-Dec. 2009, pp. 341-354.

Ali et al., Tracking the Relative in Vivo Pharmacokinetics of Nanoparticles with PARACEST MRI, Molecular Pharmaceutics, vol. 6, No. 5, Sep.-Oct. 2009, 18 pages.

Antunes et al., In Vivo Evaluation of 1-o-(4-(2-Fluoroethyl-Carbamoyloxymethyl)-2-Nitrophenyl)-o-β-d-Glucopyronuronate: a Positron Emission Tomographic Tracer for Imaging B-Glucuronidase Activity in a Tumor/Inflammation Rodent Model, Molecular Imaging, vol. 11, No. 1, Feb. 2012, pp. 77-87.

(Continued)

*Primary Examiner* — Robert S Cabral

(74) *Attorney, Agent, or Firm* — Kilpatrick Townsend & Stockton LLP

(57) ABSTRACT

We disclose a composition, comprising a compound, comprising a melanin precursor that spontaneously synthesizes a melanin when in free form in vivo, and a peptide directly covalently bonded to or indirectly linked to the melanin precursor, wherein the direct covalent bond or indirect link of the peptide to the melanin precursor blocks spontaneous synthesis of the melanin in vivo in the absence of protease activity. We also disclose methods of tumor imaging, tumor detection, diagnosis, and treatment, including methods comprising administering, to a patient suffering from a tumor, the composition; and either surgically resecting the tumor or thermally ablating the tumor, wherein the surgical resection is guided at least in part by contrast imparted by, or the thermally ablating targets cells containing, the melanin, wherein the melanin is spontaneously synthesized in the tumor after administering the composition.

20 Claims, 11 Drawing Sheets

(56) References Cited

OTHER PUBLICATIONS

Asanuma et al., Sensitive β-Galactosidase-Targeting Fluorescence Probe for Visualizing Small Peritoneal Metastatic Tumours in Vivo, Nature Communications, vol. 6, Mar. 2015, pp. 1-7.
Atkinson et al., Synthesis of Acetoxy Stabilised Indolequinones as Precursors to Model Eumelanin Polymers, Synlett, vol. 2003, No. 12, Oct. 2003, pp. 1853-1855.
Attia et al., A Review of Clinical Photoacoustic Imaging: Current and Future Trends, Photoacoustics, vol. 16, Nov. 7, 2019, pp. 1-18.
Aubert et al., 5-S-Cysteinyldopa in Diagnosis and Treatment of Human Malignant Melanomas and Ultrastructural Observations, European Journal of Cancer, vol. 13, No. 11, Nov. 1, 1997, pp. 1299-1308.
Bajot et al., Reactivity and Aquatic Toxicity of Aromatic Compounds Transformable to Quinone-Type Michael Acceptors, SAR QSAR Environmental Research, vol. 22, No. 1-2, Jan. 1, 2011, pp. 51-65.
Bajou et al., Human Breast Adenocarcinoma Cell Lines Promote Angiogenesis by Providing Cells With UPA-PAI-1 and by Enhancing Their Expression, International Journal of Cancer, vol. 100, No. 5, Aug. 2002, pp. 501-506.
Banfalvi et al., Serum Levels of S-100 Protein and 5-S-Cysteinyldopa as Markers of Melanoma Progression, Pathology and Oncology Research, vol. 5, No. 3, Sep. 1, 1999, pp. 218-222.
Beard, Biomedical Photoacoustic Imaging, Interface Focus, vol. 1, No. 4, Aug. 6, 2011, pp. 602-631.
Becker et al., Multispectral Optoacoustic Tomography of the Human Breast: Characterisation of Healthy Tissue and Malignant Lesions Using a Hybrid Ultrasound-optoacoustic Approach, European Radiology, vol. 28, No. 2, Feb. 2018, pp. 602-609.
Beer et al., The Melanin Problem: A Synthesis of 5 : 6-Dihydroxyindole, Nature, vol. 161, No. 4092, Apr. 3, 1948, p. 525.
Billstrom et al., The Urokinase Inhibitor p-Aminobenzamidine Inhibits Growth of a Human Prostate Tumor in SCID Mice, International Journal of Cancer, vol. 61, May 1995, pp. 542-547.
Bishop et al., Evaluation of the Detection of Melanin by the Fontana-Masson Silver Stain in Tissue with a Wide Range of Organisms Including Cryptococcus, Human Pathology, vol. 43, No. 6, Jun. 2012, pp. 898-903.
Blencowe et al., Self-Immolative Linkers in Polymeric Delivery Systems, Polymer Chemistry, vol. 2, Nov. 2010, pp. 773-790.
Blum et al., Comparative Assessment of Substrates and Activity Based Probes as Tools for Non-invasive Optical Imaging of Cysteine Protease Activity, The Public Library of Science One, vol. 4, No. 7, Jul. 28, 2009, 10 pages.
Blum et al., Noninvasive Optical Imaging of Cysteine Protease Activity Using Fluorescently Quenched Activity-based Probes, Nature Chemical Biology, vol. 3, Sep. 9, 2007, pp. 668-677.
Boger et al., Selectively Protected L-Dopa Derivatives: Application of the Benzylic Hydroperoxide Rearrangement, The Journal of Organic Chemistry, vol. 52, Nov. 1, 1987, pp. 5283-5286.
Bourdeau et al., Acoustic Reporter Genes for Noninvasive Imaging of Microorganisms in Mammalian Hosts, Nature, vol. 553, Jan. 2018, pp. 86-90.
Brochu et al., Towards Quantitative Evaluation of Tissue Absorption Coefficients Using Light Fluence Correction in Optoacoustic Tomography, Institute of Electrical and Electronics Engineers Transactions on Medical Imaging, vol. 36, No. 1, Jan. 2017, pp. 322-331.
Brown et al., Photoacoustic Imaging as a Tool to Probe the Tumour Microenvironment, Disease Models & Mechanisms, vol. 12, No. 7, Jul. 16, 2019, pp. 1-17.
Brunker et al., Photoacoustic Imaging Using Genetically Encoded Reporters: A Review, Journal of Biomedical Optics, vol. 22, Jul. 2017, pp. 070901-1-070901-18.
Bruyne et al., Binding of Alkyl 1-Thio-β-D-Galactopyranosides to β-D-Galactosidase from *E. Coli*, Carbohydrate Research, vol. 56, No. 1, Jun. 1977, pp. 153-164.
Buck et al., Degradation of Extracellular-Matrix Proteins by Human Cathepsin B from Normal and Tumour Tissues, Biochemical Journal, vol. 282, Feb. 15, 1992, pp. 273-278.
Buehler et al., Three-Dimensional Optoacoustic Tomography at Video Rate, Optics Express, vol. 20, No. 20, Sep. 2012, pp. 22712-22719.
Burgoyne et al., Hydrogen Peroxide Sensing and Signaling by Protein Kinases in the Cardiovascular System, Antioxidants & Redox Signaling, vol. 18, No. 9, Mar. 20, 2013, pp. 1042-1052.
Caglic et al., Functional in Vivo Imaging of Cysteine Cathepsin Activity in Murine Model of Inflammation, Bioorganic & Medicinal Chemistry, vol. 19, No. 3, Feb. 1, 2011, pp. 1055-1061.
Cavallo-Medved et al., Cathepsin B: Basis Sequence: Mouse, Available online at: https://pmc.ncbi.nlm.nih.gov/articles/PMC5541861/pdf/nihms869828.pdf, Apr. 10, 2011, pp. 1-17.
Celen et al., Synthesis and Biological Evaluation of (11)c-labeled Beta-galactosyl Triazoles as Potential Pet Tracers for in Vivo LacZ Reporter Gene Imaging, Bioorganic & Medicinal Chemistry, vol. 17, No. 14, Jul. 2009, pp. 5117-5125.
Changalvaie et al., Indocyanine Green J Aggregates in Polymersomes for Near-Infrared Photoacoustic Imaging, The American Chemical Society Applied Materials & Interfaces, Dec. 5, 2019, pp. 46437-46450.
Chen et al., An Improved Synthesis of Selectively Protected L-Dopa Derivatives From L-Tyrosine, The Journal of Organic Chemistry, vol. 65, No. 8, Apr. 21, 2000, pp. 2574-2576.
Chen et al., Chemiluminescent Nanomicelles for Imaging Hydrogen Peroxide and Self-therapy in Photodynamic Therapy, BioMed Research International, vol. 2011, No. 1, 2011, pp. 1-9.
Chen et al., Evaluations of Tumor Acidosis Within in Vivo Tumor Models Using Parametric Maps Generated with Acido CEST MRI, Molecular Imaging and Biology, vol. 17, No. 4, Aug. 2015, pp. 488-496.
Chen et al., In Vivo Near-Infrared Imaging and Phototherapy of Tumors Using a Cathepsin B-Activated Fluorescent Probe, Biomaterials, vol. 122, Apr. 2017, pp. 130-140.
Chi et al., Increased Precision of Orthotopic and Metastatic Breast Cancer Surgery Guided by Matrix Metalloproteinase-activatable Nearinfrared Fluorescence Probes, Scientific Reports, vol. 5, Sep. 2015, pp. 1-10.
Cho et al., Silica-Coated Metal Chelating-Melanin Nanoparticles as a Dual-Modal Contrast Enhancement Imaging and Therapeutic Agent, The American Chemical Society Applied Materials & Interfaces, vol. 9, No. 1, Jan. 11, 2017, 23 pages.
Choe et al., Substrate Profiling of Cysteine Proteases Using a Combinatorial Peptide Library Identifies Functionally Unique Specificities, The Journal of Biological Chemistry, vol. 281, No. 18, May 5, 2006, pp. 12824-12832.
Christen et al., Molecular Imaging of Innate Immune Cell Function in Transplant Rejection, Circulation, vol. 119, No. 14, Apr. 14, 2009, pp. 1925-1932.
Cinelli et al., Identification, Synthesis, and Biological Evaluation of Metabolites of the Experimental Cancer Treatment Drugs Indotecan (LMP400) and Indimitecan (LMP776) and Investigation of Isomerically Hydroxylated Indenoisoquinoline Analogues as Topoisomerase I Pois . . , Journal of Medicinal Chemistry, vol. 55, No. 24, Dec. 27, 2012, pp. 10844-10862.
Cobb et al., N-(2-Benzoylphenyl)-L-Tyrosine PPARγ Agonists. 3. Structure-Activity Relationship and Optimization of the N-Aryl Substituent, Journal of Medicinal Chemistry, vol. 41, No. 25, Dec. 3, 1998, pp. 5055-5069.
Cox et al., Quantitative Spectroscopic Photoacoustic Imaging: A Review, Journal of Biomedical Optics, vol. 17, No. 6, Jun. 2012, pp. 061202-1-061202-12.
Cui et al., S-Gal, A Novel 1H MRI reporter for beta-Galactosidase, Magnetic Resonance in Medicine, vol. 64, No. 1, Jul. 2010, pp. 65-71.
D'Ischia et al., Pyrroles and their Benzo Derivatives: Structure, Reference Module in Chemistry, Molecular Sciences and Chemical Engineering, 2008, pp. 1-43.
Daryaei et al., A Biomarker-Responsive T2ex MRI Contrast Agent, Magnetic Resonance in Medicine, vol. 77, No. 4, Apr. 2017, 13 pages.

(56) References Cited

OTHER PUBLICATIONS

Daryaei et al., Detection of DT-Diaphorase Enzyme With a ParaCEST MRI Contrast Agent, Chemistry-A European Journal, vol. 23, May 2017, pp. 6514-6517.
Daum et al., Identification of Boronic Acid Derivatives as an Active Form of N-Alkylaminoferrocene-Based Anticancer Prodrugs and Their Radiolabeling with 18F, Bioconjugate Chemistry, vol. 30, No. 4, Feb. 15, 2019, pp. 1077-1086.
Dean-Ben et al., Advanced Optoacoustic Methods for Multiscale Imaging of in Vivo Dynamics, The Journal of Nuclear Medicine, vol. 46, No. 8, Apr. 18, 2017, pp. 2158-2198.
Dean-Ben et al., Functional Optoacoustic Imaging of Moving Objects Using Microsecond-delay Acquisition of Multispectral Three-Dimensional Tomographic Data, Scientific Reports, vol. 4, Jul. 2014, pp. 1-6.
Dewar, 626. Electrophilic Substitution. Part XII. The Nitration of Diphenylmethane, Fluorene, Diphenyl Ether, Dibenzofuran, Diphenylamine, and Carbazole; Relative Reactivities and Partial Rate Factors, Journal of the Chemical Society, 1958, pp. 3079-3084.
Dewitt et al., A Novel Imaging System Distinguishes Neoplastic from Normal Tissue During Resection of Soft Tissue Sarcomas and Mast Cell Tumors in Dogs, Veterinary Surgery : VS, vol. 45, No. 6, Aug. 2016, pp. 715-722.
Di Marzo et al., The Role of Hydrogen Peroxide in Redox-Dependent Signaling: Homeostatic and Pathological Responses in Mammalian Cells, Cells, vol. 7, No. 10, Oct. 4, 2018, p. 156.
Diot et al., Multispectral Optoacoustic Tomography (MSOT) of Human Breast Cancer, Clinical Cancer Research : an Official Journal of the American Association for Cancer Research, vol. 23, No. 22, Nov. 15, 2017, pp. 6912-6922.
Dragulescu-Andrasi et al., Activatable Oligomerizable Imaging Agents for Photoacoustic Imaging of Furin-Like Activity in Living Subjects, Journal of the American Chemical Society, vol. 135, Jul. 2013, pp. 11015-11022.
Eichberg et al., The Formal Total Synthesis of (+/−)-Strychnine via a Cobalt-Mediated [2 +2 +2]Cycloaddition, Organic Letters, vol. 2, No. 16, Aug. 1, 2000, pp. 2479-2481.
Eser et al., In Vivo Diagnosis of Murine Pancreatic Intraepithelial Neoplasia and Early-Stage Pancreatic Cancer by Molecular Imaging, Proceedings of the National Academy of Science of the USA, vol. 108, No. 24, Jun. 14, 2011, pp. 9945-9950.
Eustice et al., A Sensitive Method for the Detection of Beta-Galactosidase in Transfected Mammalian Cells, Biotechniques, vol. 11, No. 6, Dec. 1991, pp. 739-740.
Eward et al., A Novel Imaging System Permits Real-time in Vivo Tumor Bed Assessment After Resection of Naturally Occurring Sarcomas in Dogs, Clinical Orthopaedics and Related Research, vol. 471, No. 3, Mar. 2013, pp. 834-842.
Falguera et al., A Kinetic Model Describing Melanin Formation by Means of Mushroom Tyrosinase, Food Research International, vol. 43, No. 1, Jan. 2010, pp. 66-69.
Fan et al., Photoacoustic-imagingguided Therapy of Functionalized Melanin Nanoparticles: Combination of Photothermal Ablation and Gene Therapy Against Laryngeal Squamous Cell Carcinoma, Nanoscale, vol. 11, No. 13, May 28, 2019, pp. 6285-6296.
Fan et al., Transferring Biomarker into Molecular Probe: Melanin Nanoparticle as a Naturally Active Platform for Multimodality Imaging, Journal of the American Chemical Society, vol. 136, No. 43, Oct. 2014, pp. 15185-15194.
Farnleitner et al., Hydrolysis of 4-Methylumbelliferyl-beta-D-glucuronidase in Differing Sample Fractions of River Waters and Its Implication for the Detection of Fecal Pollution, Water Research, vol. 36, No. 4, Feb. 2002, pp. 975-981.
Fehm et al., In Vivo Whole-Body Optoacoustic Scanner With Real-Time Volumetric Imaging Capacity, Optica, vol. 3, No. 11, Nov. 2016, pp. 1153-1159.
Feng et al., TYR as a Multifunctional Reporter Gene Regulated by the Tet-on System for Multimodality Imaging: an in Vitro Study, Scientific Reports, vol. 5, Oct. 20, 2015, 10 pages.
Fernandez-Cuervo et al., A CatalyCEST MRI Contrast Agent that Can Simultaneously Detect Two Enzyme Activities, Chembiochem, vol. 17, No. 5, Mar. 2, 2016, pp. 383-387.
Fernández-Cuervo et al., Diamagnetic Imaging Agents with a Modular Chemical Design for Quantitative Detection of B-Galactosidase and B-Glucuronidase Activities with CatalyCEST MRI, Bioconjugate Chemistry, vol. 27, No. 10, Sep. 2016, pp. 2549-2557.
Flurkey et al., Use of Mushroom Tyrosinase to Introduce Michaelis-Menten Enzyme Kinetics to Biochemistry Students, Biochemistry and Molecular Biology Education, vol. 45, May 2017, pp. 270-276.
Fu et al., Photoacoustic Imaging: Contrast Agents and Their Biomedical Applications, Advanced Materials, vol. 31, No. 6, Feb. 2019, pp. 1-31.
Fujii et al., In Vivo Imaging of Intraperitoneally Disseminated Tumors in Model Mice by Using Activatable Fluorescent Small-Molecular Probes for Activity of Cathepsins, Bioconjugate Chemistry, vol. 25, No. 10, Oct. 15, 2014, pp. 1838-1846.
Garcia-Allende et al., Enriching the Interventional Vision of Cancer with Fluorescence and Optoacoustic Imaging, Journal of Nuclear Medicine, vol. 54, No. 5, May 1, 2013, pp. 664-667.
Gosalia et al., Profiling Serine Protease Substrate Specificity With Solution Phase Fluorogenic Peptide Microarrays, Proteomics, vol. 5, No. 5, Apr. 2005, pp. 1292-1298.
Goto et al., 5-S-Cysteinyldopa as Diagnostic Tumor Marker for Uveal Malignant Melanoma, Japanese Journal of Ophthalmology, vol. 45, No. 5, Sep. 1, 2001, pp. 538-542.
Gounaris et al., Live Imaging of Cysteine-Cathepsin Activity Reveals Dynamics of Focal Inflammation, Angiogenesis, and Polyp Growth, The Public Library of Science, vol. 3, No. 8, Aug. 13, 2008, pp. 1-9.
Grootendorst et al., First Experiences of Photoacoustic Imaging for Detection of Melanoma Metastases in Resected Human Lymph Nodes, Lasers in Surgery and Medicine, vol. 44, No. 7, Sep. 2012, pp. 541-549.
Hagen et al., Aminoferrocene-Based Prodrugs Activated by Reactive Oxygen Species, Journal of Medicinal Chemistry, vol. 55, No. 2, 2012, pp. 924-934.
Hall et al., Expression and Regulation of *Escherichia coli* Lacz Gene Fusions in Mammalian Cells, Journal of Molecular and Applied Genetics, vol. 1, No. 2, Jan. 1983, pp. 101-109.
Hara et al., High Plasma Level of a Eumelanin Precursor, 6-Hydroxy-5-Methoxyindole-2-Carboxylic Acid as a Prognostic Marker for Malignant Melanoma, Journal of Investigative Dermatology, vol. 102, No. 4, Apr. 1, 1994, pp. 501-505.
Haris et al., In Vivo Magnetic Resonance Imaging of Tumor Protease Activity, Scientific Reports, vol. 4, Aug. 15, 2014, pp. 1-5.
Harris et al., Rapid and General Profiling of Protease Specificity by Using Combinatorial Fluorogenic Substrate Libraries, Proceedings of the National Academy of Sciences of the United States of America, vol. 97, No. 14, Jul. 5, 2000, pp. 7754-7759.
He et al., Combination of Fluorescence-Guided Surgery With Photodynamic Therapy for the Treatment of Cancer, Molecular Imaging, vol. 16, Aug. 29, 2017, 15 pages.
He et al., Improved Protocol for Indoline Synthesis via Palladium-Catalyzed Intramolecular C(sp2)-H Amination, Organic Letters, vol. 14, No. 12, Jun. 6, 2012, pp. 2944-2947.
Hingorani et al., A CatalyCEST MRI Contrast Agent That Detects the Enzymecatalyzed Creation of a Covalent Bond, Journal of the American Chemical Society, vol. 135, No. 17, May 1, 2013, 9 pages.
Hingorani et al., A Single Diamagnetic CatalyCEST MRI Contrast Agent That Detects Cathepsin B Enzyme Activity by Using a Ratio of Two CEST Signals, Contrast Media & Molecular Imaging, vol. 11, No. 2, Mar. 2016, pp. 130-138.
Hingorani et al., Early Detection of Squamous Cell Carcinoma in Carcinogen Induced Oral Cancer Rodent Model by Ratiometric Activatable Cell Penetrating Peptides, Oral Oncology, vol. 71, Aug. 2017, 15 pages.
Hirasawa et al., Multispectral Photoacouostic Imaging of Tumours in Mice Injected With an Enzyme-activatable Photoacoustic Probe, Journal of Optics, vol. 19, No. 1, Jan. 2017, pp. 1-14.
Horikoshi et al., Evaluation of Melanin-Related Metabolites as Markers of Melanoma Progression, Cancer, vol. 73, No. 3, Feb. 1, 1994, pp. 629-636.

(56) References Cited

OTHER PUBLICATIONS

Hu et al., In Vivo Imaging of Mouse Tumors by a Lipidated Cathepsin S Substrate, Angewandte Chemie international edition, vol. 53, Jul. 2014, pp. 7669-7673.
Huber et al., uPAR Enhances Malignant Potential of Triple-Negative Breast Cancer by Directly Interacting with uPA and IGF1R, Brihanmumbai Municipal Corporation Cancer, vol. 16, Aug. 8, 2016, pp. 1-12.
Hupple et al., A Light-fluenceindependent Method for the Quantitative Analysis of Dynamic Contrast-enhanced Multispectral Optoacoustic Tomography (DCE MSOT), Photoacoustics, vol. 10, May 2018, pp. 54-64.
Hussain et al., Surgical Molecular Navigation With Ratiometric Activatable Cell Penetrating Peptide for Intraoperative Identification and Resection of Small Salivary Gland Cancers, Head & Neck, vol. 38, No. 5, May 2016, pp. 715-723.
Illy et al., Role of the Occluding Loop in Cathepsin B Activity, The Journal of Biological Chemistry, vol. 272, No. 2, Jan. 10, 1997, pp. 1197-1202.
Ito et al., Synthesis and Antitumor Activity of Cysteinyl-3,4-Dihydroxyphenylalanines and Related Compounds, Journal of Medicinal Chemistry, vol. 24, No. 6, Jun. 1981, pp. 673-677.
Jathoul et al., Deep in Vivo Photoacoustic Imaging of Mammalian Tissues Using a Tyrosine-based Genetic Reporter, Nature Photonics, vol. 9, Mar. 2015, pp. 239-246.
Jefferson et al., Beta-Glucuronidase From *Escherichia coli* as a Gene-Fusion Marker, Proceedings of the National Academy of Sciences of the United States of America, vol. 83, No. 22, Nov. 1986, pp. 8447-8451.
Jimbow et al., Exploitation of Pigment Biosynthesis Pathway as a Selective Chemotherapeutic Approach for Malignant Melanoma, Journal of Investigative Dermatology, vol. 100, No. 2, Feb. 1993, pp. 231S-238S.
Jo et al., Molecular Imaging of Proteolytic Activity in Cancer, Journal of Cellular Biochemistry, vol. 90, No. 6, Dec. 1, 2003, pp. 1087-1097.
Jones et al., Linearization Improves the Repeatability of Quantitative Dynamic Contrast Enhanced MRI, Magnetic Resonance Imaging, vol. 47, Apr. 2018, pp. 16-24.
Joyce et al., Cathepsin Cysteine Proteases are Effectors of Invasive Growth and Angiogenesis During Multistage Tumorigenesis, Cancer Cell, vol. 5, No. 5, May 2004, pp. 443-453.
Ju et al., pH-Induced Aggregated Melanin Nanoparticles for Photoacoustic Signal Amplification, Nanoscale, vol. 8, No. 30, Aug. 14, 2016, pp. 14448-14456.
Kanematsu et al., Definitive Diagnosis of Early Malignant Melanoma Lesions by the Quantitative Analysis of 5-S-cysteinyldopa in the Tissue and Touch Fluorescence Method, The Japanese Journal of Dermatology, vol. 99, No. 7, May 31, 1989, pp. 783-791.
Karnell et al., S100B Protein, 5-S-Cysteinyldopa and 6-Hydroxy-5-Methoxyindole-2-Carboxylic Acid as Biochemical Markers for Survival Prognosis in Patients with Malignant Melanoma, Melanoma Research, vol. 7, No. 5, Oct. 1997, pp. 393-399.
Kato et al., Covalent Adduction of Endogenous and Food-Derived Quinones to a Protein: Its Biological Significance, Journal of Clinical Biochemistry and Nutrition, vol. 62, No. 3, May 1, 2018, pp. 213-220.
Kendall et al., Synthetic Route to an Aromatic Analog of Strigol, The Journal of Organic Chemistry, vol. 44, No. 9, Jan. 1, 1979, pp. 1421-1424.
Ketuly et al., Boronate Derivatives of Functionally Diverse Catechols: Stability Studies, Molecules, vol. 15, No. 4, Mar. 31, 1010, pp. 2347-2356.
Khersonsky et al., Enzyme Promiscuity: a Mechanistic and Evolutionary Perspective, Annual Review of Biochemistry, vol. 79, Mar. 2010, pp. 471-505.
Kim et al., Natural Melanin-Loaded Nanovesicles for Near-Infrared Mediated Tumor Ablation by Photothermal Conversion, vol. 29, No. 41, Nanotechnology, Aug. 2, 2018, pp. 1-10.
Kisin-Finfer et al., Synthesis and Evaluation of New NIR-Fluorescent Probes for Cathepsin B: ICT Versus FRET as a Turn-ON Mode-of-Action, Bioorganic & Medicinal Chemistry Letters, vol. 24, No. 11, Jun. 1, 2014, pp. 2453-2458.
Knieling et al., Multispectral Optoacoustic Tomography for Assessment of Crohn's Disease Activity, The New England Journal of Medicine, vol. 376, Mar. 30, 2017, 3 pages.
Kobes et al., Improved Treatment of Pancreatic Cancer with Drug Delivery Nanoparticles Loaded with a Novel AKT/PDK1 Inhibitor, Pancreas, vol. 45, No. 8, Sep. 2016, pp. 1-21.
Kodibagkar et al., Imaging Beta-Galactosidase Activity Using 19F Chemical Shift Imaging of LacZ Gene-Reporter Molecule 2-Fluoro-4-Nitrophenol-Beta-D-Galactopyranoside, Magnetic Resonance Imaging, vol. 24, Sep. 2006, pp. 959-962.
Krumholz et al., Photoacoustic Microcopy of Tyrosinase Reporter Gene in Vivo, Journal of Biomedical Optics, vol. 16, No. 8, Aug. 2011, pp. 080503-1-080503-3.
Lai et al., Early Diagnosis of Osteoarthritis Using Cathepsin B Sensitive Near-Infrared Fluorescent Probes, Osteoarthritis and Cartilage, vol. 12, No. 3, Mar. 2004, pp. 239-244.
Lavaud et al., Exploration of Melanoma Metastases in Mice Brains Using Endogenous Contrast Photoacoustic Imaging, International Journal of Pharmaceutics, vol. 532, No. 2, Nov. 5, 2017, pp. 704-709.
Lazarides et al., A Fluorescence-Guided Laser Ablation System for Removal of Residual Cancer in a Mouse Model of Soft Tissue Sarcoma, Theranostics, vol. 6, No. 2, Jan. 1, 2016, pp. 155-166.
Lebeau et al., Imaging The Urokinase Plasminongen Activator Receptor in Preclinical Breast Cancer Models of Acquired Drug Resistance, Theranostics, vol. 4, No. 3, Jan. 18, 2014, pp. 267-279.
Lee et al., In Vivo Imaging of Hydrogen Peroxide with Chemiluminescent Nanoparticles, Nature Materials, vol. 6, No. 10, Oct. 2007, pp. 765-769.
Leenders et al., Novel Anthracycline-Spacer—β-Glucuronide, -β-Glucoside, and -β-Galactoside Prodrugs for Application in Selective Chemotherapy, Bioorganic & Medicinal Chemistry, vol. 7, No. 8, Aug. 1999, pp. 1597-1610.
Lerner et al., Biochemistry of Melanin Formation, Physiological Reviews, vol. 30, No. 1, Jan. 1950, pp. 91-126.
Lerner, Melanin Pigmentation, The American Journal of Medicine, vol. 19, No. 6, Dec. 1, 1955, pp. 902-924.
Levi et al., Design, Synthesis and Imaging of an Activatable Photoacoustic Probe, Journal of the American Chemical Society, vol. 132, No. 32, Aug. 2010, pp. 11264-11269.
Levi et al., Molecular Photoacoustic Imaging of Follicular Thyroid Carcinoma, Clinical Cancer Research, vol. 19, No. 6, Mar. 15, 2013, pp. 1494-1502.
Li et al., A Self-Calibrating Paracest MRI Contrast Agent That Detects Esterase Enzyme Activity, Contrast Media & Molecular Imaging, vol. 6, No. 4, Jul. 2011, pp. 219-228.
Li et al., Photoacoustic Imaging of LacZ Gene Expression in Vivo, Journal of Biomedical Optics, vol. 12, No. 2, Mar.-Apr. 2007, pp. 020504-1-020504-3.
Li et al., Quinone-Induced Protein Modifications: Kinetic Preference for Reaction of 1,2-Benzoquinones with Thiol Groups in Proteins, Free Radic. Biol. Med., vol. 97, May 19, 2016, pp. 148-157.
Liopo et al., Melanin Nanoparticles as A Novel Contrast Agent for Optoacoustic Tomography, Photoacoustics, vol. 3, No. 1, Mar. 2015, pp. 35-43.
Liu et al., Design and Characterization of a New Irreversible Responsive PARACEST MRI Contrast Agent That Detects Nitric Oxide, Magnetic Resonance in Medicine, vol. 58, No. 6, Dec. 2007, pp. 1249-1256.
Liu et al., Imaging Beta-Galactosidase Activity in Human Tumor Xenografts and Transgenic Mice Using a Chemiluminescent Substrate, The Public Library of Science One, vol. 5, No. 8, Aug. 2010, pp. 1-7.
Liu et al., Using Tyrosinase as a Tri-Modality Reporter Gene to Monitor Transplanted Stem Cells in Acute Myocardial Infarction, Experimental & Molecular Medicine, vol. 50, No. 4, Apr. 27, 2018, pp. 1-10.

(56) References Cited

OTHER PUBLICATIONS

Liyanage et al., Differential Roles of Protease Isoforms in the Tumor Microenvironment, Cancer and Metastasis Reviews, vol. 38, No. 3, Sep. 2019, pp. 389-415.
Longo et al., Melanin-Based Contrast Agents for Biomedical Optoacoustic Imaging and Theranostic Applications, International Journal of Molecular Sciences, vol. 18, No. 8, Aug. 2017, pp. 1-20.
Longo et al., Water Soluble Melanin Derivatives for Dynamic Contrast Enhanced Photoacoustic Imaging of Tumor Vasculature and Response to Antiangiogenic Therapy, Advanced Healthcare Materials, vol. 6, No. 1, 2017, pp. 1-27.
Louie et al., In Vivo Visualization of Gene Expression Using Magnetic Resonance Imaging, Nature Biotechnology, vol. 18, Mar. 2000, pp. 321-325.
Lutzweiler et al., Optoacoustic Imaging and Tomography: Reconstruction Approaches and Outstanding Challenges in Image Performance and Quantification, Sensors, vol. 13, No. 6, Jun. 2013, pp. 7345-7384.
Mahmoudi et al., 5-aminolevulinic Acid Photodynamic Therapy for the Treatment of High-grade Gliomas, Journal of Neuro-oncology, vol. 141, No. 3, Feb. 2019, 22 pages.
Malone et al., Tumor Detection at 3 Tesla with an Activatable Cell Penetrating Peptide Dendrimer (ACPPD-Gd), a T1 Magnetic Resonance (MR) Molecular Imaging Agent, The Public Library of Science, vol. 10, No. 9, Sep. 3, 2015, pp. 1-15.
Marmol et al., Tyrosinase and Related Proteins in Mammalian Pigmentation, FEBS Letters, vol. 381, No. 3, Mar. 4, 1996, pp. 165-168.
Mason, A Classification of Melanins, Annals of the New York Academy of Sciences, 1948, pp. 399-404.
Mason et al., Proteolytic Networks in Cancer, Trends in Cell Biology, vol. 21, No. 4, Apr. 2011, 18 pages.
Mee et al., Total Synthesis of 5,5',6,6'-Tetrahydroxy-3,3'-Biindolyl, The Proposed Structure of a Potent Antioxidant Found in Beetroot (*Beta vulgaris*), Tetrahedron, vol. 60, No. 16, Apr. 12, 2004, pp. 3695-3712.
Metildi et al., Ratiometric Activatable Cell-Penetrating Peptides Label Pancreatic Cancer, Enabling Fluorescence-guided Surgery, Which Reduces Metastases and Recurrence in Orthotopic Mouse Models, Annals of Surgical Oncology, vol. 22, No. 6, Jun. 2015, pp. 2082-2087.
Meyer et al., Clinical Evaluation of 5-S-cysteinyldopa Testing Using a New and Optimized Detection System as a Tumour Marker for Malignant Melanoma, Melanoma Research, vol. 12, No. 5, Oct. 2002, pp. 471-477.
Miampamba et al., Sensitive in Vivo Visualization of Breast Cancer Using Ratiometric Protease-activatable Fluorescent Imaging Agent, AVB-620, Theranostics, vol. 7, No. 13, Aug. 11, 2017, pp. 3369-3386.
Miao et al., Semiconducting Oligomer Nanoparticles as an Activatable Photoacoustic Probe with Amplified Brightness for in Vivo Imaging of pH, Advanced Materials, vol. 28, No. 19, Mar. 22, 2016, pp. 3662-3668.
Micillo et al., Eumelanin Broadband Absorption Develops from Aggregation-Modulated Chromophore Interactions Under Structural and Redox Control, Scientific Reports, vol. 7, No. 1, Feb. 2, 2017, pp. 1-12.
Mieog et al., Image-Guided Tumor Resection Using Real-Time Near-Infrared Fluorescence in a Syngeneic Rat Model of Primary Breast Cancer, Breast Cancer Research and Treatment, vol. 128, No. 3, Aug. 2011, pp. 679-689.
Miller et al., Considering Sex as a Biological Variable in Preclinical Research, The FASEB Journal, vol. 31, No. 1, Jan. 2017, pp. 29-34.
Mito et al., Intraoperative Detection and Removal of Microscopic Residual Sarcoma Using Wide-field Imaging, Cancer, vol. 118, Nov. 2012, pp. 5320-5330.
Mondal et al., Kinetics of Melanin Polymerization During Enzymatic and Nonenzymatic Oxidation, The Journal of Physical Chemistry B, vol. 122, No. 7, Jan. 24, 2018, pp. 2047-2063.
Muhanna et al., Multimodal Image-guided Surgical and Photodynamic Interventions in Head and Neck Cancer: From Primary Tumor to Metastatic Drainage, Clinical Cancer Research, vol. 22, No. 4, pp. 961-970, Feb. 15, 2016.
Murphy et al., Synthesis of 5,6-Dihydroxyindole: A Novel Reductive Cyclization of (E)-4,5-Dihydroxy-2, β- Dinitrostyrene, Synthetic Communications, vol. 15, No. 4, Mar. 1, 1985, pp. 321-329.
Neuschler et al., A Pivotal Study of Optoacoustic Imaging to Diagnose Benign and Malignant Breast Masses: A New Evaluation Tool for Radiologists, Radiology, vol. 287, No. 2, May 2018, pp. 398-412.
Neuschmelting et al., Lymph Node Micrometastases and In-Transit Metastases from Melanoma: In Vivo Detection with Multispectral Optoacoustic Imaging in a Mouse Model, Radiology, vol. 280, No. 1, Jul. 2016, pp. 137-150.
Nguyen et al., Surgery With Molecular Fluorescence Imaging Using Activatable Cell-penetrating Peptides Decreases Residual Cancer and Improves Survival, Proceedings of the National Academy of Sciences of the United States of America, vol. 107, No. 9, Mar. 2, 2010, pp. 4317-4322.
Novellino et al., Expedient Synthesis of 5,6-Dihydroxyindole and Derivatives Via an Improved Zn(II)-Assisted 2,β-Dinitrostyrene Approach, Synthesis, vol. 1999, No. 5, May 1999, pp. 793-796.
Ntziachristos et al., Molecular Imaging by Means of Multispectral Optoacoustic Tomography (MSOT), Chemical Reviews, vol. 110, No. 5, May 12, 2010, pp. 2783-2794.
Ofori et al., Design of Protease Activated Optical Contrast Agents That Exploit a Latent Lysosomotropic Effect for Use in Fluorescence-Guided Surgery, The American Chemical Society Chemical Biology, vol. 10, No. 9, Sep. 18, 2015, pp. 1977-1988.
Okuda et al., Possible Oxidative Polymerization Mechanism of 5,6-Dihydroxyindole from Ab Initio Calculations, The Journal of Physical Chemistry A, vol. 122, No. 44, Nov. 2008, pp. 11213-11222.
Olson et al., Activatable Cell Penetrating Peptides Linked to Nanoparticles as Dual Probes for in Vivo Fluorescence and MR Imaging of Proteases, Proceedings of the National Academy of Sciences of the United States of America, vol. 107, No. 9, Feb. 16, 2010, pp. 4311-4316.
Orosco et al., Molecular Targeting of Papillary Thyroid Carcinoma With Fluorescently Labeled Ratiometric Activatable Cell Penetrating Peptides in a Transgenic Murine Model, Journal of Surgical Oncology, vol. 113, No. 2, Feb. 2016, pp. 138-143.
Pagel et al., Structures and Related Properties of Helical, Disulfide-stabilized Peptides, Ph.D. dissertation. Lawrence Berkeley Laboratory, University of California, Berkeley, Structures and related properties of helical, disulfide-stabilized peptides, Nov. 1, 1993, 210 pages.
Paproski et al., Multi-Wavelength Photoacoustic Imaging of Inducible Tyrosinase Reporter Gene Expression in Xenograft Tumors, Scientific Reports, vol. 4, Jun. 2014, pp. 1-7.
Paproski et al., Tyrosinase as a Dual Reporter Gene for Both Photoacoustic and Magnetic Resonance Imaging, Biomedical Optics Express, vol. 2, No. 4, Apr. 2011, pp. 771-780.
Paproski et al., Validating Tyrosinase Homologue MelA as a Photoacoustic Reporter Gene for Imaging *Escherichia coli*, Journal of Biomedical Optics, vol. 20, No. 10, Oct. 2015, pp. 106008-1-106008-8.
Parraga et al., 2,3,9- and 2,3,11-Trisubstituted Tetrahydroprotoberberines as D2 Dopaminergic Ligands, European Journal of Medicinal Chemistry, vol. 68, Oct. 2013, pp. 1-57.
Pawelek et al., 5,6-dihydroxyindole is a Melanin Precursor Showing Potent Cytotoxicity, Nature, vol. 276, Dec. 7, 1978, pp. 627-628.
International Application No. PCT/US2021/043172, International Preliminary Report on Patentability mailed on Feb. 9, 2023, 6 pages.
International Application No. PCT/US2021/043172, International Search Report and Written Opinion mailed on Nov. 5, 2021, 6 pages.
Piletic et al., Estimation of Molar Absorptivities and Pigment Sizes for Eumelanin and Pheomelanin Using Femtosecond Transient Absorption Spectroscopy, The Journal of Chemical Physics, vol. 131, No. 18, Oct. 2009, pp. 181106-1-181106-4.

(56) References Cited

OTHER PUBLICATIONS

Pu et al., Semiconducting Polymer Nanoparticles as Photoacoustic Molecular Imaging Probes in Living Mice, Nature Nanotechnology, vol. 9, No. 3, Mar. 2014, pp. 233-239.
Pulz et al., Proteases as Prognostic Markers in Human and Canine Cancers, Veterinary and Comparative Oncology, vol. 15, No. 3, Sep. 2017, pp. 669-683.
Qin et al., Tyrosinase as a Multifunctional Reporter Gene for Photoacoustic/MRI/PET Triple Modality Molecular Imaging, Scientific Reports, vol. 3, Mar. 2013, pp. 1-8.
Randtke et al., The Hanes-Woolf Linear QUESP Method Improves the Measurements of Fast Chemical Exchange Rates With CEST MRI, Magnetic Resonance in Medicine, vol. 71, Apr. 2014, pp. 1603-1612.
Ren et al., Non-Invasive Imaging of Cysteine Cathepsin Activity in Solid Tumors Using a 64Cu-Labeled Activity-Based Probe, The Public Library of Science, vol. 6, No. 11, Nov. 2011, pp. 1-9.
Ronald et al., Total Synthesis of Frustulosin and Aurocitrin, Journal of Organic Chemistry, vol. 47, Jun. 1982, pp. 2541-2549.
Rosen et al., Dendron-Mediated Self-Assembly, Disassembly, and Self-Organization of Complex Systems, Chemical Reviews, vol. 109, Oct. 30, 2009, pp. 6275-6540.
Roth-Konforti et al., Unprecedented Sensitivity in a Probe for Monitoring Cathepsin B: Chemiluminescence Microscopy Cell-Imaging of a Natively Expressed Enzyme, Angewandte Chemie International Edition, vol. 56, No. 49, Oct. 11, 2017, pp. 15633-15638.
Sameshima et al., Biochemical Diagnoses of Malignant Melanomas With Determinations of 5-S-Cysteinyldopa in Lesions, The Japanese Journal of Dermatology, vol. 99, No. 6, May 1, 1989, pp. 665-672.
Santibanez, Urokinase Type Plasminogen Activator and the Molecular Mechanisms of its Regulation in Cancer, Protein and Peptide Letters, vol. 24, No. 10, Aug. 2017, pp. 936-946.
Sato et al., Structure-Activity Relationship for (+)-Taxifolin Isolated from Silymarin as an Inhibitor of Amyloid β Aggregation, Bioscience, Biotechnology, and Biochemistry, vol. 77, No. 5, May 23, 2013, pp. 1100-1103.
Savariar et al., Real-Time in Vivo Molecular Detection of Primary Tumors and Metastases With Ratiometric Activatable Cell-Penetrating Peptides, Cancer Research, vol. 73, No. 2, Jan. 2013, pp. 855-864.
Schwarz et al., Three-dimensional Multispectral Optoacoustic Mesoscopy Reveals Melanin and Blood Oxygenation in Human Skin in Vivo, Journal of Biophotonics, vol. 9, No. 1-2, Jan. 2016, pp. 55-60.
Segal et al., Detection of Intestinal Cancer by Local, Topical Application of a Quenched Fluorescence Probe for Cysteine Cathepsins, The American Chemical Society Chemical Biology, vol. 22, No. 1, Jan. 2015, pp. 148-158.
Selvarajan et al., Kinetic Studies on Exploring Lactose Hydrolysis Potential of β Galctosidase Extracted From *Lactobacillus plantarum* HF571129, Journal of Food Science and Technology, vol. 52, No. 10, Oct. 2015, pp. 6206-6217.
Shabat, Self-immolative Dendrimers as Novel Drug Delivery Platforms, Journal of Polymer Science Part A, vol. 44, Jan. 26, 2006, pp. 1569-1578.
Shah et al., Detecting Human Melanoma Cell Re-Differentiation Following BRAF or Heat Shock Protein 90 Inhibition Using Photoacoustic and Magnetic Resonance Imaging, Scientific Reports, vol. 7, No. 1, Aug. 15, 2017, 9 pages.
Shamis et al., Bioactivation of Self-Immolative Dendritic Prodrugs by Catalytic Antibody 38C2, Journal of the American Chemical Society, vol. 126, Feb. 2004, pp. 1726-1731.
Sheth et al., Improved Detection of Ovarian Cancer Metastases by Intraoperative Quantitative Fluorescence Protease Imaging in a Pre-Clinical Model, Gynecologic Oncology, vol. 112, No. 3, Mar. 2009, pp. 616-622.
Shimizu et al., Intraoperative Photodynamic Diagnosis Using Talaporfin Sodium Simultaneously Applied for Photodynamic Therapy against Malignant Glioma: A Prospective Clinical Study, Frontiers in Neurology, Jan. 30, 2018, 9 pages.
Sinharay et al., Detecting in Vivo Urokinase Plasminogen Activator Activity With a CatalyCEST MRI Contrast Agent, NMR in Biomedicine, vol. 30, No. 7, Jul. 2017, pp. 1-16.
Sinharay et al., Detection of Enzyme Activity and Inhibition During Studies in Solution, in Vitro and in Vivo With CatalyCEST MRI, Molecular Imaging and Biology, vol. 20, No. 2, Apr. 2018, pp. 240-248.
Sinharay et al., Detection of Sulfatase Enzyme Activity with a CatalyCEST MRI Contrast Agent, Chemistry, vol. 22, No. 19, May 4, 2016, 10 pages.
Sinharay et al., Noninvasive Detection of Enzyme Activity in Tumor Models of Human Ovarian Cancer Using CatalyCEST MRI, Magnetic Resonance in Medicine, vol. 77, No. 5, May 2017, pp. 2005-2014.
Sliutz et al., Quantification of uPA Receptor Expression in Human Breast Cancer Cell Lines By cRT-PCR, Breast Cancer Research and Treatment, vol. 40, No. 3, Oct. 1996, pp. 257-263.
Solano, Melanin and Melanin-related Polymers as Materials With Biomedical and Biotechnological Applications—Cuttlefish Ink and Mussel Foot Proteins as Inspired Biomolecules, International Journal of Molecular Sciences, vol. 18, No. 7, Jul. 2017, pp. 1-18.
Stockfleth et al., Optimized Detection of 5-S-cysteinyldopa (5-S-CD) in Serum of Melanoma Patients: A New Marker of Metastatic Melanoma, Melanoma, vol. 33, No. S8, Sep. 18, 1997, p. S257.
Stoffels et al., Metastatic Status of Sentinel Lymph Nodes in Melanoma Determined Noninvasively with Multispectral Optoacoustic Imaging, Science Translational Medicine, vol. 7, No. 317, Dec. 9, 2015, pp. 1-10.
Stritzker et al., Vaccinia Virus-Mediated Melanin Production Allows MR and Optoacoustic Deep Tissue Imaging and Laser-Induced Thermotherapy of Cancer, Proceedings of the National Academy of Sciences of the United States of America, vol. 110, No. 9, Feb. 2013, pp. 3316-3320.
Su et al., Gene Expression Imaging by Enzymatic Catalysis of a Fluorescent Probe via Membrane-anchored Beta-glucuronidase, Gene Therapy, vol. 14, No. 7, Jan. 18, 2007, pp. 565-574.
Su et al., PET Imaging of β-Glucuronidase Activity by an Activity-based 124I-trapping Probe for the Personalized Glucuronide Prodrug Targeted Therapy, Molecular Cancer Therapeutics, vol. 13, Dec. 2014, pp. 2852-2863.
Szpaderska et al., An Intracellular Form of Cathepsin B Contributes to Invasiveness in Cancer, Cancer Research, vol. 61, No. 8, Apr. 15, 2001, pp. 3493-3500.
Tang et al., Insulin-Releasing Activity of a Series of Phenylalanine Derivatives, European Journal of Medicinal Chemistry, vol. 43, No. 9, Sep. 1, 2008, pp. 1997-2003.
Taralp et al., Characterization of the S3 Subsite Specificity of Cathepsin B, Journal of Biological Chemistry, vol. 270, No. 30, Jul. 28, 1995, pp. 18036-18043.
Taruttis et al., Advances in Real-time Multispectral Optoacoustic Imaging and Its Applications, Nature Photonics, vol. 9, Mar. 31, 2015, pp. 219-227.
Taruttis et al., Fast Multispectral Optoacoustic Tomography (MSOT) for Dynamic Imaging of Pharmacokinetics and Biodistribution in Multiple Organs, The Public Library of Science One, vol. 7, No. 1, Jan. 2012, pp. 1-6.
Tsuda et al., Near-infrared Fluorescence Imaging and Photodynamic Therapy With Indocyanine Green Lactosome Has Antineoplastic Effects for Hepatocellular Carcinoma, The Public Library of Science One, vol. 12, Aug. 31, 2017, pp. 1-12.
Tsukamoto et al., 5,6-Dihydroxyindole-2-Carboxylic Acid is Incorporated in Mammalian Melanin, Biochemical Journal, vol. 286, No. 2, Sep. 1, 1992, pp. 491-495.
Tung et al., In Vivo Imaging of Beta-Galactosidase Activity Using Far Red Fluorescent Switch, Cancer Research, vol. 64, No. 5, Mar. 2004, pp. 1579-1583.
Turk et al., Cysteine Cathepsins: From Structure, Function and Regulation to New Frontiers, Biochimica et Biophysica Acta, vol. 1824, No. 1, Jan. 2012, pp. 68-88.

(56) References Cited

OTHER PUBLICATIONS

Tzou et al., Micro-Pet Imaging of B-Glucuronidase Activity by the Hydrophobic Conversion of a Glucuronide Probe, Radiology, vol. 252, No. 3, Sep. 2009, pp. 754-762.
Unkart et al., Intraoperative Tumor Detection Using a Ratiometric Activatable Fluorescent Peptide: A First-in-human Phase 1 Study, Annals of Surgical Oncology, vol. 24, No. 11, Jul. 2017, pp. 3167-3173.
Uusitalo et al., Recent Advances in Intracellular and in Vivo ROS Sensing: Focus on Nanoparticle and Nanotube Applications, International Journal of Molecular Sciences, vol. 13, No. 9, Aug. 24, 2012, pp. 10660-10679.
Valko-Rokytovska et al., Specific Urinary Metabolites in Malignant Melanoma, Medicina, vol. 55, No. 5, May 16, 2019, pp. 1-10.
Valluru et al., Photoacoustic Imaging in Oncology: Translational Preclinical and Early Clinical Experience, Radiology, vol. 280, No. 2, Aug. 2016, pp. 332-349.
Van Dort et al., Radiosynthesis and Evaluation of 5-[125I]lodoindol-3-yl-β-D-galactopyranoside ([125I]IBDG) as a β-Galactosidase Imaging Radioligand, Molecular Imaging, vol. 7, Jul. 2008, pp. 187-197.
Velasco, Design, Synthesis and Application of CatalyCEST MRI Agents for Enzyme Detection, The University of Arizona, 2017, 169 pages.
Verdoes et al., A Non-Peptidic Cathepsin S Activity-Based Probe for Noninvasive Optical Imaging of Tumor-Associated Macrophages, Chemistry and Biology, vol. 19, No. 5, May 25, 2012, pp. 1-18.
Vezenkov et al., Development of Fluorescent Peptide Substrates and Assays for the Key Autophagy-initiating Cysteine Protease Enzyme, ATG4B, Bioorganic & Medicinal Chemistry, vol. 23, No. 13, Jul. 1, 2015, pp. 3237-3247.
Vidak et al., Cysteine Cathepsins and Their Extracellular Roles: Shaping the Microenvironment, Cells, vol. 8, No. 3, Mar. 20, 2019, pp. 1-24.
Vilema-Enríquez et al., Molecular and Cellular Effects of Hydrogen Peroxide on Human Lung Cancer Cells: Potential Therapeutic Implications, Oxidative Medicine and Cellular Longevity, vol. 2016, No. 1, Jun. 8, 2016, pp. 1-12.
Waldner et al., Multispectral Optoacoustic Tomography in Crohn's Disease: Noninvasive Imaging of Disease Activity, Gastroenterology, vol. 151, Aug. 2016, pp. 238-240.
Wallace et al., Alleviating Cancer Drug Toxicity by Inhibiting a Bacterial Enzyme, Science, vol. 330, No. 6005, Nov. 2010, pp. 831-835.
Wang et al., Lysosome-Targeting Fluorogenic Probe for Cathepsin B Imaging in Living Cells, Analytical Chemistry, vol. 88, No. 24, Nov. 15, 2016, pp. 12403-12410.
Weber et al., Contrast Agents for Molecular Photoacoustic Imaging, Nature Methods, vol. 13, No. 8, Aug. 2016, pp. 639-650.
Wehrman et al., Luminescent Imaging of Beta-galactosidase Activity in Living Subjects Using Sequential Reporter-Enzyme Luminescence, Nature Methods, vol. 3, Mar. 2006, pp. 295-301.
Weissleder et al., In vivo Imaging of Tumors with Protease-Activated Near-Infrared Fluorescent Probes, Nature Biotechnology, vol. 17, No. 4, Apr. 1999, pp. 375-378.
Whitley et al., A Mousehuman Phase 1 Co-Clinical Trial of a Protease-Activated Fluorescent Probe for Imaging Cancer, Science Translational Medicine, vol. 8, No. 320, Jan. 2016, pp. 1-24.
Widanelage, et al., Design, Synthesis and Evaluation of Caged Melanin Precursors for Photoacoustic Imaging, Available Online at: http://hdl.handle.net/10150/648583, 2020, 278 pages.
Withana et al., Cathepsin B Inhibition Limits Bone Metastasis In Breast Cancer, Cancer research, vol. 72, No. 5, Mar. 2012, pp. 1199-1209.
Wuts et al., Greene's Protective Groups in Organic Synthesis, 4th Edition, John Wiley & Sons, Inc., New York, NY, Apr. 10, 2006, 27 pages.
Xia et al., An Enzyme-Sensitive Probe for Photoacoustic Imaging and Fluorescence Detection of Protease Activity, Nanoscale, vol. 3, Jan. 2011, pp. 950-953.
Xing et al., Quantification of Cathepsins B and L in Cells, Biochemical Journal, vol. 332, No. 2, Jun. 1998, pp. 499-505.
Yamada et al., Measurement of Eumelanin Precursor Metabolites in the Urine as a New Marker for Melanoma Metastases, Archives of Dermatological Research, vol. 128, No. 4, Apr. 1992, pp. 491-494.
Yang et al., Visualization of Protease Activity in Vivo Using an Activatable Photoacoustic Imaging Probe Based on CuS Nanoparticles, Theranostics, vol. 4, No. 2, Jan. 2014, pp. 134-141.
Yhee et al., Cathepsin B Imaging to Predict Quality of Engineered Cartilage, Macromolecular Bioscience, vol. 15, No. 9, Sep. 2015, pp. 1224-1232.
Yin et al., Degradable Semiconducting Oligomer Amphiphile for Ratiometric Photoacoustic Imaging of Hypochlorite, The American Chemical Society Nano, vol. 11, No. 4, Apr. 25, 2017, pp. 4174-4182.
Yoo et al., A Facile Synthesis of α-Amino-Dota as A Versatile Molecular Imaging Probe, Tetrahedron Letters, vol. 47, No. 41, Oct. 2006, pp. 7327-7330.
Yoo et al., A PARACEST MRI Contrast Agent to Detect Enzyme Activity, Journal of the American Chemical Society, vol. 128, Oct. 2006, pp. 14032-14033.
Yoo et al., An Amine-Derivatized, DOTA-Loaded Polymeric Support for Fmoc Solid Phase Peptide Synthesis, Tetrahedron Letters, vol. 50, No. 31, Aug. 5, 2009, 8 pages.
Yoo et al., Detection of in Vivo Enzyme Activity with catalyCEST MRI, Magnetic Resonance in Medicine, vol. 71, No. 3, Mar. 2014, pp. 1221-1230.
Yoo et al., Enzyme-responsive PARACEST MRI Contrast Agents: a New Biomedical Imaging Approach for Studies of the Proteasome, Contrast Media & Molecular Imaging, vol. 2, No. 4, Jul. 2007, pp. 189-198.
Yoo et al., Peptidyl Molecular Imaging Contrast Agents Using a New Solid Phase Peptide Synthesis Approach, Bioconjugate Chemistry, vol. 18, No. 3, Mar. 2007, pp. 903-911.
Zajc et al., Expression of Cathepsin B is Related to Tumorigenicity of Breast Cancer Cell Lines, Radiology and Oncology, vol. 37, No. 4, Dec. 2003, pp. 233-240.
Zha et al., Enzyme-responsive Copper Sulphide Nanoparticles for Combined Photoacoustic Imaging, Tumor-selective Chemotherapy and Photothermal Therapy, Chemical Communications, vol. 49, No. 33, Mar. 2013, pp. 3455-34457.
Zhang et al., Activatable Photoacoustic Nanoprobes for In Vivo Ratiometric Imaging of Peroxynitrite, Advanced Materials, vol. 29, No. 6, 2017, pp. 1-18.
Zhang et al., Bioinspired Multifunctional Melanin-Based Nanoliposome for Photoacoustic/Magnetic Resonance Imaging-Guided Efficient Photothermal Ablation of Cancer, Theranostics, vol. 8, No. 6, Feb. 7, 2018, pp. 1591-1606.
Zhang et al., Engineering Melanin Nanoparticles as an Efficient Drug-delivery System for Imaging-guided Chemotherapy, Advanced Materials, vol. 27, No. 34, Jul. 2015, pp. 5063-5069.
Zhang et al., In Vivo Optical Imaging of LacZ Expression Using LacZ Transgenic Mice, ASSAY and Drug Development Technologies, vol. 7, No. 4, Sep. 2009, pp. 391-399.
Zheng et al., Tyrosinase-Based Reporter Gene for Photoacoustic Imaging of MicroRNA-9 Regulated by DNA Methylation in Living Subjects, Molecular Therapy, Nucleic Acids, vol. 11, Jun. 1, 2018, pp. 34-40.
Zhong et al., Cathepsin B-Cleavable Doxorubicin Prodrugs for Targeted Cancer Therapy (Review), International Journal of Oncology, vol. 42, No. 2, Feb. 2013, pp. 373-383.
Zhou et al., Handheld Photoacoustic Probe to Detect Both Melanoma Depth and Volume at High Speed in Vivo, Journal of Biophotonics, vol. 8, No. 11-12, Nov. 2015, pp. 961-967.
Zhou et al., Melanin-like Nanoparticles Decorated with an Autophagy-inducing Peptide for Efficient Targeted Photothermal Therapy, Biomaterials, vol. 203, May 2019, pp. 63-72.
Zhu et al., In Vivo Optical Imaging of Membrane-Type Matrix Metalloproteinase (MT-MMP) Activity, Molecular Pharmaceutics, vol. 8, No. 6, Dec. 5, 2011, pp. 1-16.

tyrosine L-DOPA leucodopa-chrome cysteinyldopa eumelanin pheomelanin

Agent 1

Agent 3

Agent 2

800

810
Insert, into cell, reporter gene construct comprising gene encoding hydrolase enzyme 815
Observe background melanin in the cell prior to administering compound 820
Administer to cell compound comprising melanin precursor and carbohydrate blocking spontaneous melanin synthesis 830
Observe spontaneously-synthesized melanin in the cell PAI signal (au)
6
4
2
0
700
750
800
850
900
Wavelength (nm)
mg/mL
2.22
1.66
1.11
0.84
0.55

Absorbance (au)
0.8
0.6
0.4
0.2
0.0
700
750
800
850
900
Wavelength (nm)
mg/mL
2.22
1.66
1.11
0.84
0.55

SNR (%)
100
75
50
25
0
0.5
1
1.5
2
2.5
Concentration (mg/mL)

SNR (%)
100
75
50
25
0
0.5
1
1.5
2
2.5
Concentration (mg/mL)

CONTRAST AGENTS FOR DETECTION OF ENZYME ACTIVITIES BASED ON MELANIN SYNTHESIS

CROSS-REFERENCES TO RELATED APPLICATIONS

This application is a national stage application, filed under 35 U.S.C. § 371, of International Patent Application No. PCT/US2021/043172, filed Jul. 26, 2021, which claims priority to and the benefit of U.S. Provisional Application No. 63/057,074, filed Jul. 27, 2020, which is incorporated herein by reference in its entirety.

GOVERNMENT SUPPORT STATEMENT

This invention was made with government support under grant number EB028062 from the National Institute for Biomedical Imaging and Bioengineering of the National Institutes of Health of the United States of America. The government has certain rights in the invention.

FIELD OF THE INVENTION

The present invention relates generally to the field of cancer treatment. More particularly, it concerns contrast agents for detection of enzyme activities, such as protease activities, based on melanin synthesis.

BACKGROUND OF THE INVENTION

Surgical resection is a well-known technique for the treatment of solid tumors. However, surgical resection is limited by the difficulty of distinguishing healthy tissue from tumors, especially small tumors.

Prior workers have developed optical surgical navigation using fluorescent contrast agents. The contrast agent is targeted to the tumor and fluorescence is induced. Fluorescent contrast agents can preferentially highlight tumors, especially many small tumors within normal tissue, thereby improving the detection of tumors during surgery.

However, optical surgical navigation using fluorescent contrast agents has several shortcomings. For example, firstly, fluorescence contrast agents must be guided to the tumor to be effective. As a second example, fluorescence imaging instruments must be introduced to the surgical arena. The fluorescence imaging instruments must be placed in proximity to the patient, which may hinder the ability of the surgical team to operate. To maximize the visible contrast of most fluorophores currently known, the operating room should be kept dark, which may further hinder the surgical team. Also, fluorophores, being unnatural, may impose a serious compliance and regulatory-approval burden.

Accordingly, it would be desirable to develop optical surgical navigation techniques using one or more of naturally-occurring and biocompatible contrast agents, contrast agents that are preferentially activated in tumors, and that impart optical contrast that requires little or no instrumentation to induce or detect. It would be desirable for such optical contrast agents to be detectable by known, non-fluorescence-based techniques and/or to provide optical contrast visible to the naked eye.

SUMMARY OF THE INVENTION

The following presents a simplified summary of the disclosure in order to provide a basic understanding of some aspects of the disclosure. This summary is not an exhaustive overview of the disclosure. It is not intended to identify key or critical elements of the disclosure or to delineate the scope of the disclosure. Its sole purpose is to present some concepts in a simplified form as a prelude to the more detailed description that is discussed later.

In one embodiment, the present disclosure relates to a composition, comprising: a compound, comprising: a melanin precursor that spontaneously synthesizes a melanin when in free form in vivo, and a peptide directly covalently bonded to or indirectly linked to the melanin precursor, wherein the direct covalent bond or indirect link of the peptide to the melanin precursor blocks spontaneous synthesis of the melanin in vivo in the absence of protease activity.

In one embodiment, the present disclosure relates to a method, comprising: administering, to a patient suffering from a tumor, a composition as referred to above; and surgically resecting the tumor, wherein the surgical resection is guided at least in part by contrast imparted by the melanin, wherein the melanin is spontaneously synthesized in the tumor after administering the composition.

In one embodiment, the present disclosure relates to a method, comprising: administering, to a patient suffering from a tumor, a composition as referred to above; and thermally ablating the tumor.

In one embodiment, the present disclosure relates to a method, comprising: administering, to a patient suffering from a tumor, a composition as referred to above; and detecting the tumor with noninvasive imaging.

In one embodiment, the present disclosure relates to a kit, comprising a composition as described above; and instructions for use of the composition in a method comprising administering, to a patient suffering from a tumor, the composition; and surgically resecting and/or thermally ablating the tumor, wherein the surgical resection is guided at least in part by contrast imparted by, or the thermally ablating targets cells containing, melanin spontaneously synthesized by the tumor after administering the composition.

In one embodiment, the present disclosure relates to a composition, comprising: a compound, comprising: a melanin precursor that spontaneously synthesizes a melanin when in free form in vivo, a linker moiety covalently bonded to the melanin precursor, and a carbohydrate covalently bonded to the linker moiety, wherein the indirect link of the carbohydrate to the melanin precursor blocks spontaneous synthesis of the melanin in vivo in the absence of hydrolase activity.

In one embodiment, the present disclosure relates to a method, comprising: inserting, into at least one cell of an organism, a reporter gene construct comprising a regulatory sequence of interest and a coding sequence for a hydrolase enzyme; administering, to the cell, a composition comprising a compound comprising a melanin precursor that spontaneously synthesizes a melanin when in free form in vivo, a linker moiety covalently bonded to the melanin precursor, and a carbohydrate covalently bonded to the linker moiety, wherein the indirect link of the carbohydrate to the melanin precursor blocks spontaneous synthesis of the melanin in vivo in the absence of hydrolase activity; and observing melanin in the cell, wherein the melanin is spontaneously synthesized in the cell after administering the composition.

The compositions disclosed herein may be used in methods and kits disclosed herein to provide optical surgical navigation using one or more of naturally-occurring and biocompatible contrast agents, contrast agents that are preferentially activated in tumors, and that impart optical contrast that requires little instrumentation to induce. The compositions may provide optical contrast to the naked eye.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

Figure 1:
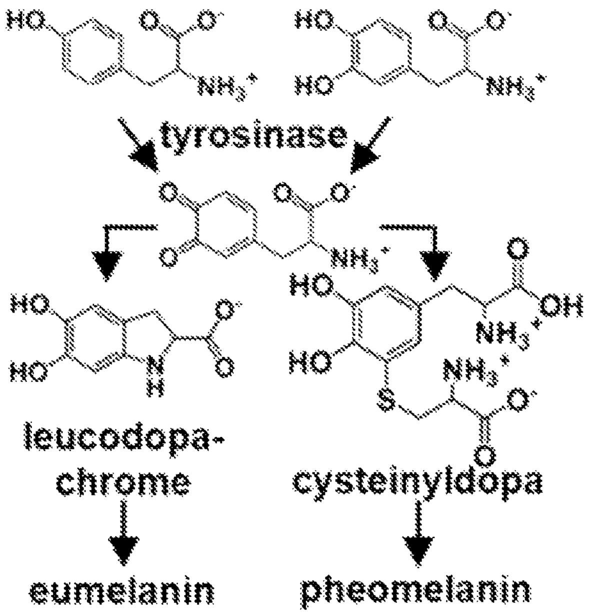
FIG. 1 schematically depicts biochemical reactions that lead from naturally-occurring melanin precursors to formation of eumelanin and pheomelanin.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims. Moreover, the stylized depictions illustrated in the drawings are not drawn to any absolute scale.

DESCRIPTION OF ILLUSTRATIVE EMBODIMENTS

Various illustrative embodiments of the disclosure are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related, regulatory, and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present subject matter will now be described with reference to the attached figures. Various structures, systems, and devices are schematically depicted in the drawings for purposes of explanation only and so as to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, any given numerical value includes the inherent variation of error for the device or the method being employed to determine the value, or the variation that exists between study subjects or healthcare practitioners.

In one embodiment, the present disclosure relates to a composition, comprising a compound. The compound comprises a melanin precursor that spontaneously synthesizes a melanin when in free form in vivo. The compound also comprises a peptide directly covalently bonded to or indirectly linked to the melanin precursor, wherein the direct covalent bond or indirect link of the peptide to the melanin precursor blocks spontaneous synthesis of the melanin in vivo in the absence of protease activity.

A "melanin precursor" as used herein refers to any compound that spontaneously synthesizes a melanin when in free form in vivo. As is known to the person of ordinary skill in the art, "melanin" is a term for several polymeric pigments common in humans, other animals, plants, and microorganism. One common melanin in humans is eumelanin, which typically comprises cross-linked 5,6-dihydroxyindole (DHI) and 5,6-dihydroxyindole-2-carboxylic acid (DHICA) polymers. Depending on the proportions of DHI and DHICA in a eumelanin, eumelanin may be further characterized as brown eumelanin and black eumelanin. A second common melanin in humans is pheomelanin, which differs from eumelanin by typically incorporating benzothiazine and benzothiazole units. At naturally-occurring concentrations in humans, pheomelanins generally impart yellow and red tints to various body features.

"Spontaneous" and grammatical variations thereof, when used herein to refer to a biochemical reaction, means that the biochemical reaction takes place without requiring enzymatic activity. For example, spontaneous formation of a melanin from a melanin precursor forms and/or adds onto a melanin without requiring enzymatic activity.

FIG. 1 schematically depicts biochemical reactions that lead from naturally-occurring melanin precursors to formation of eumelanin and pheomelanin. Though not intended to be exhaustive of all such reactions, FIG. 1 shows that tyrosinase catalyzes the oxidation of tyrosine (upper left) and L-DOPA (also known as levodopa and 1-3,4-dihydroxyphenylalanine; upper right) to yield dopaquinone, that spontaneously converts to leucodopachrome and cysteinyldopa. Leucodopachrome generally, but not exclusively, spontaneously polymerizes to form eumelanin. Cysteinyldopa generally, but not exclusively, spontaneously polymerizes to form pheomelanin.

Accordingly, in one embodiment, the melanin precursor is selected from the group consisting of leucodopachrome, decarboxylated leucodopachrome, and cysteinyldopa.

Figure 10:
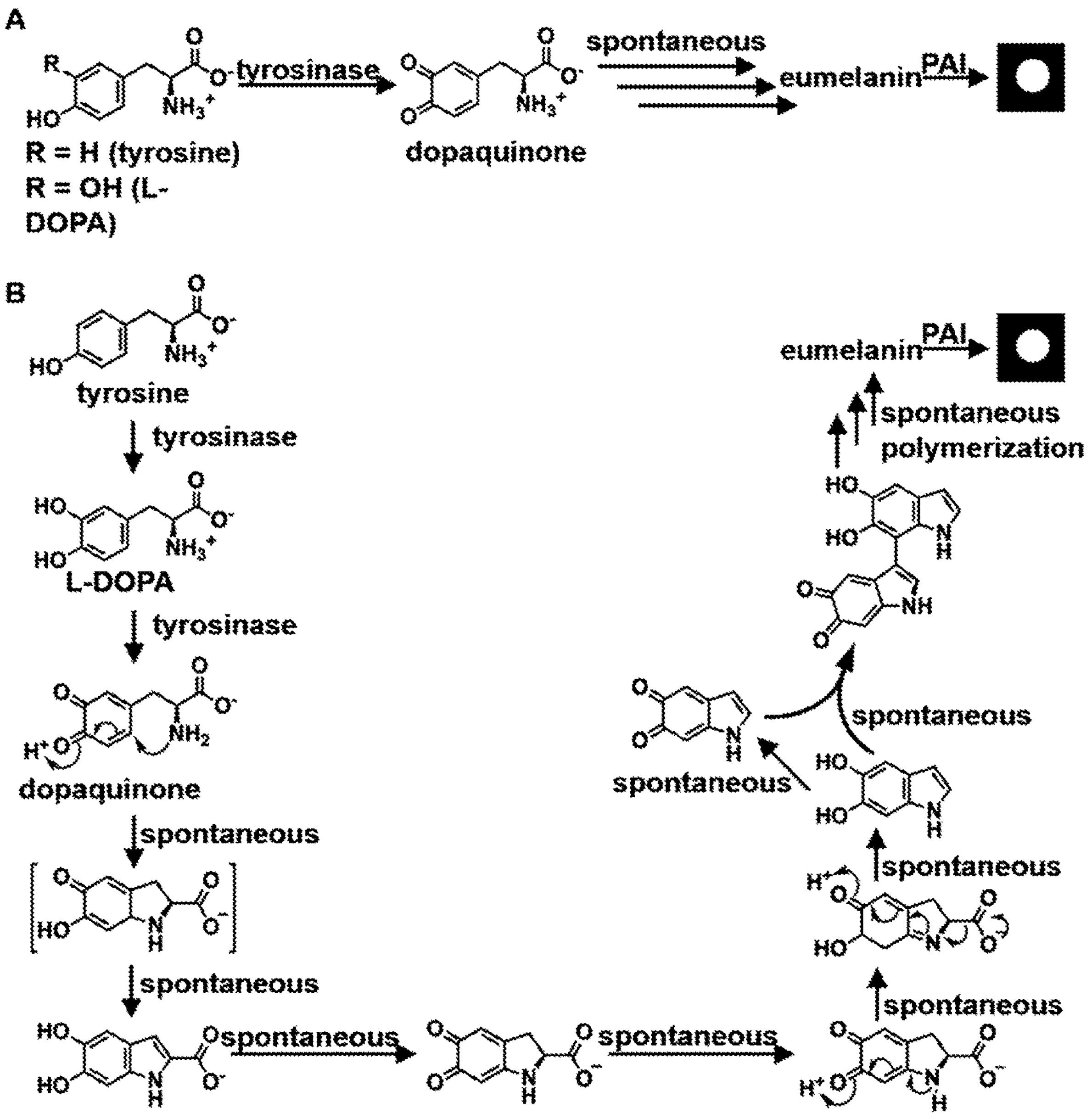
FIG. 10 schematically depicts biochemical reactions that lead from naturally-occurring melanin precursors to formation of eumelanin and pheomelanin.

FIG. 10 schematically depicts other biochemical reactions that lead from naturally-occurring melanin precursors to formation of eumelanin and pheomelanin. Though not intended to be exhaustive of all such reactions, FIG. 10 shows that the formation of eumelanin may be summarized (A) as the oxidation of tyrosine or L-DOPA by tyrosinase to form dopaquinone, followed by spontaneous polymerization to form eumelanin. Pathway (B) shows in more detail that tyrosine is converted to L-DOPA, and L-DOPA to dopaquinone, by tyrosinase, followed by multiple steps to form an indole-quinone, which may then spontaneously polymerized to form eumelanin. Eumelanin can be detected with Multispectral Optoacoustic Tomography/Photoacoustic Imaging (PAL conceptually represented as white circles on black squares).

Accordingly, other melanin precursors, such as DHI and DHICA, among others, may be used in the compound.

As stated above, the compound comprises a melanin precursor and a peptide directly covalently bonded to or indirectly linked to the melanin precursor, wherein the direct covalent bond or indirect link of the peptide to the melanin precursor blocks spontaneous synthesis of the melanin in vivo in the absence of protease activity.

A peptide has a standard meaning in the art and need not be discussed in detail. The peptide may comprise any number of amino acids, and hence, encompasses "oligopeptides," "polypeptides," and "proteins," as those terms are commonly used in the art. Each of the amino acids in the peptide may be independently selected from any known amino acid molecule, i.e., may be selected without being bound by the selection of any amino acid incorporated into the peptide at any other position. The peptide may be synthesized by chemical techniques or purified from a naturally-occurring source.

The chemical formula of the peptide may be chosen without consideration of biochemical activities of the free peptide. However, in embodiments, the peptide may have a desirable biochemical activity that it may perform after cleavage of the peptide from the compound by a protease in a tumor. In one embodiment, the peptide may have an anti-tumor activity. For example, the peptide may be cyclic arginylglycylaspartic acid (RGD). Peptides with anti-tumor activities are known and their inclusion into the compound may be performed as a routine matter by the person of ordinary skill in the art having the benefit of the present disclosure.

Alternatively or in addition, the peptide may be linked, at a location other than the covalent bond from the peptide to the linker or the melanin precursor, with a therapeutic agent. In one embodiment, the therapeutic agent is not active until the peptide is cleaved by tumor protease. For one, non-limiting, example, a therapeutic agent may have a poor ability to enter cells when attached to the peptide-melanin precursor compound, but may have an improved ability to enter cells after the peptide is cleaved from the melanin precursor.

By "directly covalently bonded to" regarding the peptide and the melanin precursor is meant that the N-terminal nitrogen, the C-terminal carbon, or an atom on a side chain of an amino acid of the peptide is bonded to an atom of the melanin precursor. The atom of the melanin precursor may, but need not necessarily, be incorporated into the melanin. By "indirectly linked" regarding the melanin precursor and the peptide is meant that the N-terminal nitrogen, the C-terminal carbon, or an atom on a side chain of an amino acid of the peptide is bonded to a first atom of a linker moiety that is not the melanin precursor, and an atom of the melanin precursor is also bonded to a second atom of the linker moiety. Typically, but not necessarily, the first atom and the second atom are different atoms.

Any linker moiety known to the person of ordinary skill in the art as being suitable for use in compounds administered in vivo can be used. In one embodiment, the linker is capable of spontaneous disassembly from the melanin precursor after the peptide is removed.

In one embodiment, the indirect link comprises a p-hydroxybenzyl moiety. In another embodiment, the indirect link may comprise a 4-aminobenzoic acid (PABA) moiety.

Regardless of the type of link, wherein the direct covalent bond or indirect link of the peptide to the melanin precursor blocks spontaneous synthesis of the melanin in vivo in the absence of protease activity.

Protease activity, also known as peptidase activity, is an enzyme-catalyzed process by which peptide bonds are hydrolyzed. Typically, protease activity in healthy human and animal cells is sufficiently low that, in the event that the compound is introduced into such cells at reasonable concentrations, the rate of cleavage of the peptide-melanin precursor or peptide-linker bond is slower than the rate of spontaneous formation of a melanin from the melanin precursor, thereby allowing other naturally-occurring biochemical reactions to clear the melanin precursor from the cells before it can form a melanin. The "absence of protease activity" may be determined observationally simply from a lack of formation of pigment in cells to which the compound is introduced.

Many tumors, on the other hand, are characterized by significant protease activity within their cells. For example, MDA-MB-231 mammary carcinoma typically presents with high expression and secretion of cathepsin B and uPA, both of which are proteases. MDF7-TamR mammary carcinoma typically presents with high expression and secretion of uPA.

Accordingly, if the compound is introduced to cells of tumor characterized by significant protease activity, protease (s) cleave the peptide, leaving either the melanin precursor, which spontaneously forms a melanin in vivo, or the melanin precursor attached to a linker moiety. If the linker moiety is chosen to be a spontaneously-disassembling linker moiety (e.g., a p-hydroxybenzyl moiety), after disassembly of the linker moiety, a melanin precursor remains, which spontaneously forms a melanin in vivo.

Figure 2:
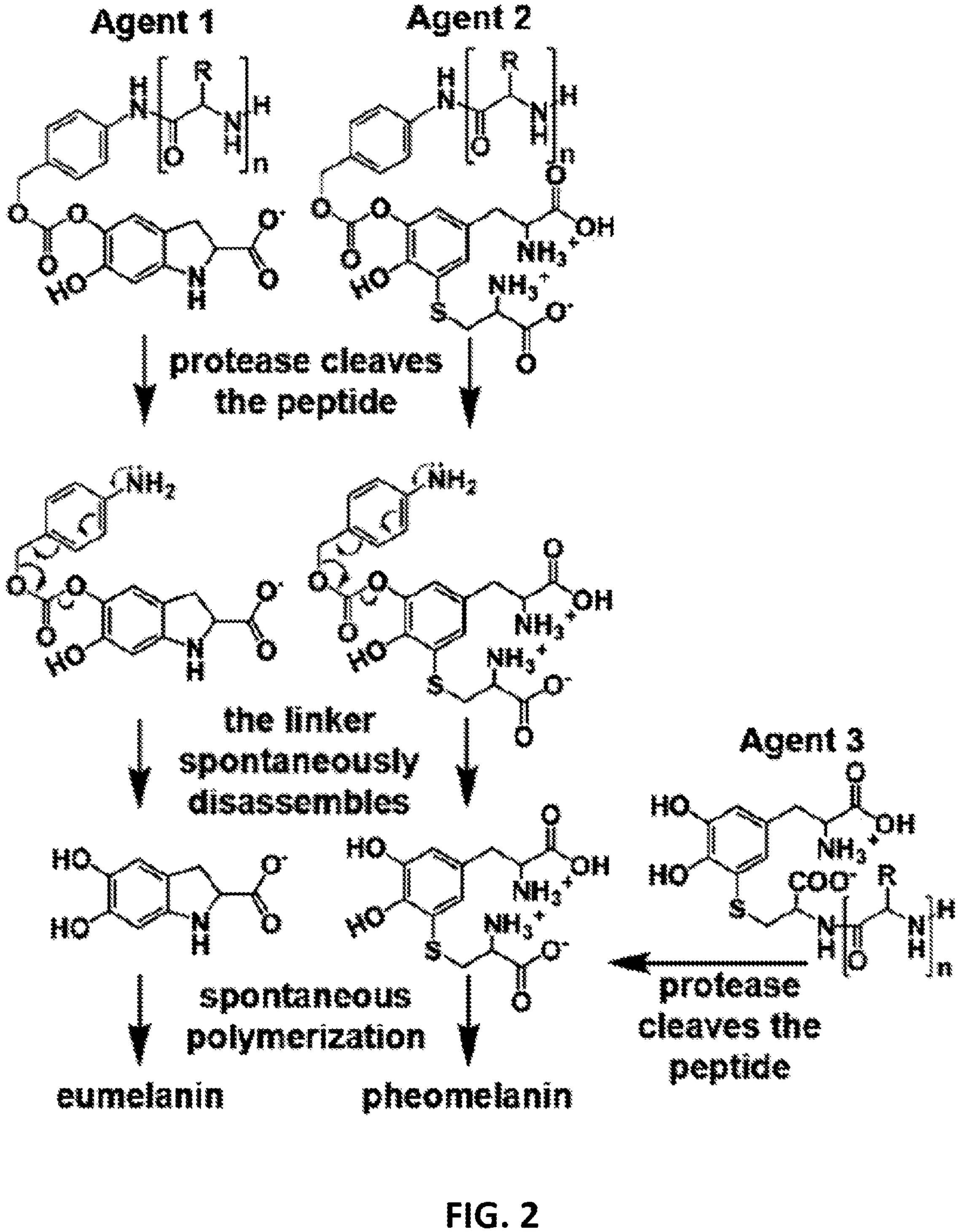
FIG. 2 schematically depicts biochemical reactions that lead from Agents 1-3 to formation of eumelanin and pheomelanin, in accordance with embodiments herein.

FIG. 2 schematically depicts biochemical reactions discussed above in more detail. Beginning with one of three compounds, Agents 1-3, tumor protease(s) cleave the peptide, leaving either a melanin precursor-linker moiety molecule (produced from Agents 1-2) or cysteinyldopa (produced from Agent 3). After the linker moiety spontaneously disassembles, it yields leucodopachrome or cysteinyldopa (derived from Agents 1 and 2, respectively). The leucodopachrome and cysteinyldopa derived from Agents 1-3 then spontaneously form eumelanin and pheomelanin, respectively, in vivo.

FIG. 10 supplements FIG. 2 by showing that leucodopachrome spontaneously decarboxylates as part of its spontaneous polymerization to yield eumelanin. Accordingly, the melanin precursor may be a decarboxylated leucodopachrome, such as the melanin precursor identified below as Agent 6.

In one embodiment, the compound is selected from the group consisting of Agent 1, Agent 2, Agent 3, and Agent 6:

Agent 1

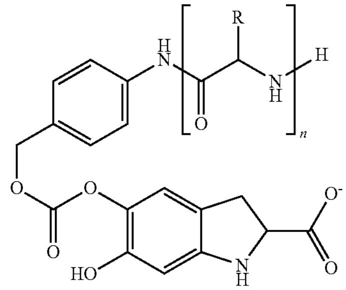

Agent 2

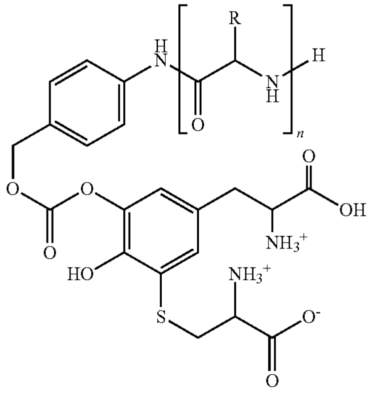

-continued

Agent 3

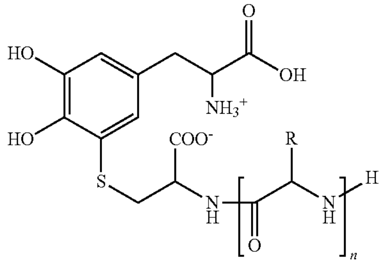

Agent 6

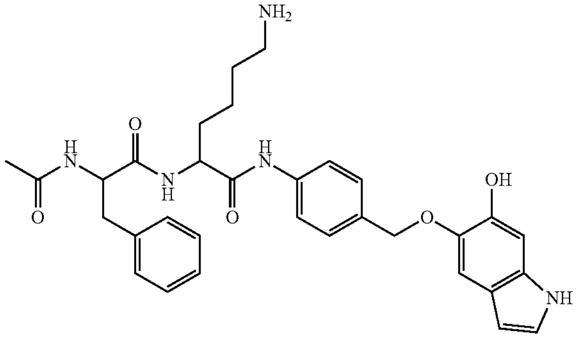

wherein n is greater than or equal to 1 and each R may be any organic moiety.

Agents 3 and 6 are exemplary compounds comprising the melanin precursor and the peptide. The person of ordinary skill in the art having the benefit of the present disclosure will be able to synthesize and use other molecules meeting the limitations of the disclosed compounds as a routine matter and would be in the spirit and scope of the embodiments disclosed herein.

Figure 3:
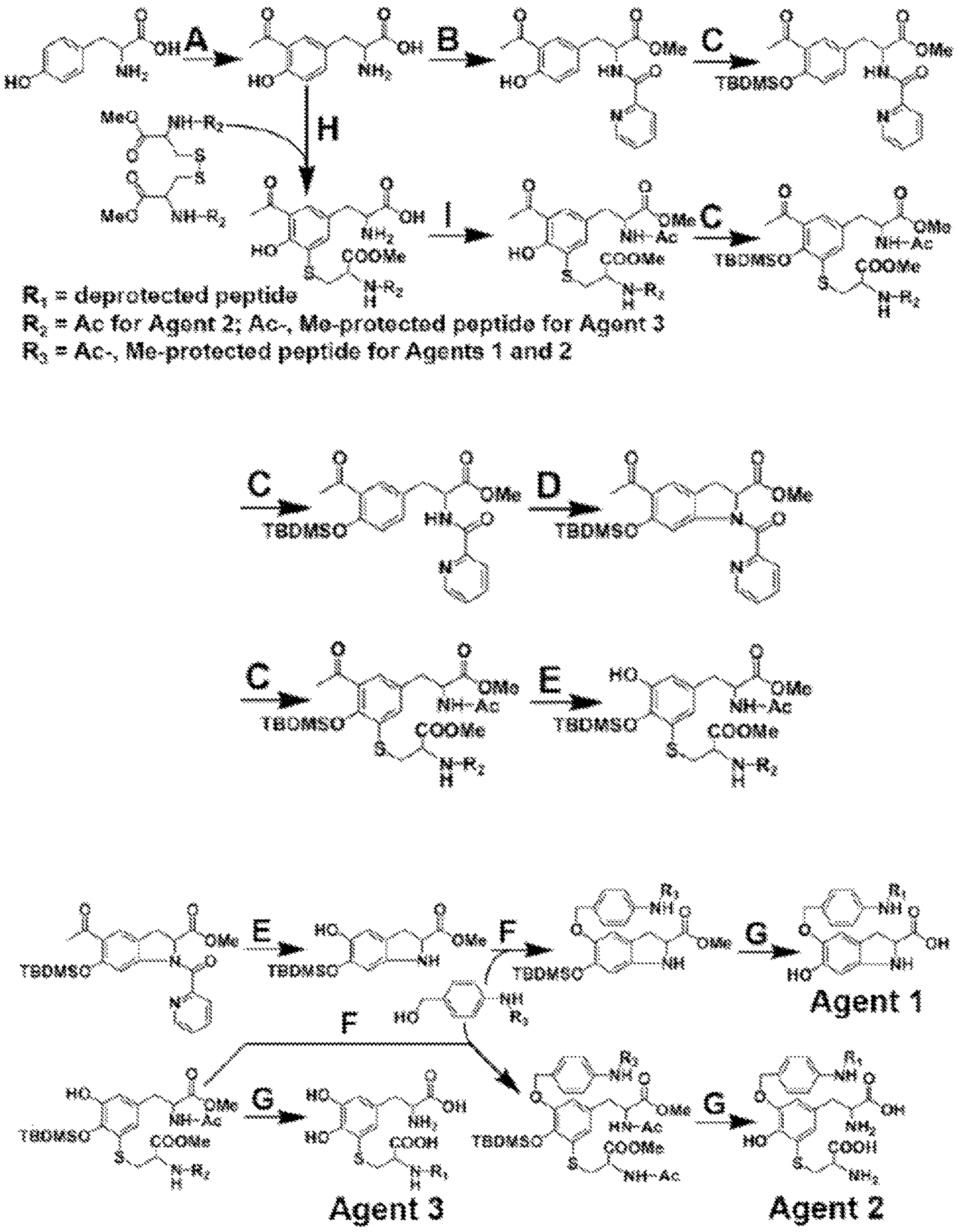
FIG. 3 schematically depicts an exemplary plan for synthesis of Agents 1-3, in accordance with embodiments herein.

The compound may be synthesized using any appropriate technique known to the person of ordinary skill in the art. FIG. 3 schematically depicts an exemplary and non-limiting plan for synthesis of Agents 1-3. Agent 1 can be synthesized using steps A-G. Agent 2 can be synthesized using steps A,H,I,C,E,F,G. Agent 3 can be synthesized using steps A,H,I,C,E,G. Agents that detect cathepsin B and urokinase plasminogen activator (uPA) can use HRYR and ASGK peptides. A protected peptide with a C-terminal hydroxybenzyl group is a reactant in step F, and a protected dipeptide with a disulfide bridge is a reactant in step H, which are synthesized using standard peptide synthesis methods.[95-106] All reactions are high yield, except step H. However, step H uses inexpensive reagents and is an initial step, so that a large amount can still be obtained from this step.

Reagents and reaction conditions for steps A-H can be as follows:

A) AcCl, $AlCl_3$, $PhNO_2$, 100° C.

B) $SOCl_2$, MeOH, 0° C. to r.t., then picolinic acid, EDC, HOBt, DIPEA, DCM

C) TBDMSCl, imidazole, DMF, r.t.

D) $Pd(OAc_2)$, $PhI(Ac_2O)$, toluene, 60° C., Ar

E) mCPBA, $CH_2Cl_2$, r.t., then $NH_3MeOH$, r.t.

F) $K_2CO_3$, NMP, r.t., then MsCl, DIPEA, NMP, −10° C. to r.t.

G) KOH, $H_2O$, MeOH, reflux

H) HBr, 100° C., 6 h

I) $SOCl_2$, MeOH, 0° C. to r.t., then $Ac_2O$, pyridine, r.t.

Figure 11:
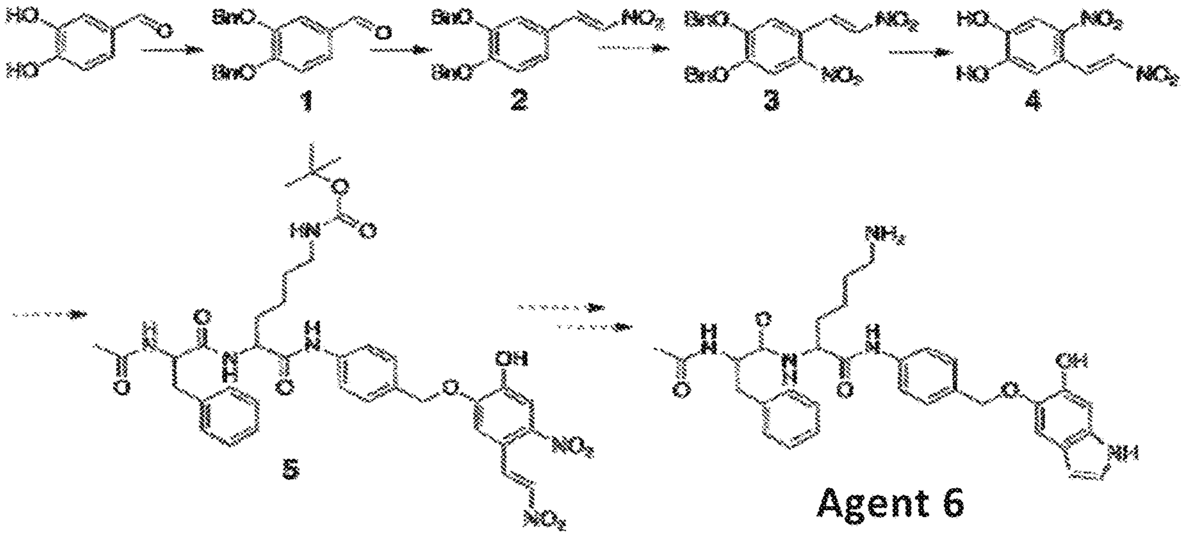
FIG. 11 schematically depicts an exemplary plan for synthesis of Agent 6, in accordance with embodiments herein.

FIG. 11 shows an exemplary and non-limiting synthesis scheme for the formation of Agent 6. Compound 1. 3,4- dihydroxyindole (200 mg, 1.45 mmol) was dissolved in dry DMF (4 mL), and potassium carbonate (800 mg, 5.79 mmol) and benzyl bromide (0.69 mL, 5.79 mmol) were added. The reaction was heated to 65° C. and stirred overnight. The solution was then diluted with ethyl acetate and washed with water then brine. The organic layer was dried over $MgSO_4$ and evaporated under reduced pressure. The resulting solid was purified by column chromatography over silica gel eluting with 20% ethyl acetate in hexanes to afford the desired product as a white solid (446 mg, 97% yield).

Compound 2. Compound 1 (524 mg, 1.65 mmol), nitromethane (0.53 mL, 9.88 mmol), ammonium acetate (508 mg, 6.58 mmol), and glacial acetic acid (6 mL) was combined, heated to reflux, and stirred for 1 hour. After cooling to room temperature, most of the acetic acid was removed under reduced pressure, and DCM was added. The solution was washed with a saturated solution of sodium carbonate followed by water. The organic layer was then dried over $MgSO_4$ and evaporated under reduced pressure. The resulting yellow solid was pure by TLC, so it was used without further purification (548 mg, 92% yield).

Compound 3. Compound 2 (548 mg, 1.52 mmol) was dissolved in glacial acetic acid (8 mL), and nitric acid (0.91 mL) was added dropwise. The reaction was heated to 40° C. and stirred for 2 hours. The reaction mixture was then poured into ice, and a precipitate formed. The solid was collected, dissolved in DCM, and washed with a saturated solution of sodium carbonate. The organic layer was then dried over $MgSO_4$ and evaporated under reduced pressure. The resulting solid was dissolved in a minimal amount of DCM, and methanol was added to crash out the desired product as a yellow solid (411 mg, 67% yield).

Compound 4. TFA (8 mL) was added to compound 3 (200 mg, 0.492 mmol), and the reaction mixture was heated to reflux for 3 hours. The solution was then cooled in an ice bath for 30 mins, and the solid was filtered out and washed with diethyl ether. The filtrate was evaporated under reduced pressure, and the resulting yellow solid was used without further purification (187 mg, quantitative yield).

Compound 5. Compound 4 (13 mg, 0.058 mmol) and Ac-Phe-Lys(Boc)-PABA (32 mg, 0.058 mmol) was dissolved in dry THF (1.5 mL) and cooled to −20° C. Triphenylphosphine (23 mg, 0.088 mmol) was added, and the reaction was stirred for 15 mins. DEAD (0.014 mL, 0.088 mmol) was then added dropwise and stirred for 1 hour at −20° C. before being allowed to warm to room temperature. After stirring overnight at room temperature, the reaction was diluted with ethyl acetate and washed with water followed by brine. The organic layer was dried over $MgSO_4$ and evaporated under reduced pressure. The resulting solid was purified by column chromatography over silica gel eluting with 5% methanol in DCM to afford the desired product as a white solid (18 mg, 78% yield).

Compound 6. Compound 5 (18 mg, 0.045 mmol) was dissolved in dry ethanol (1 mL). $ZnSO_4 \cdot H_2O$ (177 mg, 0.984 mmol) and $Na_2S_2O_4$ (321 mg, 1.845 mmol) were dissolved in de-gassed 0.1 M PBS, pH=4 (1 mL) and added to the solution of compound 5. The reaction mixture was heated to 50° C. and stirred for 3 hours. Most of the ethanol was then removed under reduced pressure and extracted with ethyl acetate three times. The organic layers were combined, dried over $MgSO_4$, and evaporated under reduced pressure. The resulting solid was purified by column chromatography over silica gel eluting with 20% ethyl acetate in hexanes to afford the desired product as a brown solid (14 mg, 68% yield).

In addition to the compound, the composition may further comprise one or more pharmaceutically-acceptable compounds, such as carriers (e.g., solvents, inert materials used in compounding tablets for oral ingestion, wall materials degradable in the patient's body for use in capsules for oral or other routes of administration), buffers, preservatives, adjuvants, surfactants, diluents (e.g. saline or dextrose) or the like. Such particular other compounds may be routinely selected by the person of ordinary skill in the art having the benefit of the present disclosure.

In one embodiment, the composition further comprises a pharmaceutically-acceptable carrier.

The composition may be formulated in a solid form, such as a soluble powder, a tablet, a caplet, or a capsule, among others; in a liquid form, such as a solution or slurry in an aqueous solvent, a hydrophilic solvent, or a hydrophobic solvent; or in an aerosol form, among others. The particular formulation and the concentration of the compound in the composition may be chosen by the person of ordinary skill in the art having the benefit of the present disclosure as a routine matter.

Figure 4:
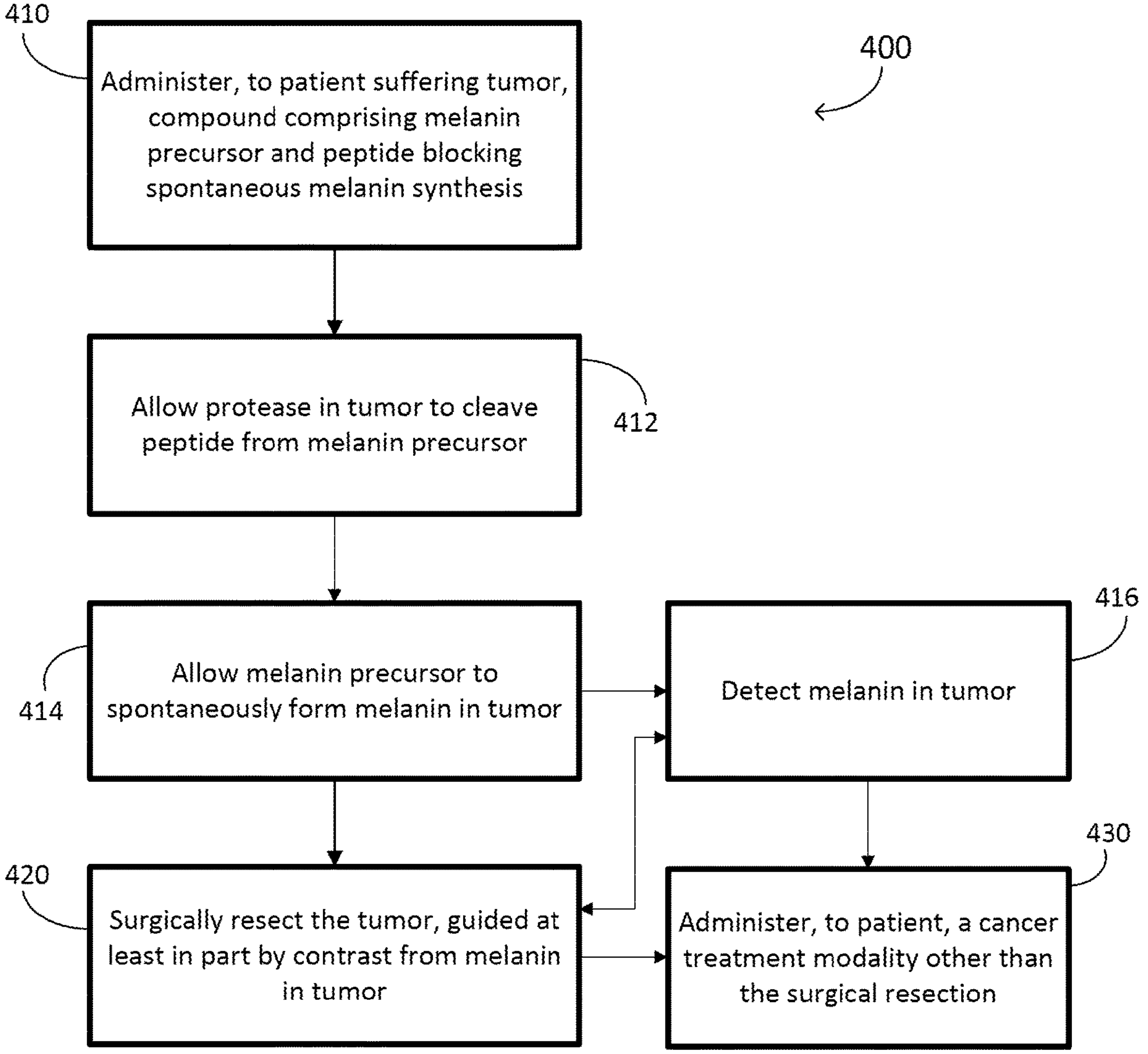
FIG. 4 presents a flowchart of a first method in accordance with embodiments herein.

Turning to FIG. 4, a flowchart of a method 400 in accordance with embodiments herein, is presented. The method 400 comprises administering (at 410), to a patient suffering from a tumor, a composition comprising a compound comprising a melanin precursor that spontaneously synthesizes a melanin when in free form in vivo. The composition also comprises a peptide directly covalently bonded to or indirectly linked to the melanin precursor, wherein the direct covalent bond or indirect link of the peptide to the melanin precursor blocks spontaneous synthesis of the melanin in vivo in the absence of protease activity.

The composition, the compound, the melanin precursor, the peptide, and the linker moiety providing the indirect linkage, if any, may be as described above.

The patient may be any mammal suffering from the cancer. In one embodiment, the patient is a human being.

In embodiments, the present method may be performed in a veterinary context. That is, the patient may be any non-human mammal suffering from a cancer. The non-human mammal may be a research animal, a pet, livestock, a working animal, a racing animal (e.g., a horse, a dog, a camel, etc.), an animal at stud (e.g., a bull, a retired racing stallion, etc.), or any other non-human mammal for which it is desired to treat its cancer.

For convenience, the description will typically refer to human patients. However, the person of ordinary skill in the art having the benefit of the present disclosure will readily be able to adapt the teachings of the present disclosure to a veterinary context.

By "suffering from a tumor" is meant that the tumor is detectable in the patient's body using any diagnostic technique presently known or to be discovered. The tumor may be benign, premalignant, or malignant. The tumor need not have been directly detected, e.g., a prostate cancer tumor may be detected from elevated levels of prostate-specific antigen in the patient's blood. "Suffering" does not require the patient to be in pain from or have any naturally-perceptible symptoms of the tumor. Generally, as is known, the earlier a tumor can be treated, including before the patient notices pain or any other symptoms, the greater the chances of remission.

The present method may be used to treat any tumor of any type of cancer. Desirably, the tumor is a solid tumor comprising cells that express high levels of protease. "High levels" as used herein refers to an increase in protease activity over the level prevailing in non-tumor tissue of the type from which the tumor originated. In one embodiment, the increase may be at least 75%. In another embodiment, the increase may be at least 50%. In yet another embodiment, the increase may be at least 25%. In still another embodiment, the increase may be at least 10%. Also desirably, the tumor is one that is known or reasonably expected, by the person of ordinary skill in the art having the benefit of the present disclosure, to be treatable by surgical resection or heat therapy.

Almost all malignant and metastatic tumors are expected to have upregulated extracellular proteases.[11,12] As a fundamental concept in tumor biology, a proteolytic cascade is required to degrade the extracellular matrix and cellular stroma to allow for tumor cell invasion (malignancy) and escape (metastasis). This fundamental concept has spurred the development of protease-activated fluorescent dyes for optical guided surgery Desirably, the tumor is of a cancer type and in an organ with essentially zero naturally-occurring melanin. Typically, melanins are only present at high concentrations in primary and metastatic melanoma, hair, and skin, and at low concentrations in brain and spine. We expect other types of tumors and tumors in other organs to be amenable to the methods disclosed herein.

In one embodiment, the tumor is of a cancer selected from the group consisting of breast cancer, head-and-neck cancer, pancreatic cancer, ovarian cancer, and thyroid cancer.

In one particular embodiment, the cancer is pancreatic cancer. In another embodiment, the cancer is head-and-neck cancer. In an embodiment, the cancer is breast cancer. In an additional embodiment, the cancer is ovarian cancer. In yet an additional embodiment, the cancer is thyroid cancer.

The composition may be administered 410 to the patient by any route and remain within the spirit and scope of the embodiments described herein. Such routes may be characterized as systemic or local. Systemic routes include oral, nasal, buccal, and intravenous injection routes, among others. Local routes include subcutaneous, intramuscular, intraorganal, and intratumoral injection, and catheterized and endoscopic routes, among others.

In one embodiment, administering 410 the composition comprises intravenous injection of the composition as an aqueous solution into the patient. Other systemic delivery techniques for administering 410 the composition are known to the person of ordinary skill in the art having the benefit of the present disclosure and may be selected by such person as a routine matter.

In the method 400, administering 410 the composition may be performed in a single dose or a plurality of doses. In one embodiment, a single dose is administered 410. The total dosage may provide the compound in a concentration from about 0.1 μmol/kg body weight to 1 mmol/kg body weight. In one embodiment, the total dosage may provide the compound in a concentration from about 0.5 μmol/kg body weight to 60 μmol/kg body weight.

The method 400 typically requires some time for the compound to be taken up by the tumor, followed by allowing (at 412) protease in the tumor to cleave the peptide from the melanin precursor or a compound containing the melanin precursor and a linker moiety, allowing the linker moiety (if present) to spontaneously disassemble, and allowing (at 414) the melanin precursor to spontaneously form melanin in the tumor. The total time required from administering 410 until a desirably high level of melanin has formed in the tumor may be from 0.1 hr to 72 hr. In one embodiment, the required time may be from about 0.25 hr to about 24 hr.

If desired, the method 400 may comprise detecting (at 416) the spontaneously-synthesized melanin in the tumor. The detecting (at 416) may be performed before, during, after, or in lieu of surgical resection (at 420), discussed below. The detecting (at 416) may comprise inspection by the naked eye or qualitative or quantitative, real-time or time-delayed, and/or still or video image observation by multispectral optoacoustic tomography (MSOT), also known as photoacoustic imaging (PAI).

The method 400 may further comprise surgically resecting (at 420) the tumor, wherein the surgical resection is guided at least in part by contrast imparted by the melanin, wherein the melanin is spontaneously synthesized in the tumor after administering the composition.

Figure 6:
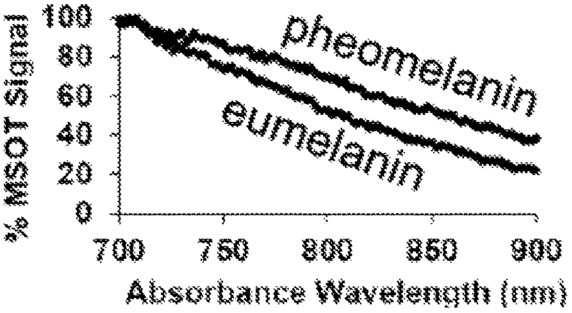
FIG. 6 reports multispectral optoacoustic tomography (MSOT), also known as photoacoustic imaging (PAI), spectra of eumelanin and pheomelanin, normalized to 100% signal at 700 nm, in accordance with embodiments herein.

The melanin may impart contrast in a number of ways. For example, melanins can be detected using MSOT/PAI. Both eumelanin and pheomelanin have strong signals across a broad spectral range that generates strong detection with MSOT (FIG. 6).

A small animal MSOT instrument (InVision) can rapidly acquire multispectral images of an entire mouse torso at 150 μm in-plane resolution and 1 mm slice thickness.[32,33] The strong laser of this instrument can image the entire transaxial≤3 cm diameter of the mouse torso, overcoming the limited depth of view of most other optoacoustic imaging instruments.

A clinical MSOT instrument can image tumors and other tissues, including in three dimensions. For example, the Acuity clinical MSOT instrument operates at a pulse repetition rate of 50 Hz to accommodate the movement of the transceiver wand. The RapidSCAN™ data acquisition system has 384 channels that can sample as fast as 40 MS/s. The three-dimensional (3D) detector covers a 180° angle with 384 detector elements to provide excellent sensitivity.

The laser for the clinical imaging system operates at ≤30 mJ with 4-10 nsec pulses to ensure clinical safety. These performance characteristics comply with ANSI Maximum Permissible Energy (MPE). The class 4 laser produces wavelengths from 680 to 980 nm in 1 nm increments, with almost-negligible<10 msec tuning at each wavelength.

The OPUS™ ultrasound imaging system has a broadband 2-8 MHz frequency range with synthetic aperture beamforming and spatial compounding. Prototypes for this system have shown sentinel lymph node detection in the clinic at 2 cm depth of field, and at a 5 cm depth of field with gentle pressing on the body, and with a very sensitive detection sensitivity of 4 cells with physiological melanin content. Melanin concentrations under 100 nM may be detectable by MSOT in vivo.

A depth of view of 3 cm has been shown to be sufficient to image patients with breast cancel[34-36] and other pathologies[37,38]. Moreover, MSOT is being developed for intrasurgical imaging. Our technology can be used to localize protease-active tumors as deep as 3 cm from tissue surfaces that are exposed during surgery, further improving surgical resection of tumors. "Digging" for tumors below the exposed tissue surface is one of the greatest problems with fluorescence guided surgery, which can be addressed with MSOT guided surgery.

Figure 7:
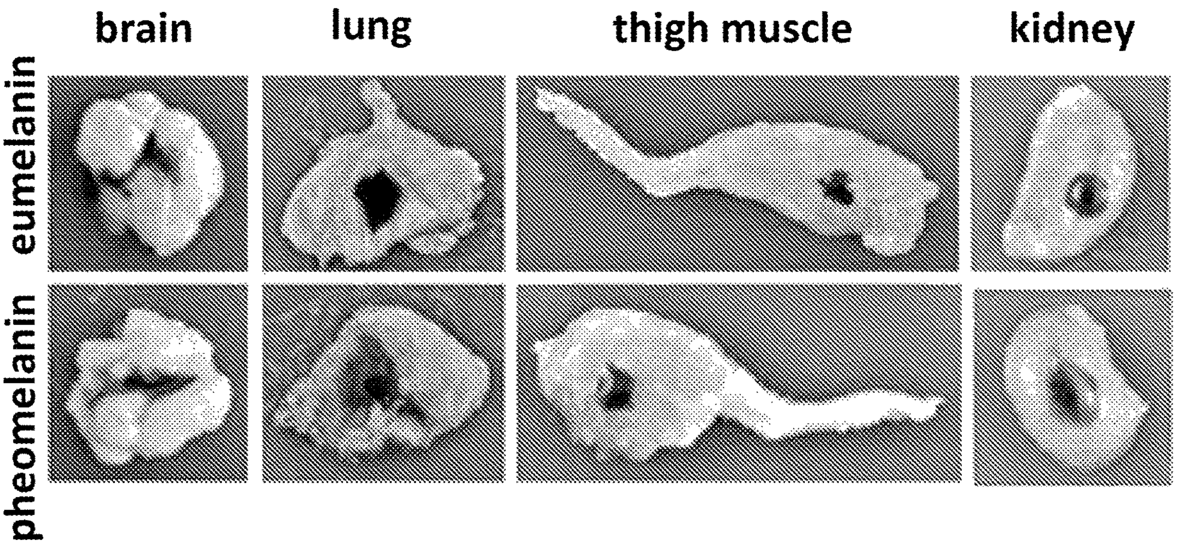
FIG. 7 shows models of melanins as contrast agents, in accordance with embodiments herein.

Another way melanin may impart contrast is by color in the visible spectrum of light. The administering 410 causes protease-active tumors to accumulate melanins and become black. Simple visual inspection without fluorescence imaging instrumentation can then detect these black tumors against the beige-to-red background of normal tissues. FIG. 7 presents images of mouse tissues on which were placed droplets (~1 μM) eumelanin or pheomelanin. FIG. 7 proves the concept that accumulation of melanins in tumors can provide optical contrast to the naked eye.

By use of MSOT, visual inspection, or both, a surgeon may be guided when surgically resecting 420 more easily and efficiently than by use of prior surgical imaging techniques, such as fluorescence. This guidance may allow the surgeon to remove more of the tumor without excessive removal of healthy tissues, and/or provide one or more other advantages.

As is known in the art, multiple treatment modalities are often used to increase the likelihood of remission of a cancer. Accordingly, in one embodiment, the method 400 may further comprise administering (at 430), to the patient, a cancer treatment modality other than the surgical resection. Administering 430 the cancer treatment modality other than the surgical resection may be targeted against the same cancer as the resected tumor, against metastases thereof, against a primary tumor or metastases of a tumor other than the surgically resected tumor, or two or more thereof.

A wide variety of cancer treatment modalities other than surgical resection are known to the person of ordinary skill in the art and need not be described in detail here. By way of example, in one embodiment, the cancer treatment modality other than the surgical resection is selected from the group consisting of radiation, chemotherapy, immunotherapy, checkpoint inhibitor therapy, oncolytic virus therapy, peptide therapy (e.g., cyclic RGD), thermal therapy (e.g., thermal ablation by the delivery and absorption of heat, light energy, radio frequency energy, and/or microwave energy, and/or cryotherapy), and two or more thereof.

Regardless of the particular cancer treatment modality other than surgical resection, if one or more is/are administered 430, the administering 430 may be performed before, after, or simultaneously with the surgically resecting 420. Particular relative and absolute timing of surgically resecting 420 and administering 430 the other cancer treatment modality will be a routine matter for the person of ordinary skill in the art having the benefit of the present disclosure.

Figure 5:
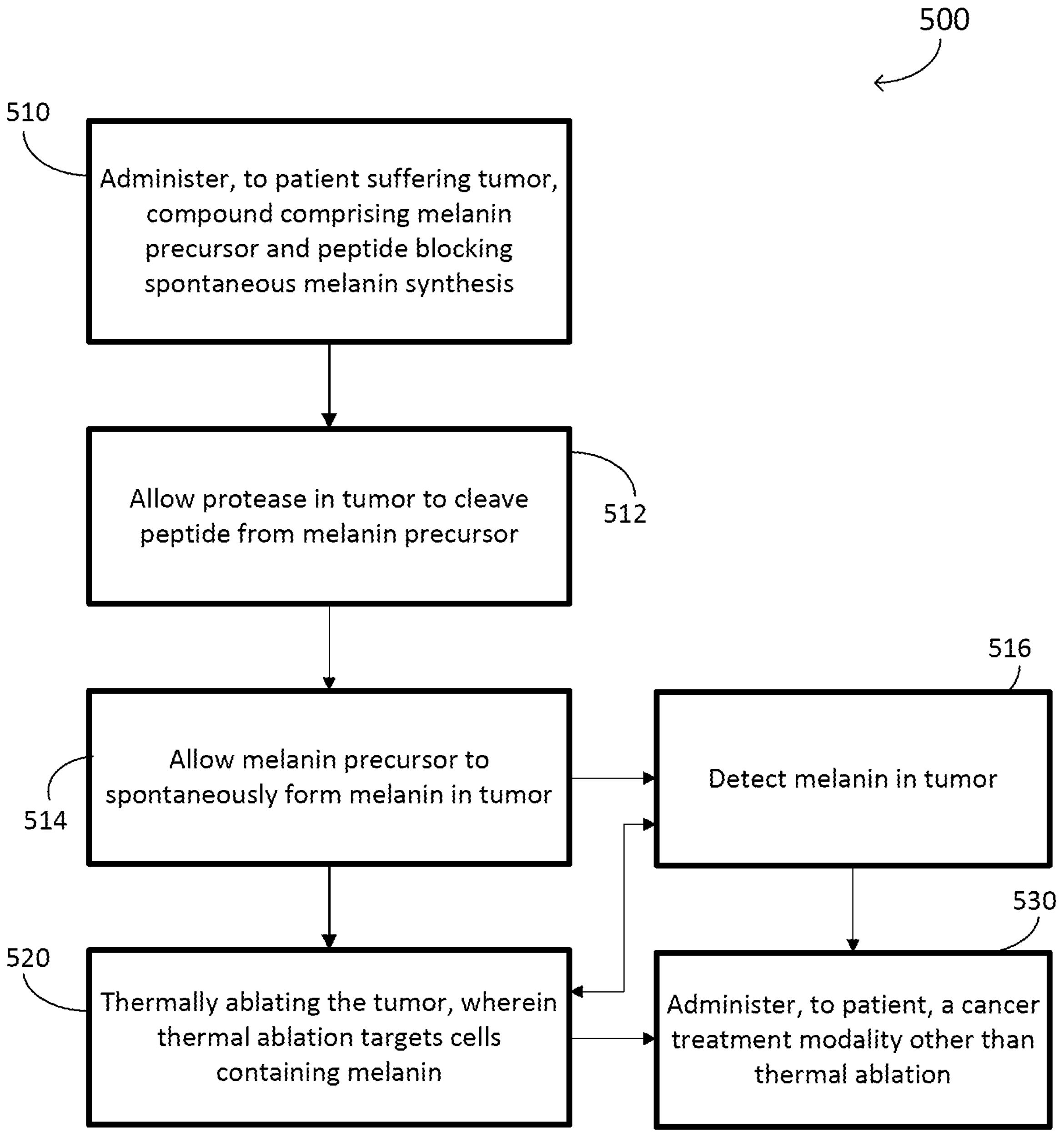
FIG. 5 presents a flowchart of a second method in accordance with embodiments herein.

FIG. 5 presents a flowchart of a method 500 in accordance with embodiments of the present disclosure. The method 500 comprises administering (at 510), to a patient suffering from a tumor, a composition comprising a compound comprising a melanin precursor that spontaneously synthesizes a melanin when in free form in vivo, and a peptide directly covalently bonded to or indirectly linked to the melanin precursor, wherein the direct covalent bond or indirect link of the peptide to the melanin precursor blocks spontaneous synthesis of the melanin in vivo in the absence of protease activity. Administering (at 510) may be performed essentially as administering (block 410) in the method 400 shown in FIG. 4 and need not be described further. Allowing (at 512) protease in the tumor to cleave the peptide, allowing (at 514) the precursor to spontaneously form melanin in the tumor, and detecting (at 516) melanin in the tumor may also be performed as described above regarding allowing (block 412), allowing (block 414), and detecting (block 416) in the method 400 shown in FIG. 4.

The method 500 also comprises thermally ablating (at 520) the tumor, wherein the thermal ablation targets cells containing melanin, wherein the melanin is spontaneously synthesized in the tumor after administering the composition. In one embodiment, the thermally ablating (at 520) comprises delivering energy, most commonly, light energy to the tumor after melanin has formed in the tumor. Though not to be bound by theory, the light energy is preferentially absorbed by the melanin, the light energy is then radiated as heat, and the radiated heat may kill or impair cells of the tumor. "Light energy" encompasses all infrared, visible, and ultraviolet wavelengths, and is not limited herein to light at visible wavelengths.

The amount and wavelength of light or other energy, the duration of delivery of the light or other energy, and other parameters of thermally ablating (at 520) the tumor, may be routinely selected by the person of ordinary skill in the art having the benefit of the present disclosure.

To thermally ablate (at 520), the energy may be delivered through the skin, if the tumor is at or near the skin. If the tumor is at or near a body structure through which an energy source may be introduced endoscopically, e.g., the nose, the mouth, the trachea, the bronchi, the gastrointestinal tract, the arterial vasculature, the urethra, or the vagina, the energy may be delivered endoscopically. If the tumor is not in proximity to the skin or a body structure amenable to endoscopy, or if intervening structures preclude delivery of energy through the skin, the thermally ablating (at 520) may be performed after exposing the tumor to the ambient environment, typically by surgery.

The method 500 may, in embodiments, further comprise administering 530, to the patient, a cancer treatment modality other than the thermal ablation. Examples of such cancer treatment modalities were discussed with reference to administering 430 in method 400 shown in FIG. 4 and surgically resecting 420 in method 400.

Specifically, in one embodiment of administering 530, the cancer treatment modality other than the thermal ablation is selected from the group consisting of radiation therapy, chemotherapy, immunotherapy, checkpoint inhibitor therapy, oncolytic virus therapy, peptide therapy, cryotherapy, RFA, microwave ablation, surgical resection, and two or more thereof.

In one embodiment, the methods 400 and 500 may be co-performed, i.e., the administering 430 in method 400 may comprise thermal ablation 520, and/or administering 530 in method 500 may comprise surgically resecting 420 the tumor. The combination of surgically resecting 420 and thermally ablating 520 may further increase the chances of remission: thermally ablating 520 might kill tumor cells that happen to elude the surgeon's perception when she or he surgically resects 420 the tumor, and surgical resection 420 might remove the main body of tumors that are too large for thermal ablation 520 to kill in a single procedure.

Figure 9:
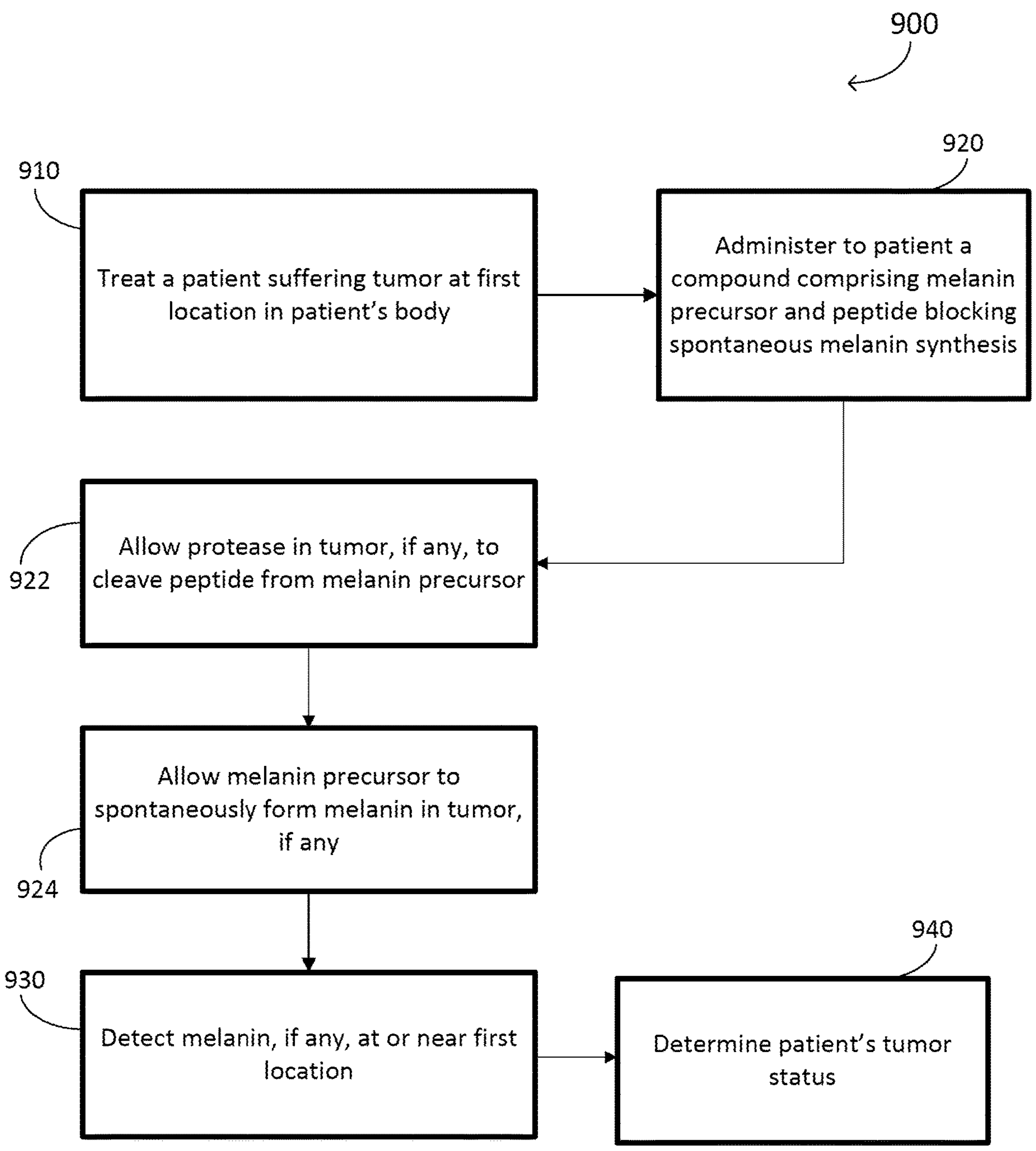
FIG. 9 presents a flowchart of a fourth method in accordance with embodiments herein.

Turning to FIG. 9, in one embodiment, the present disclosure relates to a method 900. The method 900 comprises treating (at 910) a patient suffering from a tumor at a first location in the patient's body. Treating (at 910) may be by any known technique, including, but not necessarily limited to, radiation therapy, chemotherapy, immunotherapy, checkpoint inhibitor therapy, oncolytic virus therapy, peptide therapy, cryotherapy, RFA, microwave ablation, thermal ablation, surgical resection, and two or more thereof. The treating (at 910) may include surgical resection guided by contrast imparted by compositions and methods of the present disclosure and/or thermal ablation along the lines of the methods of the present disclosure.

The method 900 further comprises administering (at 920), to the patient, a composition comprising a compound comprising a melanin precursor that spontaneously synthesizes a melanin when in free form in vivo. The composition also comprises a peptide directly covalently bonded to or indirectly linked to the melanin precursor, wherein the direct covalent bond or indirect link of the peptide to the melanin precursor blocks spontaneous synthesis of the melanin in vivo in the absence of protease activity.

Administering (at 920) may be performed using any techniques described above. The composition administered (at 920) may be as described above.

After administering (at 920), the fate of the composition will vary depending on the outcome of treating (at 910). If treating (at 910) were fully successful, and the tumor disappeared, then normal tissues at the first location in the patient's body, which are expected to lack protease activity, would not cleave the peptide from the melanin precursor, and the melanin precursor would substantially be prevented from forming melanin. If treating (at 910) were partially successful, and the tumor reduced in size, then the tumor would be expected to produce melanin after tumor proteases cleave the peptide from the melanin precursor (at 922) and the melanin precursor spontaneously forms melanin (at 924). If treating (at 910) were unsuccessful, and the tumor increased in size, then the tumor would also be expected to produce melanin.

Accordingly, the method 900 further comprises detecting (at 930) melanin at or near the first location. The detection (at 930) may be the naked eye, or may be by use of an optical imaging apparatus, such as MSOT equipment as discussed above. The detection may be qualitative or quantitative, with the latter potentially including measuring or calculating the size or volume of the tumor and/or the absorption intensity of the melanin spontaneously synthesized in the tumor.

The method 900 also comprises determining (at 940) the patient's tumor status in response to the detecting (at 930). Determining (at 940) may, but need not, comprise comparing the results of the detecting (at 930) with a baseline detection that may have been provided by administering similarly to the administering (at 920) and detecting similarly to the detecting (at 930) prior to the treating (at 910).

To continue the qualitative examples presented above, if treating (at 910) were fully successful, then detecting (at 930) would be expected to detect essentially zero melanin at the first location in the patient's body, and determining (at 930) may involve indicating, to the physician and/or the patient, that the tumor has essentially disappeared. If treating (at 910) were partially successful, then detecting (at 930) would be expected to detect the new, reduced size of the tumor, and determining (at 930) may involve indicating, to the physician, the size reduction in qualitative or quantitative terms, from which the physician may apply his or her skill to determine whether the treatment performed (at 910) should be repeated, modified, continued, discontinued, or replaced by another treatment of the same or different modality. If treating (at 910) were unsuccessful, then detecting (at 930) would be expected to detect the tumor's unchanged or increased size, and determining (at 930) may involve indicating, to the physician, the size increase in qualitative or quantitative terms, from which the physician may apply his or her skill to determine whether the treatment performed (at 910) should be repeated, modified, continued, discontinued, or replaced by another treatment of the same or different modality, or if palliative or hospice care is in the patient's best interest.

Determining (at 940) may be automated, particularly if the detecting (at 930) yields quantifiable data relating to tumor size, tumor volume, and/or melanin absorption intensity (which is reasonably expected to be indicative of protease activity) and/or if a baseline detection was performed prior to treating (at 910). Automated determination may enhance reproducibility and consistency of tumor status determinations and may allow use of data sets and algorithms that, if used by a person mentally or with the aid of pen and paper, would be prohibitive of time and attention, possibly even requiring months or years to calculate, thereby rendering the results of such hypothetical manual determination out-of-date and not clinically useful.

In another embodiment, the present disclosure relates to a method, comprising: administering, to a patient suffering from a tumor, a composition as referred to above; and detecting the tumor with noninvasive imaging.

In this embodiment, the administering may be as describe above, and will be expected to lead to significant amounts of melanin formation in tumors relative to healthy tissue.

Depending on the location of the tumor, detecting with noninvasive imaging may comprise visual inspection of the patient's skin, visual inspection through an endoscopic device introduced into the patient's body, or MSOT, among other techniques known in the art or to be developed.

By detecting the tumor with noninvasive imaging, the tumor may be diagnosed and/or monitored with greater accuracy, greater speed, and/or less patient discomfort. Detecting the tumor with noninvasive imaging may allow the physician to better plan a surgical resection of the tumor.

In one embodiment, the present disclosure relates to a "kit," wherein the kit comprising a composition as described above; and instructions for use of the composition in a method comprising administering, to a patient suffering from a tumor, the composition; and surgically resecting and/or thermally ablating the tumor, wherein the surgical resection is guided at least in part by optical contrast imparted by, or the thermal ablation targets cells containing, melanin spontaneously synthesized by the tumor after administering the composition.

A "kit," as used herein, refers to a package containing the composition, and instructions of any form that are provided in connection with the composition in a manner such that a clinical professional will clearly recognize that the instructions are to be associated with the composition.

"Instructions" typically involve written text or graphics on or associated with packaging of compositions of the disclosure. Instructions also can include any oral or electronic instructions provided in any manner. Written text or graphics may include a website URL or a QR code encoding a website URL, where other instructions or supplemental information may be provided in electronic form.

The kit may contain one or more containers, which can contain the composition or a component thereof. The kits also may contain instructions for mixing, diluting, or administering the composition. The kits also can include other containers with one or more solvents, surfactants, preservatives, and/or diluents (e.g., normal saline (0.9% NaCl), or 5% dextrose) as well as containers for mixing, diluting, or administering the composition to the patient in need of such treatment.

The composition may be provided in any suitable form, for example, as a liquid solution or as a dried material. When the composition provided is a dry material, the material may be reconstituted by the addition of solvent, which may also be provided by the kit. In embodiments where liquid forms of the composition are used, the liquid form may be concentrated or ready to use.

The kit, in one embodiment, may comprise a carrier being compartmentalized to receive in close confinement one or more containers such as vials, tubes, and the like.

The composition is described above.

The methods are as described above.

In one embodiment, the present disclosure relates to a composition, comprising: a compound, comprising: a melanin precursor that spontaneously synthesizes a melanin when in free form in vivo, a linker moiety covalently bonded to the melanin precursor, and a carbohydrate covalently bonded to the linker moiety, wherein the indirect link of the carbohydrate to the melanin precursor blocks spontaneous synthesis of the melanin in vivo in the absence of hydrolase activity.

The melanin precursor and the linker moiety may be as described above.

By "carbohydrate" is meant any compound from the group consisting of monosaccharides, disaccharides, oligosaccharides, and polysaccharides. Desirably, the carbohydrate may be chosen to be a substrate of a particular hydrolase enzyme as described below.

In one embodiment, the compound is selected from the group consisting of Agent 4:

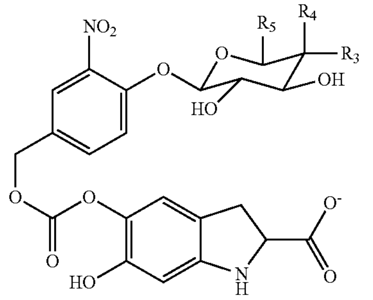

and Agent 5:

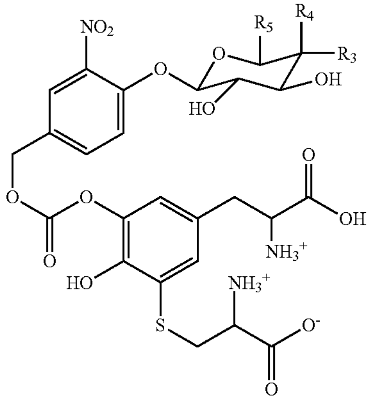

In Agents 4-5, $R_3$, $R_4$, and $R_5$ may independently be any organic moiety. In one embodiment, $R_3$ is —H, $R_4$ is —OH, and $R_5$ is —$CH_3OH$. In another embodiment, $R_3$ is —OH, $R_4$ is —H, and $R_5$ is —$COO^-$.

Figure 8:
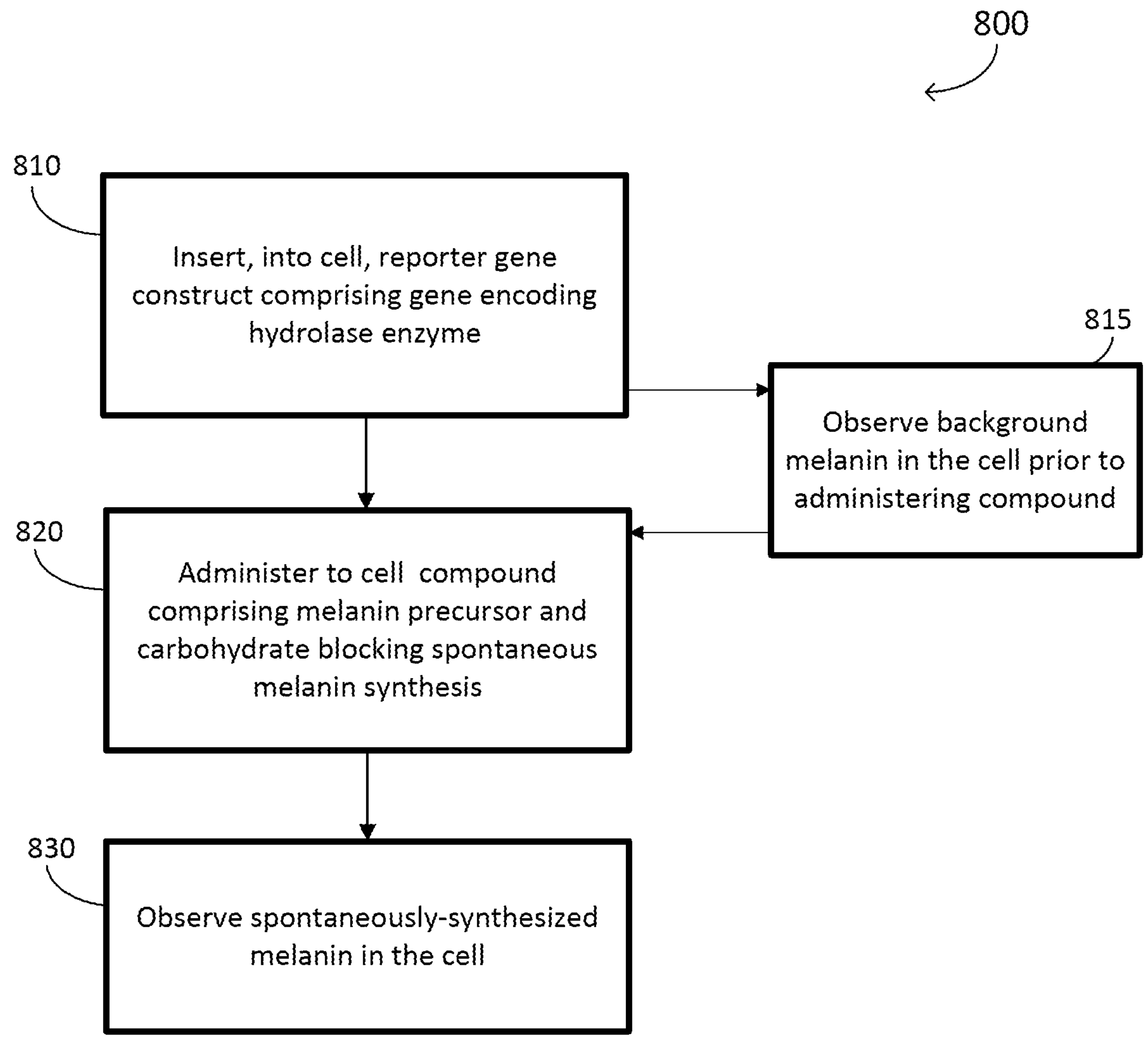
FIG. 8 presents a flowchart of a third method in accordance with embodiments herein.

FIG. 8 presents a flowchart of a method 800 in accordance with embodiments of the present disclosure. The method 800 comprises inserting (at 810), into at least one cell of an organism, a reporter gene construct comprising a regulatory sequence of interest and a coding sequence for a hydrolase enzyme.

Reporter gene constructs are well known in the molecular biology arts. Typically, the reporter gene construct is a portion of a DNA molecule comprising the regulatory sequence, e.g., the promoter, of a gene of interest for which it is desired to investigate the expression in a cell of interest under one or more conditions. The coding sequence for the hydrolase enzyme may be introduced into the DNA molecule at a location and orientation under control of the regulatory sequence of interest using techniques that are long established in the molecular biology arts and need not be described in detail.

The DNA molecule may also comprise one or more other coding sequences under the control of one or more other regulatory sequences. Such other coding sequences may assist in the handling, processing, transfection, genomic incorporation, or the like of the DNA molecule and/or the reporter gene construct.

The DNA molecule may be selected as a routine matter for many organisms. The cell may be a prokaryotic cell, a cell of a single-celled eukaryote, a plant cell, an animal cell, or a human cell, among others. Reporter gene constructs may be used in cells in vitro or in vivo.

Inserting 810 may comprise any techniques known to the person of ordinary skill in the art and need not be described in detail.

In one embodiment, the coding sequence for the hydrolase enzyme encodes a hydrolase enzyme selected from the group consisting of β-galactosidase (β-gal) and β-glucuronidase (β-gus).

The method 800 also comprises administering (at 820), to the cell, a composition comprising a compound comprising a melanin precursor that spontaneously synthesizes a melanin when in free form in vivo, a linker moiety covalently bonded to the melanin precursor, and a carbohydrate covalently bonded to the linker moiety, wherein the indirect link of the carbohydrate to the melanin precursor blocks spontaneous synthesis of the melanin in vivo in the absence of hydrolase activity.

The composition may be as described above. In embodiments wherein the hydrolase enzyme is β-gal, the compound may be selected from the group consisting of Agents 4-5, wherein $R_3$ is —H, $R_4$ is —OH, and $R_5$ is —$CH_3OH$. In embodiments wherein the hydrolase enzyme is β-gus, the compound may be selected from the group consisting of Agents 4-5, wherein, $R_3$ is —OH, $R_4$ is —H, and $R_5$ is —$COO^-$.

Administering 820 to the cell may be directly to the cell or a culture medium containing the cell, if the method 800 is performed in vitro, or locally or systemically to an organism of which the cell is a part, if performed in vivo.

After the composition is administered 820, the compound may enter the cell or come in contact with one or more proteins on the cell surface. Though not to be bound by theory, hydrolase enzyme expressed by the reporter gene construct, either constitutively or as induced by one or more conditions, is expected to cleave the carbohydrate from the compound. The linker moiety is then expected to spontaneously disassemble, yielding the melanin precursor, which then is expected to spontaneously polymerize to form the melanin. If the hydrolase enzyme is not significantly expressed, the cleavage of the carbohydrate is not expected, and melanin will not be formed spontaneously from the melanin precursor. Accordingly, the accumulation or lack thereof of melanin in the cell indicates whether the regulatory sequence of interest is active or not active in the cell under the condition(s) tested by the experiment.

The method 800 also comprises observing (at 830) melanin in the cell, wherein the melanin is spontaneously synthesized in the cell after administering the composition. Observation 830 may be by any appropriate technique. In one embodiment, observation is by MSOT.

Observing 830 melanin in the cell does not imply that only one cell may be the subject of the method 800. A plurality of cells and/or a portion or the entirety of a multicellular organism may be the subject of the method 800.

In one embodiment, the method 800 may further comprise observing (at 815), prior to administering 820 the compound, melanin in the cell, wherein the melanin so observed is that which naturally occurs in the cell. Desirably, the observing 815 uses the same technique that is used in observing 830.

In this embodiment of the method 800, the observing 830 may comprise processing the data generated by observing 830 in view of the data generated by observing 815. This may comprise aligning images taken from observing 815 and observing 830 and subtracting the intensity of a pixel from the data generated by the observing 815 from the intensity of the corresponding pixel from the data generated by the observing 830, among other processing techniques that will be apparent to the person of ordinary skill in the art having the benefit of the present disclosure.

In one embodiment, the present disclosure relates to a kit, comprising a compound comprising a melanin precursor, a linker moiety, and a carbohydrate, and instructions for performing the method 800.

EXAMPLES

Example 1

We incubated 2.22 mg/mL (5 μmol, 0.1 mL) of Agent 6 with 2 units of cathepsin B at pH 6.8 and at 37° C. overnight. Although cathepsin B is typically considered to be an endoprotease, this enzyme can work as an exoprotease at lower pH relative to physiological pH 7.4. Also, the extracellular tumor microenvironment is known to be acidic, so that pH 6.8 is a better representation of tumor conditions. The resulting solution was a light gray color, indicating that the reaction product contained melanin that was produced after Agent 6 was cleaved by the cathepsin B protease.

Other samples of were prepared at 1.66, 1.11, 0.84, and 0.55 mg/mL. These solutions were inserted into a customized phantom for a multi spectral optoacoustic imaging instrument (MSOT; also known as photoacoustic imaging) (InVision instrument, iThera Medical). FIG. 12A-FIG. 12D present MSOT or absorbance spectra data for the various concentrations.

Figures 12A, 12B, 12C, 12D:
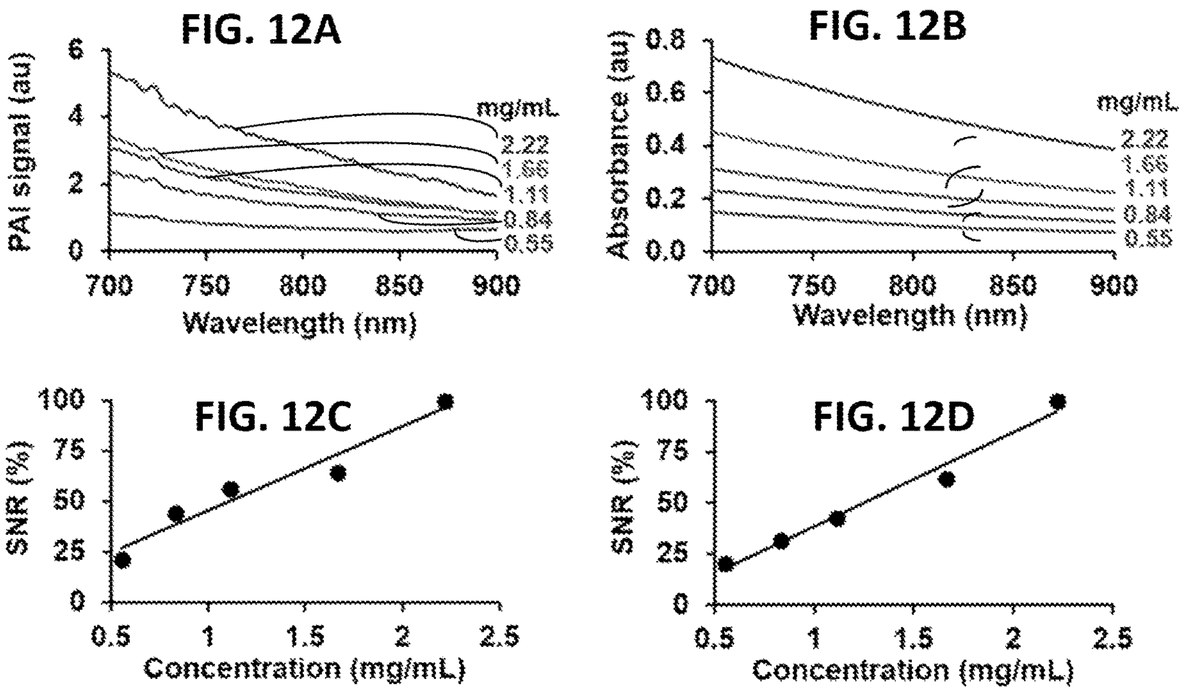
FIG. 12A presents multispectral optoacoustic (MSOT) imaging spectra of various concentrations of Agent 6 incubated with cathepsin B, as described in Example 1.
FIG. 12B presents absorbance spectra of the various concentrations of Agent 6 incubated with cathepsin B, as described in Example 1.
FIG. 12C presents MSOT signal-to-noise (SNR) ratios for the various concentrations of Agent 6, as described in Example 1.
FIG. 12D presents absorbance signal-to-noise (SNR) ratios for the various concentrations of Agent 6, as described in Example 1.

The phantoms were imaged at 700-900 nm absorbance wavelengths in 2 nm steps. (FIG. 12A). The samples were also analyzed with a spectrofluorometer with absorbance through the same wavelength range (FIG. 12B), which matched the spectral profile and relative signal intensities of the MSOT spectra. The spectra were broad and featureless, which is expected for a melanin-based product. The signal to noise ratio (SNR) scaled with the concentration of the reactant, providing validation that the MSOT and absorbance signals were derived from the product and was not an artifact of the solution or imaging instrument (FIG. 12C, FIG. 12D).

Therefore, these preliminary results indicate that Agent 6 is cleaved by cathepsin B to create a melanin-based product that can be detected by MSOT.

REFERENCES

Detection of Protease Activity

1. Mason H S. A classification of melanins. Ann New York Acad Sci 1948; 4:399-404. PMID: 18862181, no PMCID, no DOI.
2. del Marmol V, Beermann F. Tyrosinase and related proteins in mammalian pigmentation. FEBS Lett 1996; 382:165-168. PMID: 8601447, no PMCID, no DOI.
3. Grootendorst D J, Jose J, Wouters M W, van Boven H, Van der Hage J, Van Leeuwen D G, Steenbergen W, Manohar S, Ruers T J M. First experiences of photoacoustic imaging for detection of melanoma metastases in resected human lymph nodes. Lasers Surg Med 2012; 44:541-549. PMID: 22886491, no PMCID, DOI: 10.1002/1sm.22058
4. Zhou Y, Li G, Zhu L, Li C, Cornelius L A, Wang L V. Handheld photoacoustic probe to detect both melanoma depth and volume at high speed in vivo. J Biophotonics 2015; 8:961-967. PMID: 25676898, PMCID: PMC4530093, DOI: 10.1002/jbio.201400143
5. Stoffels I, Morscher S, Helfrich I, Hillen U, Leyh J, Burton N C, Sardella T C P, Claussen J, Poeppel T D, Bachmann H S, Roesch A, Briewank K, Schadendorf D, Gunzer M, Klode J. Metastatic status of sentinel lymph nodes in melanoma determined noninvasively with multispectral optoacoustic imaging. Sci Trans Med 2015; 7:317ra199. PMID: 26659573, no PMCID, DOI: 10.1126/scitranslmed.aad1278
6. Schwarz M, Buehler A, Aguirre J, Ntziachristos V. Three-dimensional multispectral optoacoustic mesoscopy reveals melanin and blood oxygenation in human skin in vivo. J Biophotonics 2016; 9:55-60. PMID: 26530688, no PMCID, DOI: 10.1002/jbio.201500247
7. Lavaud J, Henry M, Coll J L, Josserand V. Exploration of melanoma metastases in mice brains using endogenous contrast photoacoustic imaging. Int J Pharmaceutics 2017; 532:704-709. PMID: 28847669, no PMCID, DOI: 10.1016/j.ijpharm.2017.08.104
8. Shah A, Delgado-Goni T, Casals Galobart T, Wantuch S, Jamin Y, Leach M O, Robinson S P, Bamber J, Beloueche-Babari M. Detecting human melanoma cell re-differentiation following BRAF or heat shock protein 90 inhibition using photoacoustic and magnetic resonance imaging. Sci Rep 2017; 7:8215. PMID: 28811486, PMCID: PMC5557970, DOI: 10.1038/s41598-017-07864-8
9. Aggarwal N, Sloane B F. Cathepsin B: Multiple roles in cancer. Proteomics Clin App 2014; 8:427-437. PMID: 24677670, PMCID: PMC4205946, DOI: 10.1002/prca.201300105
10. Stantibanez J F. Urokinase type plasminogen activator and the molecular mechanisms of its regulation in cancer. Protein Pept Lett 2017; 24:936-946. PMID: 28820062, no PMCID, DOI: 10.2174/0929866524666170818161132
11. Mason S D, Joyce J A. Proteolytic networks in cancer. Trends Cell Biol 2011; 21:228-237. PMID: 21232958, PMCID: PMC3840715, DOI: 10.1016/j.tcb.2010.12.002
12. McIntyre J O, Matrisian L M. Molecular imaging of proteolytic activity in cancer. J Cell Biochem 2003; 90:1087-1097. PMID: 14635184, no PMCID, DOI: 10.1002/jcb.10713
13. Illy C, Quraishi O, Wang J, Purisima E, Vernet T, Mort J S. Role of the occluding loop in cathepsin B activity. J Biol Chem 1997; 272:1197-1202. PMID: 8995421, no PMCID, no DOI
14. Choe Y, Leonetti F, Greenbaum D C, Lecaille F, Bogyo M, Bromme D, Ellman J A, Craik C S. Substrate profiling of cysteine proteases using a combinatorial peptide library identifies functionally unique specificities. J Biol Chem 2006; 281:12824-12832. PMID: 16520377, no PMCID, DOI: 10.1074/jbc.M513331200
15. Gosalia D N, Salisbury C M, Maly D J, Ellman J A, Diamond S L. Profiling serine protease substrate specificity with solution phase fluorogenic peptide microarrays. Proteomics 2005; 5:1292-1298. PMID: 15742319, no PMCID, DOI: 10.1002/pmic.200401011
16. Harris J L, Backes B J, Leonetti F, Mahrus S, Ellman J A, Craik C S. Rapid and general profiling of protease specificity by using combinatorial fluorogenic substrate libraries. Proc Nat Acad Sci USA 2000; 97:7754-7759. PMID: 10869434, PMCID: PMC16617, DOI: 10.1073/pnas.140132697

17. Khersonsky O, Tawfik D S. Enzyme promiscuity: a mechanistic and evolutionary perspective. Ann Rev Biochem 2010; 79:471-505. PMID 20235827, no PMCID DOI: 10.1146/annurev-biochem-030409-143718

18. Whitley M J, Cardona D M, Lazarides A L, Spasojevic I, Ferrer J M, Cahill J, Chang-Lung Lee C L, Matija Snuderl M, Dan G. Blazer D G III, E. Shelley Hwang E S, Greenup R A, Mosca P J, Mito J K, Cuneo K C, Larrier N A, O'Reilly E K, Riedel R F, Eward W C, Strasfeld D B, Fukumura D, Jain R K, Lee W D, Griffith L G, Bawendi M G, Kirsch D G, Brigman B E. A mouse-human phase 1 co-clinical trial of a protease-activated fluorescent probe for imaging cancer. Sci Trans Med 2016; 8:320ra4. PMID: 26738797, PMCID: PMC4794335, DOI: 10.1126/scitranslmed.aad0293

19. Lazarides A L, Whitley M J, Strasfeld D B, Cardona D M, Ferrer J M, Mueller J L, Fu H L, DeWitt S B, Brigman B E, Ramanujam N, Kirsch D G, Eward W C. A fluorescence-guided laser ablation system for removal of residual cancer in a mouse model of soft tissue sarcoma. Theranostics 2016; 6:155-166. PMID: 26877775, PMCID: PMC4729765, DOI: 10.7150/thno.13536.

20. Sheth R A, Upadhyay R, Stangenberg L, Sheth R, Weissleder R, Mahmood U. Improved detection of ovarian cancer metastases by intraoperative quantitative fluorescence protease imaging in a pre-clinical model. Gynecol Oncology 2009; 112:616-622. PMID: 19135233, PMCID: PMC2664404, DOI: 10.1016/j.ygyno.2008.11.018

21. Nguyen Q T, Olson E S, Aguillera T A, Jiang T, Scadeng M, Ellies L G, Tsien R Y. Surgery with molecular fluorescence imaging using activatable cell-penetrating peptides decreases residual cancer and improves survival. Proc Nat Acad Sci USA. 2010; 107:4317-4322. PMID: 20160097, PMCID: PMC2840114, DOI: 10.1073/pnas.0910261107

22. Mieog J S D, Hutteman M, van der Vorst J R, Kuppen P J K, Que I, Dijkstra J, Kaijzel E L, Prins F, Lowik CWGM, Smit VTHBM, van de Velde C J H, Vahrmeijer Al. Image-guided tumor resection using real-time near-infrared fluorescence in a syngeneic rat model of primary breast cancer. Breast Cancer Res Treatment 2011; 128: 679-689. PMID: 20821347, no PMCID, DOI: 10.1007/s10549-010-1130-6

23. Mito J K, Ferrer J M, Brigman B E, Lee C L, Dodd R D, Eward W C, Marshall L F, Cuneo K C, Carter J E, Ramasunder S, Kim Y, Lee W D, Griffith L G, Bawendi M G, Kirsch D G. Interoperative detection and removal of microscopic residual sarcoma using wide-field imaging. Cancer 2012; 118:5320-5330. PMID: 22437667, PMCID: PMC3532657, DOI: 10.1002/cncr.27458

24. Eward W C, Mito J K, Eward C A, Carter J E, Ferrer J M, Kirsch D G, Brigman B E. A novel imaging system permits real-time in vivo tumor bed assessment after resection of naturally occurring sarcomas in dogs. Clin Orthopaedics Related Res 2013; 471:834-842. PMID: 22972654, PMCID: PMC3563778, DOI: 10.1007/s11999-012-2560-8

25. Blum G, von Degenfeld G, Merchant M J, Blau H M, Bogyo M. Noninvasive optical imaging of cysteine protease activity using fluorescently quenched activity-based probes. Nat Chem Biol 2007; 3:668-677. PMID: 17828252, no PMCID, DOI: 10.1038/nchembio.2007.26

26. Blum G, Weimer R M, Edgington L E, Adams W, Bogyo M. Comparative assessment of substrates and activity based probes as tools for non-invasive optical imaging of cysteine protease activity. PloS One. 2009; 4:e6374. PMID: 19636372, PMCID: PMC2712068, DOI: 10.1371/journal.pone.0006374

27. Olson E S, Jiang T, Aguilera T A, Nguyen Q T, Ellies L G, Scadeng M. Tsien R Y. Activatable cell penetrating peptides linked to nanoparticles as dual probes for in vivo fluorescence and MR imaging of proteases. Proc Natl Acad Sci USA 2010; 107:4311-6. PMID: 20160077, PMCID: PMC2840175, DOI: 10.1073/pnas.0910283107

28. Fujii T, Kamiya M, Urano Y. In vivo imaging of intraperitoneally disseminated tumors in model mice by using activatable fluorescent small-molecular probes for activity of cathepsins. Bioconj Chem 2014; 25:1838-1846. PMID: 25196809, no PMCID, DOI: 10.1021/bc5003289

29. Ofori L O, Withana N P, Prestwood T R, Verdoes M, Brady J J, Winslow M M, Sorger J, Bogyo M. Design of protease activated optical contrast agents that exploit a latent lysosomotropic effect for use in fluorescenceguided surgery. ACS Chem Biol 2015; 10:1977-1988. PMID: 26039341, PMCID: PMC4577961, DOI: 10.1021/acschembio.5b00205

30. DeWitt S B, Eward W C, Eward C A, Lazarides A L, Whitley M J, Ferrer J M, Brigman B E, Kirsch D G, Berg J. A novel imaging system distinguishes neoplastic from normal tissue during resection of soft tissue sarcomas and mast cell tumors in dogs. Veterinary Surg 2016; 45:715-722. PMID: 27281113, PMCID: PMC4970890, DOI: 10.1111/vsu.12487

31. Miampamba M, Liu J, Harootunian A, Gale A J, Baird S, Chen S L, Nguyen Q T, Tsien R Y, Gonzalez J E. Sensitive in vivo vlsualization of breast cancer using ratiometric protease-activatable fluorescent imaging agent, AVB-620. Theranostics 2017; 7:3369-3386. PMID: 28900516, PMCID: PMC5595138, DOI: 10.7150/thno.20678

32. Ntziachristos V, Razansky D. Molecular imaging by means of multispectral optoacoustic tomography (MSOT). Chem Rev 2010; 110:2783-2794. PMID: 20387910, no PMCID, DOI: 10.1021/cr9002566

33. Taruttis A, Ntziachristos V. Advances in real-time multispectral optoacoustic imaging and its applications. Nat Photon 2015; 9:219-227. No PMID, no PMCID, DOI: 10.1038/nphoton.2015.29

34. Diot G, Metz S, Noske A, Liapis E, Schroeder B, Ovsepian S V, Meier R, Rummeny E J, Ntziachristos V. Multi-spectral optoacoustic tomography (MSOT) of human breast cancer. Clin Cancer Res 2017; 23:6912-6922. PMID: 28899968, no PMCID, DOI: 10.1158/1078-0432.CCR-16-3200.

35. Becker A, MasthoffM, Claussen J, Ford S J, Roll W, Burg M, Barth P J, Heindel W, Schafers M, Eisenblatter M, Wildgruber M. Multispectral optoacoustic tomography of the human breast: characterization of healthy tissue and malignant lesions using a hybrid ultrasound-optoacoustic approach. Euro Radiol 2018; 28:602-609. PMID: 28786007, no PMCID, DOI: 10.1007/s00330-017-5002-x 36. Neuschler E I, Butler R, Young C A, Barke L D, Bertrand M L, Bohm-Velez M, Destounis S, Donlan P, Grobmyer S R, Katzen J, Kist K A, Lavin P T, Makariou E V, Parris $T_M$, Schilling K J, Tucker F L, Dogan B E. A pivotal study of optoacoustic imaging to diagnose benign and malignant breast masses: A new evaluation tool for radiologists.

Radiology 2017; 287:398-412. PMID: 29178816, no PMCID, DOI: 10.1148/radio1.2017172228

37. Waldner M J, Knieling F, Egger C, Morscher S, Claussen J, Vetter M, Kielisch C, Fischer S, Pfeifer L, Hagel A, Goertz R S, Wildner D, Atreya R, Strobel D, Neurath M F. Multispectral optoacoustic tomography in Crohn's disease: noninvasive imaging of disease activity. Gastroenterology 2016; 151:238-240. PMID: 27269244, no PMCID, DOI: 10.1053/j.gastro.2016.05.047

38. Knieling F, Neufert C, Hartmann A, Claussen J, Urich A, Egger C, Vetter M, Fischer S, Pfeifer L, Hagel A, Kielisch C, Görtz R S, Wildner D, Engel M, Röther J, Uter W, Siebler J, Atreya R, Rascher W, Strobel D, Neurath M F, Waldner M J. Multispectral optoacoustic tomography for assessment of Crohn's diease activity. N Engl J Med 2017; 376:1294-1296. PMID: 28355498, no PMCID, DOI: 10.1056/NEJMc1612455

39. He J, Yang L, Yi W, Fan W, Wen Y, Miao X, Xiong L. Combination of fluorescence-guided surgery with photodynamic therapy for the treatment of cancer. Mol Imaging 2017; 16:1536012117722911. PMID: 28849712, PMCID: PMC5580848, DOI: 10.1177/1536012117722911

40. Shimizu K, Nitta M, Komori T, Maruyama T, Yasuda T, Fujii Y, Masamune K, Kawamata T, Maehara T, Muragaki Y. Intraoperative photodynamic diagnosis using talaporfin sodium simultaneously applied for photodynamic therapy against malignant glioma: a prospective clinical study. Front Neurol 2018; 9:24. PMID: 29441040, PMCID: PMC5797572, DOI: 10.3389/fneur.2018.00024

41. Tsuda T, Kaibori M, Hishikawa H, Nakatake R, Okumura T, Ozeki E, Hara I, Morimoto Y, Yoshii K, Kon M. Near-infrared fluorescence imaging and photodynamic therapy with indocyanine green lactosome has antimeoplastic effects for hepatocellular carcinoma. Plos One 2017; 12:e0183527. PMID: 28859104, PMCID: PMC5578495, DOI: 10.1371/journal.pone.0183527

42. Muhanna N, Cui L, Chan H, Burgess L, Jin C S, DacDonald T D, Huynh E, Wang F, Chen J, Irish J C, Zhang G. Multimodal image-guided surgical and photodynamic interventions in head and neck cancer: from primary tumor to metastatic drainage. Clin Cancer Res 2016; 22:961-970. PMID: 26463705, no PMCID, DOI: 10.1158/1078-0432.CCR-15-1235

43. Mahmoudi K, Garvey K L, Bouras A, Cramer G, Stepp H, Raj J G J, Bozec D, Busch T$_M$, Hadjipanayis C G. 5-aminolevulinic acid photodynamic therapy for the treatment of high-grade gliomas. J Neurooncol. 2019 February; 141(3):595-607. PMID: 30659522, PMCID: PMC6538286DOI: 10.1007/s11060-019-03103-4

44. Zhou Z, Yan Y, Wang L, Zhang Q, Cheng Y. Melanin-like nanoparticles decorated with an autophagyinducing peptide for efficient targeted photothermal therapy. Biomaterials 2019; 203:63-72. PMID: 30852424, no PMCID, DOI: 10.1016/j.biomaterials.2019.02.023

45. Fan B, Yang X, Li X, Lv S, Zhang H, Sun J, Li L, Wang L, Qu B, Peng X, Zhang R. Photoacoustic-imagingguided therapy of functionalized melanin nanoparticles: combination of photothermal ablation and gene therapy against laryngeal squamous cell carcinoma. Nanoscale 2019; 11:6285-6296. PMID: 30882835, no PMCID, DOI: 10.1039/c9nr01122f 46. Kim M A, Yon S D, Kim E M, Jeong H J, Lee C M. Natural melanin-loaded nanovesicles for near-infrared mediated tumor ablation by photothermal conversion. Nanotech 2018; 29:415101. PMID: 30028309, no PMCID, DOI: 10.1088/1361-6528/aad4da 47. Zhang L, Sheng D, Wang D, Yao Y, Yang K, Wang Z, Deng L, Chen Y. Bioinspired multifunctional melanin-based nanoliposome for photoacoustic/magnetic resonance imaging-guided efficient photothermal ablation of cancer. Theranostics 2018; 1591-1606. PMID: 29556343, PMCID: PMC5858169, DOI: 10.7150/thno.22430

48. Cho S, Park W, Kim D H. Silica-coated metal chelating-melanin nanoparticles as a dual-modal contrast enhancement imaging and therapeutic agent. ACS Appl Mater Interfaces 2017; 9:101-111. PMID: 27992171, PMCID: PMC5509028, DOI: 10.1021/acsami.6b11304

49. Shabat D. Self-immolative dendrimers as novel drug delivery platforms. J Poly Sci Part A 2006; 44:1569-1578. No PMID, no PMCID, DOI: 10.1002/pola.21258

50. Blencowe C A, Russell A T, Greco F, Hayes W, Thornthwaite D W. Self-immolative linkers in polymeric delivery systems. Polymer Chem 2011; 2:773-790. No PMID, no PMCID, DOI: 10.1039/COPY00324G 51. Rosen B M, Wilson C J, Wilson D A, Peterca M, Imam M R, Percec V. Dendron-mediated self-assembly, disassembly, and self-organization of complex systems. Chem Rev 2009; 109:6275-6540. PMID: 19877614, no PMCID, DOI: 10.1021/cr900157q 52. Zheng H, Lin Z, Shi Y, Tian J, Wang F. Tyrosinase-based reporter gene for photoacoustic imaging of microRNA-9 regulated by DNA methylation in living subjects. Molec Therapy Nucl Acids 2018; 11:34-40. PMID: 29858069, PMCID: PMC5849859, DOI: 10.1016/j.omtn.2018.01.008

53. Liu M, Wang Y, Li M, Feng H, Liu Q, Qin C, Zhang Y, Lan X. Using tyrosinase as a tri-modality reporter gene to monitor transplanted stem cells in acute myocardial infarction. Exp Molec Med 2018; 50:54. PMID: 29700279, PMCID: PMC5938053, DOI: 10.1038/s12276-018-0080-7

54. Feng H, Xia X, Li C, Song Y, Qin C, Zhang Y, Lan X. TYR as a multifunctional reporter gene regulated by the Tet-on system for multimodality imaging: an in vitro study. Sci Rep 2015; 5:15502. PMID: 26483258, PMCID: PMC4611178, DOI: 10.1038/srep15502

55. Paproski R J, Li Y, Barber Q, Lewis J D, Campbell R E, Zemp R. Validating tyrosinase homologue melA as a photoacoustic reporter gene for imaging *Escherichia coli*. J Biomed Optics 2015; 20:106008. PMID: 26502231, no PMCID, DOI: 10.1117/1.JBO.20.10.106008

56. Paproski R J, Heinmiller A, Wachowicz K, Zemp R J. Multi-wavelength photoacoustic imaging of inducible tyrosinase reporter gene expression in xenograft tumors. Sci Rep 2014; 4:5329. PMID: 24936769; PMCID: PMC4060505, DOI: 10.1038/srep05329

57. Qin C, Cheng K, Chen K, Hu X, Liu Y, Lan X, Zhang Y, Liu H, Xu Y, Bu L. Tyrosinase as a multifunctional reporter gene for photoacoustic/MRI/PET triple modality molecular imaging. Sci Rep 2013; 3:1490. PMID: 23508226, PMCID: PMC3603217, DOI: 10.1038/srep01490

58. Krumholz A, VanVickle-Chavez S J, Yao J J, Fleming T P, Gillanders W E, Wang L H V. Photoacoustic microcopy of tyrosinase reporter gene in vivo. J biomed Optis 2011; 16:080503. PMID: 21895303, PMCID: PMC3162617, DOI: 10.1117/1.3606568

59. Paproski R J, Forbrich A E, Wachowicz K, Hitt M M, Zemp R J. Tyrosinase as a dual reporter gene for both photoacoustic and magnetic resonance imaging. Biomed optics Express 2011; 2:771-780. PMID: 21483602, PMCID: PMC3072120, DOI: 10.1364/BOE.2.000771

60. Levi J, Kothapalli S R, Ma T J, Hartman K, Khuri-Yakub B T, Gambhir S S. Design, synthesis and imaging of an activatable photoacoustic probe. J Am Chem Soc 2010; 132:11264-11269. PMID: 20698693, PMCID: PMC2922742, DOI: 10.1021/ja104000a 61. Xia X, Yang M, Oetj en LK, Zhang Y, Li O, Chen J, Xia Y. An enzyme-sensitive probe for photoacoustic imaging and fluorescence detection of protease activity. Nanoscale 2011; 3:950-953. PMID: 21225037, no PMCID, DOI: 10.1039/c0nr00874e.

62. Zha Z, Zhang S, Deng Z, Li Y, Li C, Dai Z. Enzyme-responsive copper sulphide nanoparticles for combined photoacoustic imaging, tumor-selective chemotherapy and photothermal therapy. Chem Comm 2013; 49:3455-457. PMID: 23507786, no PMCID, DOI: 10.1039/c3cc40608c 63. Dragulescu-Andrasi A, Kothapalli S R, Tikhomirov G A, Rao J, Gambhir S S. Activatable oligomerizable imaging agents for photoacoustic imaging of furin-like activity in living subjects. J Am Chem Soc 2013; 135:11015-11022. PMID: 23859847, PMCID: PMC3771329, DOI: 10.1021/ja4010078

64. Yang K, Zhu L, Nie L, Sun X, Cheng L, Wu C, Niu G, Chen X, Liu Z. Visualization of protease activity in vivo using an activatable photoacoustic imaging probe based on CuS nanoparticles. Theranostics 2014; 4:134-141. PMID: 24465271, PMCID: PMC3900798, DOI: 10.7150/thno.7217

65. Hirasawa T, Iwatate R J, Kamiya M, Okawa S, Urano Y, Ishihara M. Multispectral photoacouostic imaging of tumours in mice injected with an enzyme-activatable photoacoustic probe. J Optics 2017; 19:014002. PMID: 29736563, no PMCID, DOI: 10.1007/s11307-018-1203-1

66. Piletic I R, Matthews T E, Warren W S. Estimation of molar absorptivities and pigment sizes for eumelanin and pheomelanin using femtosecond transient absorption spectroscopy. J Chem Phys 2009; 131:181106. PMID: 19916591, PMCID: PMC4108625, DOI: 10.1063/1.3265861

67. Solano F. Melanin and melanin-related polymers as materials with biomedical and biotechnological applications—cuttlefish ink and mussel foot proteins as inspired biomolecules. Int J Molec Sciences 2017; 18:1561. PMID: 28718807, PMCID: PMC5536049, DOI: 10.3390/ijms18071561

68. Zhang R, Fan Q, Yang M, Cheng K, Lu X, Zhang L, Huang W, Cheng Z. Engineering melanin nanoparticles as an efficient drug-delivery system for imaging-guided chemotherapy. 2015; 27:5063-5069. PMID: 26222210, no PMCID, DOI: 10.1002/adma.201502201

69. Liopo A, Su R, Orafesky A A, Melanin nanoparticles as a novel contrast agent for optoacoustic tomography. Photoacoustics 2015; 3:35-43. No PMID, no PMCID, DOI: 10.1016/j.pacs.2015.02.001

70. Fan Q, Cheng K, Hu X, Ma X, Zhang R, Yang M, Lu X, Xing L, Huuang W, Gambhir S S, Cheng Z. Transferring biomarker into molecular probe: melanin nanoparticle as a naturally active platform for multimodality imaging. J Am Chem Soc 2014; 136:15185-15194. PMID: 25292385, PMCID: PMC4227813, DOI: 10.1021/ja505412p 71. Longo D L, Stefania R, Aime S, Oraevsky A. Melanin-based contrast agents for biomedical optoacoustic imaging and theranostic applications. Int J Molec Sci 2017; 18:1719. PMID: 28783106, PMCID: PMC5578109, DOI: 10.3390/ijms18081719

72. Li Y, Sheth V R, Liu G, Pagel M D. A self-calibrating PARACEST MM contrast agent that detects esterase enzyme activity. Contrast Media Molec Imaging 2011; 6:219-228. PMID 21861282, PMCID: PMC4879975, DOI: 10.1002/cmmi.421

73. Fernandez-Cuervo G, Tucker K A, Malm S W, Jones K M, Pagel M D. Diamagnetic imaging agents with a modular chemical design for quantitative detection of β-galactosidase and β-glucuronidase activities with catalyCEST MM. Bioconj Chem 2016, 27:2549-2557. PMID: 27657647, no PMCID, DOI: 10.1021/acs.bioconjchem.6b00482.

74. Cox B, Laufer J G, Arridge S R, Beard P C. Quantitative spectroscopic photoacoustic imaging: a review. J Biomed Opt 2002; 17:061202. PMID: 22734732, no PMCID, DOI: 10.1117/1.JBO.17.6.061202

75. Lutzweiler C, Razansky D. Optoacoustic imaging and tomography: reconstruction approaches and outstanding challenges in image performance and quantification. Sensors 2013; 13:7345-7384. PMID: 23736854, PMCID: PMC3715274, DOI: 10.3390/s130607345

76. Brochu F M, Brunker J, Joseph J, Tomaszewski M, Morscher S, Bohndiek S E. Towards quantitative evaluation of tissue absorption coefficients using light fluence correction in optoacoustic tomography. IEEE Trans Med Imaging 2017; 36:322-331. PMID: 27623576, no PMCID, DOI: 10.1109/TMI.2016.2607199

77. Hupple C W, Morscher S, Burton N C, Pagel M D, McNally L R, Cardenas-Rodriguez J. A light-fluenceindependent method for the quantitative analysis of dynamic contrast-enhanced multispectral optoacoustic tomography (DCE MSOT). Photoacoustics 2018; 10:54-64. No PMID, no PMCID, DOI: 10.1016/j.pacs.2018.04.003

78. Sheth R A, Upadhyay R, Stangenberg L, Sheth R, Weissleder R, Mahmood U. Improved detection of ovarian cancer metastases by intraoperative quantitative fluorescence protease imaging in a pre-clinical model. Gynecol Oncol 2009; 112:616-22. PMID: 19135233, PMCID: PMC2664404, DOI: 10.1016/j.ygyno.2008.11.018

79. Nguyen Q T, Olson E S, Aguilera T A, Jiang T, Scadeng M, Ellies L G, Tsien R Y. Surgery with molecular fluorescence imaging using activatable cell-penetrating peptides decreases residual cancer and improves survival. Proc Nat Acad Sci USA 2010; 107:4317-4322. PMID: 20160097, PMCID: PMC2840114, DOI: 10.1073/pnas.0910261107

80. Mieog J S, Hutteman M, van der Vorst J R, Kuppen P J, Que I, Dijkstra J, Kaijzel E L, Prins F, Lowik C W, Smit V T, van de Velde C J, Vahrmeijer A L. Image-guided tumor resection using real-time near-infrared fluorescence in a syngeneic rat model of primary breast cancer. Breast Cancer Res Treat 2011; 128:679-689. PMID: 20821347, on PMCID, DOI: 10.1007/s10549-010-1130-6.

81. Mito J K, Ferrer J M, Brigman B E, Lee C L, Dodd R D, Eward W C, Marshall L F, Cuneo K C, Carter J E, Ramasunder S, Kim Y, Lee W D, Griffith L G, Bawendi M G, Kirsch D G. Intraoperative detection and removal of microscopic residual sarcoma using wide-field imaging. Cancer 2012; 118; 5320-5330. PMID: 22437667, PMCID: PMC3532657, DOI: 10.1002/cncr.27458

82. Savariar E N, Felsen C N, Nashi N, Jiang T, Ellies L G, Steinbach P, Tsien R Y, Nguyen Q. Real-time in vivo molecular detection of primary tumors and metastases with ratiometric activatable cell-penetrating peptides. Cancer Res 2013; 73:855-64. PMID: 23188503; PMCID: PMC3799878. DOI: 10.1158/0008-5472.CAN-12-2969

83. Hu H Y, Vats D, Vizovisek M, Kramer L, Germanier C, Wendt K U, Rudin M, Turk B, Plettenburg O, Schultz C. In vivo imaging of mouse tumors by a lipidated cathepsin S substrate. Angew Chem Int Ed 2014; 53:7669-7673. PMID: 24888522, PMCID: PMC4298799, DOI: 10.1002/anie.201310979

84. Fujii T, Kamiya M, Urano Y. In vivo imaging of intraperitoneally disseminated tumors in model mice by using activatable fluorescent small-molecular probes for activity of cathepsins. Bioconj Chem 2014; 25:1838-1846. PMID: 25196809, no PMCID, DOI: 10.1021/bc5003289 85. Ofori L O, Withana N P, Prestwood T R, Verdoes M, Brady J J, Winslow M M, Sorger J, Bogyo M. Design of protease activated optical contrast agents that exploit a latent lysosomotropic effect for use in fluorescenceguided surgery. ACS Chem Biol 2015; 10:1977-1988. PMID: 26039341, PMCID: PMC4577961, DOI: 10.1021/acschembio.5b00205

86. Segal E, Prestwood T R, van der Linden W A, Carmi Y, Bhattacharya N, Withana N, Verdoes M, Habtezion A, Engleman E G, Bogyo M. Detection of intestinal cancer by local, topical application of a quenched fluorescence probe for cysteine cathepsins. Chem Biol 2015; 22:148-158. PMID: 25579207, PMCID: PMC4353655, DOI: 10.1016/j.chembio1.2014.11.008

87. Chi C, Zhang Q, Mao Y, Kou D, Qiu J, Ye J, Wang J, Wang Z, Du Y, Tian J. Increased precision of orthotopic and metastatic breast cancer surgery guided by matrix metalloproteinase-activatable nearinfrared fluorescence probes. Sci Rep 2015; 5:14197. PMID: 26395067, PMCID: PMC4585795, DOI: 10.1038/srep14197

88. Metildi C A, Felsen C N, Savariar E N, Nguyen Q, Kaushal S, Hoffman R M, Tsien R Y, Bouvet M. Ratiometric activatable cell-penetrating peptides label pancreatic cancer, enabling fluorescence-guided surgery, which reduces metastases and recurrence in orthotopic mouse models. Ann Surg Oncol 2015; 22:2082-2087. PMID: 25319581; PMCID: PMC4400250, DOI: 10.1245/s10434-014-4144-1

89. Whitley M J, Cardona D M, Lazarides A L, Spasojevic I, Ferrer J M, Cahill J, Lee C L, Snuderi M, Blazer D G, Hwang E S, Greenup R A, Mosca P J, Mito J K, Cuneo K C, Lamer N A, O'Reilly E K, Riedel R F, Eward W C, Strasfeld D B, Fukumura D, Jain R K, Lee W D, Griffith L G, Bawendi M G, Kirsch D G, Brigman B E. A mousehuman phase 1 co-clinical trial of a protease-activated fluorescent probe for imaging cancer. Sci Transl Med 2016; 8:320ra324. PMID: 26738797, PMCID: PMC4794335, DOI: 10.1126/scitranslmed.aad0293

90. Orosco R K, Savariar E N, Weissbrod P A, Diaz-Perez J A, Bouvet M, Tsien R Y, Nguyen Q. Molecular targeting of papillary thyroid carcinoma with fluorescently labeled ratiometric activatable cell penetrating peptides in a transgenic murine model. J Surg Oncol 2016; 113:138-143. PMID: 26799257; PMCID: PMC4986916, DOI: 10.1002/jso.24129

91. Hussain T, Savariar E N, Diaz-Perez J A, Messer K, Pu M, Tsien R Y, Nguyen Q. Surgical molecular navigation with ratiometric activatable cell penetrating peptide for intraoperative identification and resection of small salivary gland cancers. Head Neck 2016; 38:715-723. PMID: 25521629; PMCID: PMC4472578, DOI: 10.1002/hed.23946

92. Unkart J T, Chen S L, Wapnir I L, Gonzalez J E, Harootunian A, Wallace A M. Intraoperative tumor detection using a ratiometric activatable fluorescent peptide: a first-in-human phase 1 study. Ann Surg Oncol 2017; 24:3167-73. PMID: 28699134, no PMCID, DOI: 10.1245/s10434-017-5991-3

93. Miampamba M, Liu J, Harootunian A, Gale A J, Baird S, Chen S L, Nguyen Q, Tsien R Y, Gonzalez J E. Sensitive in vivo visualization of breast cancer using ratiometric protease-activatable fluorescent imaging agent, AVB-620. Theranostics 2017; 7:3369-3386. PMID: 28900516, PMCID: PMC5595138, DOI: 10.7150/thno.20678

94. Hingorani D V, Lemieux A J, Acevedo J R, Glasgow H L, Kedarisetty S, Whitney M A, Molinolo A A, Tsien R Y, Nguyen Q. Early detection of squamous cell carcinoma in carcinogen induced oral cancer rodent model by ratiometric activatable cell penetrating peptides. Oral Oncol 2017; 71:156-162. PMID: 28688684, PMCID: PMC5575898, DOI: 10.1016/j.oraloncology.2017.06.009

95. Reaction A: Boger D L, Yohannes D. Selectively protected L-DOPA derivatives: Application of benzylic hydroperoxide rearrangement. J Org Chem 1987; 52:5283-5286. No PMID, no PMCID, no DOI.

96. Reaction B: (a) Wuts P G M, Greene T W. Greene's Protective Groups in Organic Synthesis, 4th Edition. John Wiley & Sons, Inc., New York, NY, 2006. No PMID, no PMCID, no DOI. (b) He G, Lu C, Zhao Y, Nack W A, Chen G. Improved protocol for indoline synthesis via palladiumcatalyzed intramolecular C(sp2)-H amination. Org Lett 2012; 14:2944-2947. PMID: 22670815, no PMCID, DOI: 10.1021/01301352v 97. Reaction C: (a) Kendall P M, Johnson J V, Cook C E. Synthetic route to an aromatic analog of strigol. J Org Chem 1979; 44:1421-2424. No PMID, no PMCID, no DOI. (b) Ronald R C, Lasinger J M, Lillie T S, Wheeler C J. Total synthesis of frustulosin and aurocitrin. J Org Chem 1082; 47; 2541-2549. No PMID, no PMCID, no DOI.

98. Reaction D: He G, Lu C, Zhao Y, Nack W A, Chen G. Improved protocol for indoline synthesis via palladium-catalyzed intramolecular C(sp2)-H amination. Org Lett 2012; 14:2944-2947. PMID: 22670815, no PMCID, DOI: 10.1021/01301352v 99. Reaction E: Chen Y F, Wilcoxen K. An improved synthesis of selectively protected L-DOPA derivatives from L-tyrosine. J Org Chem 2000; 65:2574-2576. PMID: 10789475, no PMCID, no DOI.

100. Reaction F: Vezenkov L, Honson N S, Kumar N S, Bosc D, Kovacic S, nguyen TG, Pfeifer T A, Young R N. Development of fluorescent peptide substrates and assays for the key autophagy-initiating cysteine protease enzyme, ATG4B. Bioorg Med Chem 2015; 23:3237-3247. PMID: 25979376, no PMCID, DOI: 10.1016/j.bmc.2015.04.064

101. Reaction G: Eichberg M J, Dorta R L, Lamottke K, Vollhardt K P C. The formal total synthesis of (+−)-strychnine via a cobalt-mediated [2+2+2]cycloaddition. Org Lett 2000; 2:2479-2481. PMID: 10956526, no PMCID, no DOI.

102. Reaction H: Ito S, Inoue S, Yamamoto Y, Fujita K. Synthesis and antitumor activity of cysteinyl-3,4-dihydroxyphenylalanines and related compounds. J Med Chem 1981; 24:673-677. PMID: 6788955, no PMCID, no DOI 103. Reaction I: Wuts P G M, Greene T W. Greene's Protective Groups in Organic Synthesis, 4th Edition. John Wiley & Sons, Inc., New York, NY, 2006. No PMID, no PMCID, no DOI.

104. Pagel M D. Structures and related properties of helical, disulfide-stabilized peptides. Ph.D. dissertation. Lawrence Berkeley Laboratory, University of California, Berkeley, 1993. Structures and related properties of helical, disulfide-stabilized peptides.

105. Vezenkov L, Honson N S, Kumar N S, Bosc D, Kovacic S, nguyen TG, Pfeifer T A, Young R N. Development of fluorescent peptide substrates and assays for the key autophagy-initiating cysteine protease enzyme, ATG4B. Bioorg Med Chem 2015; 23:3237-3247. PMID: 25979376, no PMCID, DOI: 10.1016/j.bmc.2015.04.064

106. Yoo B, Pagel M D. Peptidyl molecular imaging contrast agents using a new solid phase peptide synthesis approach. Bioconj Chem 2007; 18:903-911. PMID: 17330953, PMCID: PMC2584118, DOI: 10.1021/bc060250q 107. Yoo B, Pagel M D. A facile synthesis of α-amino-DOTA as a versatile molecular imaging probe. Tet Lett 2006; 47:7327-7330. No PMID, no PMCID, DOI: 10.1016/j.tetlet.2006.08.019

108. Liu G, Li Y, Pagel M D. Design and characterization of new irreversible responsive PARACEST Mill contrast agent that detects nitric oxide. Magn Reson Med 2007; 58:1249-1256. PMID 18046705, no PMCID, DOI: 10.1002/mrm.21428

109. Yoo B, Sheth V, Pagel M D. An amine-derivatized, DOTA-loaded polymeric support for Fmoc solid phase peptide synthesis. Tet Lett 2009; 50:4459-4462. PMID 20161272, PMCID: PMC2702766, DOI: 10.1016/j.tetlet.2009.05.061

110. Ali M M, Yoo B, Pagel M D. Tracking the relative in vivo pharmacokinetics of nanoparticles with PARACEST MM. Molec Pharmaceutics 2009; 6:1409-1416. PMID 19298054, PMCID: PMC4216567, DOI: 10.1021/mp900040u 111. Hingorani D V, Randtke E A, Pagel M D. A catalyCEST MM contrast agent that detects the enzymecatalyzed creation of a covalent bond. J Am Chem Soc 2013; 135:6396-6398. PMID 23601132, PMCID: PMC3667154, DOI: 10.1021/j a400254e.

112. Yoo B, Sheth V R, Howison C M, Douglas M J K, Pineda C T, Maine E A, Baker A F, Pagel M D. Detection of in vivo enzyme activity with catalyCEST MM. Mag Reson Med 2014; 71:1221-1230. PMID 23640714, PMCID: PMC3742626, DOI: 10.1002/mrm.24763.

113. Fernandez-Cuervo G, Sinharay S, Pagel M D. A catalyCEST Mill contrast agent that can simultaneously detect two enzyme activities. ChemBioChem, 2016; 17(5):383-387. PMID: 26693680, PMCID: PMC4814164, DOI: 10.1002/cbic.201500586.

114. Sinharay S, Fernandez-Cuervo G, Acfalle J P, Pagel M D. Detection of sulfatase enzyme activity with a catalyCEST MM contrast agent. Chem Euro J 2016; 22:6491-6495. PMID: 26956002, PMCID: PMC4877021, DOI: 10.1002/chem.201600685

115. Daryaei I, Randtke E A, Pagel M D. A biomarker-responsive T2ex MM contrast agent. Magn Reson Med 2017; 77:1665-1670. PMID: 27090199, PMCID: PMC5071101, DOI: 10.1002/mrm.26250

116. Sinharay S, Randtke E A, Jones K M, Howison C M, Chambers S K, Kobayashi H, Pagel M D. Noninvasive detection of enzyme activity in tumor models of human ovarian cancer using catalyCEST MM. Magn Reson Med 2017; 77:2005-2014. PMID: 27221386, PMCID: PMC5123981, DOI: 10.1002/mrm.26278

117. Daryaei I, Jones K M, Pagel M D. Detection of DT-diaphorase enzyme with a paraCEST MRI contrast agent. Chem Euro J 2017; 23:6514-6517. PMID: 28370655, no PMCID, DOI: 10.1002/chem.201700721.

118. Sinharay S, Howison C M, Baker A F, Pagel M D. Detecting in vivo urokinase Plasminogen Activator activity with a catalyCEST MM contrast agent. NMR Biomed 2017, 30(7):e3721. PMID: 28370884, PMCID: PMC5704996, DOI: 10.1002/nbm.3721

119. Sinharay S, Randtke E A, Howison C M, Ignatenko N A, Pagel M D. Detection of enzyme activity and inhibition during studies in solution, in vitro and in vivo with catalyCEST MM. Molec Imaging Biol 2018; 20:240-248. PMID: 28726131, no PMCID, DOI: 10.1007/s11307-017-1092-8

120. Blencowe C A, Russell A T, Greco F, Hayes W, Thornwaite D W. Self-immolative linkers in polymeric delivery systems. Polymer Chem 2011; 2:773-790. No PMID, no PMCID, DOI: 10.1039/COPY00324G 121. Yoo B, Pagel M D. A PARACEST MRI contrast agent to detect enzyme activity. J Am Chem Soc 2006; 128:14032-14033. PMID 17061878, no PMCID, DOI: 10.1021/ja063874f 122. Yoo B, Raam M, Rosenblum R, Pagel M D. Enzyme-responsive PARACEST MRI contrast agents: A new biomedical imaging approach for studies of the proteasome. Contrast Media Molec Imaging 2007; 2:189-198. PMID 17712869, no PMCID, DOI: 10.1002/cmmi.145

123. Cat B Fast commercial product information: http://www.perkinelmer.com/lab-products-andservices/application-support-knowledgebase/in-vivo-preclinical-imaging/cat-b-fast-ask.html 124. Sensolyte—AFC® Urokinase (uPA) Activity Assay Kit commercial product information: https://www.anaspec-.com/products/product.asp?id=51781

125. Withana N P, Blum G, Sameni M, Sameni M, Slaney C, Anbalagan A, Olive M B, Bidwell B N, Edgington L, Wang L, Moin K, Sloane B F, Anderson R L, Bogyo M S, Parker B S. Cathepsin B inhibition limits bone metastasis in breast cancer. Cancer Res 2012; 72:1199-1209. PMID: 22266111, PMCID: PMC3538126, DOI: 10.1158/0008-5472.CAN-11-2759

126. Billstrom A, Hartley-Asp B, Lecander I, Batra S, Astedt B. The urokinase inhibitor p-aminobenzamidine inhibits growth of a human prostate tumor in SCID mice. Int J Cancer 1995; 61:542-547. PMID: 7759160, no PMCID, no DOI 127. Randtke E A, Chen L Q, Corrales L R, Pagel M D. The Hanes-Woolf Linear QUESP method improves the measurements of fast chemical exchange rates with CEST MRL Magn Reson Med 2014; 71:1603-1612. PMID 23780911, PMCID: PMC3784632, DOI: 10.1002/mrm.24792.

128. Xing R, Addington A K, Mason R W. Quantification of cathepsins B and L in cells. Biochem J 1998; 332:499-505. PMID: 9601080, PMCID: PMC1219506, DOI: 10.1042/bj3320499

129. Zajc I, Frangež L, Lah T T. Expression of cathepsin B is related to tumorigenicity of breast cancer cell lines. Radiol Oncol 2003; 37:233-240. PMID: 12715895, no PMCID, DOI: 10.1515/BC.2003.050

130. Bajou K, Lewalle J M, Martinez C R, Soria C, Lu H, Noel A, Foidart J M. Human breast adenocarcinoma cell lines promote angiogenesis by providing cells with uPA-PAI-1 and by enhancing their expression. Int J Cancer 2002; 100:501-506. PMID: 12124797, no PMCID, DOI: 10.1002/ijc.10487

131. LeBeau A M, Sevillano N, King M L, Duriseti S, Murphy S T, Craik C S, Murphy L L, VanBrocklin HF.

Imaging the urokinase plasminongen activator receptor in preclinical breast cancer models of acquired drug resistance. Theranostics 2014; 4:267-279. PMID: 24505235, PMCID: PMC3915090, DOI: 10.7150/thno.7323

132. Sliutz G, Eder H, Koelbl H, Tempfer C, Auerbach L, Schneeberger C, Kainz C, Zeillinger R. Quantification of uPA receptor expression in human breast cancer cell lines by cRT-PCR. Breast Cancer Res Treatment 1996; 40:257-263. PMID: 8883968, no PMCID, no DOI.

133. Huber M C, Mall R, Braselmann H, Feuchtinger A, Molatore S, Lindner K, Walch A, Gross E, Schmitt M, Falkenberg N, Aubele M. uPAR enhances malignant potential of triple-negative breast cancer by directly interacting with uPA and IGF1R. BMC Cancer 2016; 16:615. PMID: 27502396, PMCID: PMC4977758, DOI: 10.1186/s12885-016-2663-9

134. Bishop J A, Nelson A M, Merz W G, Askin F B, Riedel S. Evaluation of the detection of melanin by the Fontana-Masson silver stain in tissue with a wide range of organisms including *Cryptococcus*. Hum Pathol 2012; 43:898-903. PMID: 22154051, no PMCID, DOI: 10.1016/j.humpath.2011.07.021

135. Kobes J E, Daryaei I, Howison C M, Bontrager J G, Siriani R S, Meuillet E M, Pagel M D. Improved treatment of pancreatic cancer with drug delivery nanoparticles loaded with a novel AKT/PDK1 inhibitor. Pancreas 2016; 45:1158-1166. PMID: 26918875, PMCID: PMC4983222, DOI: 10.1097/MPA.0000000000000607.

136. Miller L R, Marks C, Becker J B, Hum P D, Chen W J, Woodruff T, McCarthy M M, Sohrabji F, Schiebinger L, Wetherington C L, Makris S, Arnold A P, Einstein G, Miller V M, Sandberg K, Maier S, Cornelison T L, Clayton J A. Considering sex as a biological variable in preclinical research. FASEB J, 2017; 31:29-34. PMID: 27682203, no PMCID, DOI: 10.1096/fj.201600781R 137. Alford R, Simpson H M, Dubeman J, Hill G C, Ogawa M, Regino C, Kobayashi H, Choyke P L. Toxicity of organic fluorophores used in molecular imaging: Literature review. Mol Imaging 2009; 8:341-354. PMID: 20003892, no PMCID, no DOI.

138. Chen L Q, Randtke E A, Jones K M, Moon B F, Howison C M, Pagel M D. Evaluations of tumor acidosis within in vivo tumor models using parametric maps generated with acidoCEST MRI. Mol Imaging Biol 2015; 17:488-496. PMID: 25622809, PMCID: PMC4880367, DOI: 10.1007/s11307-014-0816-2.

Detection of Hydrolase Activity

1. Gambhir S S, Yaghoubi S S. Molecular Imaging with Reporter Genes. Cambridge University Press, 2010. No PMID, no PMCID, DOI: 10.1017/CB09780511730405

2. Bourdeau R W, Lee-Gosselin A, Lakshmanan A, Farhadi A, Kumar S R, Nety S P, Shapiro M G. Acoustic reporter genes for noninvasive imaging of microorganisms in mammalian hosts. Nature 2018; 553:86-90. PMID: 29300010, PMCID: PMC5920530, DOI: 10.1038/nature25021

3. Ntziachristos V, Razansky D. Molecular imaging by means of multispectral optoacoustic tomography (MSOT). Chem Rev 2010; 110:2783-2794. PMID: 20387910, no PMCID, DOI: 10.1021/cr9002566

4. Taruttis A, Ntziachristos V. Advances in real-time multispectral optoacoustic imaging and its applications. Nat Photon 2015; 9:219-227. No PMID, no PMCID, DOI: 10.1038/nphoton.2015.29

5. Mason H S. A classification of melanins. Ann New York Acad Sci 1948; 4:399-404. PMID: 18862181, no PMCID, no DOI.

6. del Marmol V, Beermann F. Tyrosinase and related proteins in mammalian pigmentation. FEBS Lett 1996; 382:165-168. PMID: 8601447, no PMCID, no DOI.

7. Cox B, Laufer J G, Arridge S R, Beard P C. Quantitative spectroscopic photoacoustic imaging: a review. J Biomed Opt 2002; 17:061202. PMID: 22734732, no PMCID, DOI: 10.1117/1.JBO.17.6.061202

8. Lutzweiler C, Razansky D. Optoacoustic imaging and tomography: reconstruction approaches and outstanding challenges in image performance and quantification. Sensors 2013; 13:7345-7384. PMID: 23736854, PMCID: PMC3715274, DOI: 10.3390/s130607345

9. Brochu F M, Brunker J, Joseph J, Tomaszewski M, Morscher S, Bohndiek S E. Towards quantitative evaluation of tissue absorption coefficients using light fluence correction in optoacoustic tomography. IEEE Trans Med Imaging 2017; 36:322-331. PMID: 27623576, no PMCID, DOI: 10.1109/TMI.2016.2607199

10. Hall C V, Jacob P E, Ringold G M, Lee F. Expression and regulation of *Escherichia coli* lacZ gene fusions in mammalian cells. J Molec App Gen 1983; 2:101-109. PMID: 6302193, no PMCID, no DOI.

11. Jefferson R A. Burgess S M. Hirsh D. Beta-Glucuronidase from *Escherichia coli* as a gene-fusion marker. Proc Nat Acad Sci USA 1986; 83: 8447-8451. PMID 3534890, PMCID: PMC386947, DOI: 10.1073/pnas.83.22.8447.

12. Eustice D C, Feldman P A, Colberg-Poley A M, Buckery R M, Neubauer R H. A sensitive method for the detection of beta-galactosidase in transfected mammalian cells. Biotechniques 1991; 11:739-740. PMID: 1809326, no PMCID, no DOI.

13. Louie A Y, Huber M M, Ahrens E T, Rothbacher U, Moats R, Jacobs R E, Fraser S E, Meade T E. In vivo visualization of gene expression using magnetic resonance imaging. Nat Biotechnol 2000; 18:321-325. PMID: 10700150, no PMCID, DOI: 10.1038/73780

14. Tung, C. H., Zeng, Q., Shah, K., Kim, D E, Schellingerhout D, Weissleder R. In vivo imaging of beta-galactosidase activity using far red fluorescent switch. Cancer Res 2004; 64:1579-1583. PMID: 14996712, no PMCID, no DOI 15. Wehrman T S, von Degenfeld G, Krutzik P O, Nolan G P, Blau H M. Luminescent imaging of beta-galactosidase activity in living subjects using sequential reporter-enzyme luminescence. Nat Methods. 2006; 3:295-301. PMID: 16554835, no PMCID, DOI: 10.1038/nmeth868

16. Kodibagkar V D, Yu J, Liu L, Hetherington H P, Mason R P. Imaging beta-galactosidase activity using 19F chemical shift imaging of LacZ gene-reporter molecule 2-fluoro-4-nitrophenol-beta-D-galactopyranoside. Magn Reson Imaging. 2006; 24:959-962. PMID: 16916713, no PMCID, DOI: 10.1016/j.mri.2006.04.003

17. Li L, Zemp R J, Lungu G, Stoica G, Wang L V. Photoacoustic imaging of lacZ gene expression in vivo. J Biomed Opt 2007; 12:020504. PMID: 17477703, no PMCID, DOI: 10.1117/1.2717531

18. Su Y C, Chuang K H, Wang Y M, Cheng C M, Lin S R, Wang J Y, Hwang J J, Chen B M, Chen K C, Roffler S, Cheng T L. Gene expression imaging by enzymatic catalysis of a fluorescent probe via membrane anchored 3-glucuronidase. Gene Ther 2007; 14:565-574. PMID: 17235292, no PMCID, DOI: 10.1038/sj.gt.3302896

19. van Dort M E, Lee K C, Hamilton C A, Rehemtulla A, Ross B D. Radiosynthesis and evaluation of 5-[125I]iodoindol-3-yl-beta-D-galactopyranoside as a beta-galactosidase imaging radioligand. Mol Imaging. 2008; 7:187-197. PMID: 19123989, PMCID: PMC2743942, no DOI.

20. Celen S, Cleynhens J, Deroose C, de Groot T, Ibrahimi A, Gijsbers R, Debyser Z, Mortelmans L, Verbruggen A, Bormans G. Synthesis and biological evaluation of (11) C-labeled beta-galactosyl triazoles as potential PET tracers for in vivo LacZ reporter gene imaging. Bioorg Med Chem. 2009; 17:5117-5125. PMID: 19515568, no PMCID, DOI: 10.1016/j.bmc.2009.05.056

21. Zhang G J, Chen T B, Connolly B, Lin S A, Hargreaves R, Vanko A, Bednar B, Macneil D J, Sur C, Williams D L. In vivo optical imaging of LacZ expression using lacZ transgenic mice. Assay Drug Dev Technol. 2009; 7:391-399. PMID: 19689207, no PMCID, DOI: 10.1089/adt.2009.0195

22. Tzou S C, Roffler S, Chuang K H, Yeh H P, Kao C H, Su Y C, Cheng C M, Tseng W L, Shiea J, Harm I H, Cheng K W, Chen B M, Hwang J J, Cheng T L, Wang H E. Micro-PET imaging of β-glucuronidase activity by the hydrophobic conversion of a glucuronide probe. Radiology 2009; 252:754-62. PMID: 19717754, no PMCID, DOI: 10.1148/radiol.2523082055

23. Liu L, Mason R P. Imaging beta-galactosidase activity in human tumor xenografts and transgenic mice using a chemiluminescent substrate. PLoS One 2010; 5:e12024. DOI: 10.1371/journal.pone.0012024. PMID: 20700459, PMCID: PMC2917367, DOI: 10.1371/journal-.pone.0012024

24. Cui W, Liu L, Kodibagkar V D, Mason R P. Magn Reson Med 2010. S-Gal®, a novel 1H Mill reporter for β-galactosidase. Magn Reson Med 2010; 64:65-71. DOI: 10.1002/mrm.22400. PMID: 20572145, PMCID: PMC2924164, DOI: 10.1002/mrm.22400

25. Antunes I F, Haisma H J, Elsinga P H, van Waarde A, Willemsen A T, Dierckx R A, de Vries E F. In vivo evaluation of 1-O-(4-(2-fluoroethyl-carbamoyloxymethyl)-2-nitrophenyl)-O-β-D-glucopyronuronate: a positron emission tomographic tracer for imaging β-glucuronidase activity in a tumor/inflammation rodent model. Mol. Imaging 2012; 11:77-87. PMID: 22418030, no PMCID, no DOI.

26. Su Y C, Cheng T C, Leu Y L, Roffler S R, Wang J Y, Chuang C H, Kao C, Chen K C, Wang H E, Cheng T L. PET imaging of β-glucuronidase activity by an activity-based 124I-trapping probe for the personalized glucuronide prodrug targeted therapy. Mol Cancer Ther 2014; 13:2852-2863. PMID: 25277385, no PMCID, DOI: 10.1158/1535-7163.MCT-14-0212

27. Asanuma D, Sakabe M, Kamiya M, Yamamoto K, Hiratake J, Ogawa M, et al. Sensitive beta-galactosidase-targeting fluorescence probe for visualizing small peritoneal metastatic tumours in vivo. Nat Commun (2015) 6:6463. PMID: 25765713, PMCID: PMC4382686, DOI: 10.1038/ncomms7463

28. Fernández-Cuervo G, Tucker K A, Maim S W, Jones K M, Pagel M D. Diamagnetic imaging agents with a modular chemical design for quantitative detection of β-galactosidase and β-glucuronidase activities with catalyCEST MM. Bioconj Chem 2016, 27:2549-2557. PMID: 27657647, no PMCID, DOI: 10.1021/acs.bioconjchem.6b00482.

29. Valluru K S, Wilson K E, Willman J K. Photoacoustic imaging in oncology: Translational preclinical and early clinical experience. Radiology 2016; 280:332-349. PMID: 27429141, PMCID: PMC4976462, DOI: 10.1148/radio1.16151414

30. Buehler A, Dean-ben XL, Claussen J, Ntziachristos V, Razansky D. Three-dimensional optoacoustic tomography at video rate. Opt Express 2012; 20:22712-22719. PMID: 23037421, no PMCID, no DOI.

31. Taruttis A, Morscher S, Burton N C, Razansky D, Ntziachristos V. Fast multispectral optoacoustic tomography (MSOT) for dynamic imaging of pharmacokinetics and biodistribution in multiple organs. PLoS ONE 2012; 7:e30491. PMID: 22295087, PMCID: PMC3266258, DOI: 10.1371/journal.pone.0030491

32. Dean-Ben X L, Bay E, Razansky D. Functional optoacoustic imaging of moving objects using microsecond-delay acquisition of multi spectral three-dimensional tomographic data. Sci Rep 2014; 4:5878. PMID: 25073504, PMCID: PMC4115207, DOI: 10.1038/srep05878

33. Fehm T E, Dean-Ben X L, Ford S J, Razansky D. In vivo whole-body optoacoustic scanner with real-time volumetric imaging capacity. Optica 2016; 3:1153-1159. No PMID, no PMCID, DOI: 10.1364/OPTICA.3.001153

34. Krumholz A, VanVickle-Chavez S J, Yao J, Fleming T P, Gillanders W E, Wang L V. Photoacoustic microscopy of tyrosinase reporter gene in vivo. J Biomed Optics 2011; 16:080503. PMID: 21895303, PMCID: PMC3162617, DOI: 10.1117/1.3606568

35. Paproski R J, Forbrich A E, Wachowicz K, Htt M M, Zemp R J. Tyrosinase as a dual reporter gene for both photoacoustic and magnetic resonance imaging. Biomed Opt Express 2011; 2:771-780. PMID: 21483602, PMCID: PMC3072120, DOI: 10.1364/BOE.2.000771

36. Qin C, Cheng K, Chen K, Hu X, Liu Y, Lan X, Zhang Y, Liu H, Xu Y, Bu L, Su X, Zhu X, Meng S, Cheng Z. Tyrosinase as a multifunctional reporter gene for Photoacoustic/MRI/PET triple modality molecular imaging. Sci Rep 2013; 3:1490. PMID: 23508226, PMCID: PMC3603217, DOI: 10.1038/srep01490

37. Stritzker J, Kirscher L, Scadeng M, Deliolanis N C, Morscher S, Symvoulidis P, Schaefer K, Zhang Q, Buckel L, Hess M, Donat U, Bradley W G, Ntziachristos V, Szalay A A. Vaccinia virus-mediated melanin production allows MR and optoacoustic deep tissue imaging and laser-induced thermotherapy of cancer. Proc Nat Acad Sci USA 2013; 110:3316-3320. PMID: 23401518, PMCID: PMC3587225, DOI: 10.1073/pnas.1216916110

38. Paproski R J, Heinmiller A, Wachowicz K, Zemp R J. Multi-wavelength photoacoustic imaging of inducible tyrosinase reporter gene expression in xenograft tumors. Sci Rep 2014; 4:5329. PMID: 24936769, PMCID: PMC4060505, DOI: 10.1038/srep05329

39. Feng H, Xia X, Li C, Song Y, Zin C, Zhang Y, Lan X. TYR as a multifunctional reporter gene regulated by the Tet-on system for multimodality imaging: an in vitro study. Sci Rep 2015; 5:15502. PMID: 26483258, PMCID: PMC4611178, DOI: 10.1038/srep15502

40. Paproski R J, Li Y, Barber Q, Lewis J D, Campbell R E, Zemp R. Validating tyrosinase homologue melA as a photoacoustic reporter gene for imaging *Escherichia coli*. J Biomed Optics 2015; 20:106008. PMID: 26502231, no PMCID, DOI: 10.1117/1.JBO.20.10.106008

41. Jathoul A P, Laufer J, Ogunlade O, Treeby B, Cox B, Zhang E, Johnson P, Pizzey A R, Philip B, Marafioti T, Lythgoe M F, Bedley R B, Pule M A, Beard P. Deep in vivo photoacoustic imaging of mammalian tissues using a tyrosine-based genetic reporter. Nature Photonics 2015; 9:239-246. No PMID, no PMCID, DOI: 10.1038/nphoton.2015.22

42. Brunker J, Yao J, LAufer J, Bohndiek S E. Photoacoustic imaging using genetically encoded reporters: a review. J Biomed Optics 2017; 22:070901. PMID: 28717818, no PMCID, DOI: 10.1117/1.JBO.22.7.070901
43. Levi J, Kothapalli S R, Ma T J, Hartman K, Khuri-Yakub B T, Gambhir S S. Design, synthesis and imaging of an activatable photoacoustic probe. J Am Chem Soc 2010; 132:11264-11269. PMID: 20698693, PMCID: PMC2922742, DOI: 10.1021/ja104000a
44. Xia X, Yang M, Oetj en LK, Zhang Y, Li O, Chen J, Xia Y. An enzyme-sensitive probe for photoacoustic imaging and fluorescence detection of protease activity. Nanoscale 2011; 3:950-953. PMID: 21225037, no PMCID, DOI: 10.1039/c0nr00874e.
45. Zha Z, Zhang S, Deng Z, Li Y, Li C, Dai Z. Enzyme-responsive copper sulphide nanoparticles for combined photoacoustic imaging, tumor-selective chemotherapy and photothermal therapy. Chem Comm 2013; 49:3455-457. PMID: 23507786, no PMCID, DOI: 10.1039/c3cc40608c
46. Dragulescu-Andrasi A, Kothapalli S R, Tikhomirov G A, Rao J, Gambhir S S. Activatable oligomerizable imaging agents for photoacoustic imaging of furin-like activity in living subjects. J Am Chem Soc 2013; 135:11015-11022. PMID: 23859847, PMCID: PMC3771329, DOI: 10.1021/ja4010078
47. Yang K, Zhu L, Nie L, Sun X, Cheng L, Wu C, Niu G, Chen X, Liu Z. Visualization of protease activity in vivo using an activatable photoacoustic imaging probe based on CuS nanoparticles. Theranostics 2014; 4:134-141. PMID: 24465271, PMCID: PMC3900798, DOI: 10.7150/thno.7217
48. Hirasawa T, Iwatate R J, Kamiya M, Okawa S, Urano Y, Ishihara M. Multispectral photoacouostic imaging of tumours in mice injected with an enzyme-activatable photoacoustic probe. J Optics 2017; 19:014002. PMID: 29736563, no PMCID, DOI: 10.1007/s11307-018-1203-1
49. Grootendorst D J, Jose J, Wouters M W, van Boven H, Van der Hage J, Van Leeuwen D G, Steenbergen W, Manohar S, Ruers T J M. First experiences of photoacoustic imaging for detection of melanoma metastases in resected human lymph nodes. Lasers Surg Med 2012; 44:541-549. PMID: 22886491, no PMCID, DOI: 10.1002/1sm.22058
50. Zhou Y, Li G, Zhu L, Li C, Cornelius L A, Wang L V. Handheld photoacoustic probe to detect both melanoma depth and volume at high speed in vivo. J Biophotonics 2015; 8:961-967. PMID: 25676898, PMCID: PMC4530093, DOI: 10.1002/jbio.201400143
51. Stoffels I, Morscher S, Helfrich I, Hillen U, Leyh J, Burton N C, Sardella T C P, Claussen J, Poeppel T D, Bachmann H S, Roesch A, Briewank K, Schadendorf D, Gunzer M, Klode J. Metastatic status of sentinel lymph nodes in melanoma determined noninvasively with multispectral optoacoustic imaging. Sci Trans Med 2015; 7:317ra199. PMID: 26659573, no PMCID, DOI: 10.1126/scitranslmed.aad1278
52. Schwarz M, Buehler A, Aguirre J, Ntziachristos V. Three-dimensional multispectral optoacoustic mesoscopy reveals melanin and blood oxygenation in human skin in vivo. J Biophotonics 2016; 9:55-60. PMID: 26530688, no PMCID, DOI: 10.1002/jbio.201500247
53. Lavaud J, Henry M, Coll J L, Josserand V. Exploration of melanoma metastases in mice brains using endogenous contrast photoacoustic imaging. Int J Pharmaceutics 2017; 532:704-709. PMID: 28847669, no PMCID, DOI: 10.1016/j.ijpharm.2017.08.104
54. Shah A, Delgado-Goni T, Casals Galobart T, Wantuch S, Jamin Y, Leach M O, Robinson S P, Bamber J, Beloueche-Babari M. Detecting human melanoma cell re-differentiation following BRAF or heat shock protein 90 inhibition using photoacoustic and magnetic resonance imaging. Sci Rep 2017; 7:8215. PMID: 28811486, PMCID: PMC5557970, DOI: 10.1038/s41598-017-07864-8
55. Shabat D. Self-immolative dendrimers as novel drug delivery platforms. J Poly Sci Part A 2006; 44:1569-1578. No PMID, no PMCID, DOI: 10.1002/pola.21258
56. Blencowe C A, Russell A T, Greco F, Hayes W, Thornthwaite D W. Self-immolative linkers in polymeric delivery systems. Polymer Chem 2011; 2:773-790. No PMID, no PMCID, DOI: 10.1039/COPY00324G
57. Rosen B M, Wilson C J, Wilson D A, Peterca M, Imam M R, Percec V. Dendron-mediated self-assembly, disassembly, and self-organization of complex systems. Chem Rev 2009; 109:6275-6540. PMID: 19877614, no PMCID, DOI: 10.1021/cr900157q
58. Li Y, Sheth V R, Liu G, Pagel M D. A self-calibrating PARACEST MM contrast agent that detects esterase enzyme activity. Contrast Media Molec Imaging 2011; 6:219-228. PMID 21861282, PMCID: PMC4879975, DOI: 10.1002/cmmi.421
59. Zhang R, Fan Q, Yang M, Cheng K, Lu X, Zhang L, Huang W, Cheng Z. Engineering melanin nanoparticles as an efficient drug-delivery system for imaging-guided chemotherapy. 2015; 27:5063-5069. PMID: 26222210, no PMCID, DOI: 10.1002/adma.201502201
60. Liopo A, Su R, Orafesky A A, Melanin nanoparticles as a novel contrast agent for optoacoustic tomography. Photoacoustics 2015; 3:35-43. No PMID, no PMCID, DOI: 10.1016/j.pacs.2015.02.001
61. Fan Q, Cheng K, Hu X, Ma X, Zhang R, Yang M, Lu X, Xing L, Huuang W, Gambhir S S, Cheng Z. Transferring biomarker into molecular probe: melanin nanoparticle as a naturally active platform for multimodality imaging. J Am Chem Soc 2014; 136:15185-15194. PMID: 25292385, PMCID: PMC4227813, DOI: 10.1021/ja505412p
62. Longo D L, Stefania R, Aime S, Oraevsky A. Melanin-based contrast agents for biomedical optoacoustic imaging and theranostic applications. Int J Molec Sci 2017; 18:1719. PMID: 28783106, PMCID: PMC5578109, DOI: 10.3390/ijms18081719
63. Ito S, Inoue S, Yamamoto Y, Fujita K. Synthesis and antitumor activity of cysteinyl-3,4-dihydroxyphenylalanines and related compounds. J Med Chem 1981; 24:673-677. PMID: 6788955, no PMCID, no DOI
64. Chen C, Zhu Y F, Wilcoxen K. An improved synthesis of selectivity protected L-dopa derivatives from L-tyrosine. J Org Chem 2000; 65:2574-2576. No PMID, no PMCID, DOI: 10.1021/jo9913661
65. He G, Lu C, Zhao Y, Nack W A, Chen G. Improved protocol for indoline synthesis via palladium-catalyzed intramolecular C(sp2)-H amination. Org Lett 2012; 14:2944-2947. PMID: 22670815, no PMCID, no DOI.
66. Fernandez-Cuervo G, Tucker K A, Malm S W, Jones K M, Pagel M D. Diamagnetic imaging agents with a modular chemical design for quantitative detection of 3-galactosidase and β-glucuronidase activities with catalyCEST MM. Bioconjug Chem 2016, 27:2549-2557. PMID: 27657647, no PMCID, DOI: 10.1021/acs.bioconjchem.6b00482.
67. Hingorani D V, Montano L A, Randtke E A, Lee Y S, Cardenas-Rodriguez J, Pagel M D. A single diamagnetic catalyCEST Mill contrast agent that detects cathepsin B enzyme activity by using a ratio of two CEST signals.

Contrast Media Molec Imaging 2016; 11:130-138. PMID: 26633584, PMCID: PMC4882611, DOI: 10.1002/cmmi.1672
68. Yoo B, Pagel M D. Peptidyl molecular imaging contrast agents using a new solid phase peptide synthesis approach. Bioconj Chem 2007; 18:903-911. PMID 17330953, PMCID: PMC2584118, DOI: 10.1021/bc060250q
69. Yoo B, Pagel M D. A facile synthesis of α-amino-DOTA as a versatile molecular imaging probe. Tet Lett 2006; 47:7327-7330. No PMID, no PMCID, DOI: 10.1016/j.tetlet.2006.08.019
70. Liu G, Li Y, Pagel M D. Design and characterization of new irreversible responsive PARACEST MRI contrast agent that detects nitric oxide. Magn Reson Med 2007; 58:1249-1256. PMID 18046705, no PMCID, DOI: 10.1002/mrm.21428
71. Yoo B, Sheth V, Pagel M D. An amine-derivatized, DOTA-loaded polymeric support for Fmoc solid phase peptide synthesis. Tet Lett 2009; 50:4459-4462. PMID 20161272, PMCID: PMC2702766, DOI: 10.1016/j.tetlet.2009.05.061
72. Ali M M, Yoo B, Pagel M D. Tracking the relative in vivo pharmacokinetics of nanoparticles with PARACEST MM. Molec Pharmaceutics 2009; 6:1409-1416. PMID 19298054, PMCID: PMC4216567, DOI: 10.1021/mp900040u
73. Hingorani D V, Randtke E A, Pagel M D. A catalyCEST MM contrast agent that detects the enzyme-catalyzed creation of a covalent bond. J Am Chem Soc 2013; 135:6396-6398. PMID 23601132, PMCID: PMC3667154, DOI: 10.1021/j a400254e.
74. Yoo B, Sheth V R, Howison C M, Douglas M J K, Pineda C T, Maine E A, Baker A F, Pagel M D. Detection of in vivo enzyme activity with catalyCEST MM. Mag Reson Med 2014; 71:1221-1230. PMID 23640714, PMCID: PMC3742626, DOI: 10.1002/mrm.24763.
75. Fernandez-Cuervo G, Sinharay S, Pagel M D. A catalyCEST MRI contrast agent that can simultaneously detect two enzyme activities. ChemBioChem, 2016; 17(5):383-387. PMID: 26693680, PMCID: PMC4814164, DOI: 10.1002/cbic.201500586.
76. Sinharay S, Fernandez-Cuervo G, Acfalle J P, Pagel M D. Detection of sulfatase enzyme activity with a catalyCEST Mill contrast agent. Chem Euro J 2016; 22:6491-6495. PMID: 26956002, PMCID: PMC4877021, DOI: 10.1002/chem.201600685
77. Daryaei I, Randtke E A, Pagel M D. A biomarker-responsive T2ex MRI contrast agent. Magn Reson Med 2017; 77:1665-1670. PMID: 27090199, PMCID: PMC5071101, DOI: 10.1002/mrm.26250
78. Sinharay S, Randtke E A, Jones K M, Howison C M, Chambers S K, Kobayashi H, Pagel M D. Noninvasive detection of enzyme activity in tumor models of human ovarian cancer using catalyCEST MM. Magn Reson Med 2017; 77:2005-2014. PMID: 27221386, PMCID: PMC5123981, DOI: 10.1002/mrm.26278
79. Daryaei I, Jones K M, Pagel M D. Detection of DT-diaphorase enzyme with a paraCEST MRI contrast agent. Chem Euro J 2017; 23:6514-6517. PMID: 28370655, no PMCID, DOI: 10.1002/chem.201700721.
80. Sinharay S, Howison C M, Baker A F, Pagel M D. Detecting in vivo urokinase Plasminogen Activator activity with a catalyCEST MM contrast agent. NMR Biomed 2017, 30(7):e3721. PMID: 28370884, PMCID: PMC5704996, DOI: 10.1002/nbm.3721
81. Sinharay S, Randtke E A, Howison C M, Ignatenko N A, Pagel M D. Detection of enzyme activity and inhibition during studies in solution, in vitro and in vivo with catalyCEST MM. Molec Imaging Biol 2018; 20:240-248. PMID: 28726131, no PMCID, DOI: 10.1007/s11307-017-1092-8
82. Shamis M, Lode H N, Shabat D. Bioactivation of self-immolative dendritic prodrugs by catalytic antibody 38C2. J Am Chem Soc 2004; 126:1726-1731. PMID: 14871103, no PMCID, DOI: 10.1021/ja039052p
83. Hupple C W, Morscher S, Burton N C, Pagel M D., McNally L R, Cardenas-Rodriguez J. A light-fluence-independent method for the quantitative analysis of dynamic contrast-enhanced multispectral optoacoustic tomography (DCE MSOT). Photoacoustics 2018; 10:54-64. No PMID, no PMCID, DOI: 10.1016/j.pacs.2018.04.003
84. Yoo B, Pagel M D. A PARACEST MM contrast agent to detect enzyme activity. J Am Chem Soc 2006; 128:14032-14033. PMID: 17061878, no PMCID, DOI: 10.1021/ja063874f
85. Yoo B, Raam M, Rosenblum R, Pagel M D. Enzyme-responsive PARACEST MRI contrast agents: A new biomedical imaging approach for studies of the proteasome. Contrast Media Molec Imaging 2007; 2:189-198. PMID: 17712869, no PMCID, DOI: 10.1002/cmmi.145
86. Jones K M, Pagel M D., Cárdenas-Rodríguez J. Linearization improves the repeatability of quantitative dynamic contrast enhanced MRI. Magn Reson Imaging, 2018; 47:16-24. PMID: 29155024, PMCID: PMC5828901, DOI: 10.1016/j.mri.2017.11.002
87. Flurkey W H, Inlow J K. Use of mushroom tyrosinase to introduce Michaelis-Menten enzyme kinetics to biochemistry students. Biochem Mol Biol Educ 2017; 45:270-276. PMID: 28509370, no PMCID, DOI: 10.1002/bmb.21029.
88. Selvarajan E, Mohanasrinivasan V. Kinetic studies on exploring lactose hydrolysis potential of □ galctosidase extracted from *Lactobacillus plantarum* HF571129. J Food Sci Technol 2015; 52:6206-6217. PMID: 26396367, PMCID: PMC4573140, DOI: 10.1007/s13197-015-1729-z
89. Farnleitner A H, Hocke L, Beiwl C, Kavka G G, Mach R L. Hydrolysis of 4-methylumbelliferyl-beta-D-glucuronidase in differing sample fractions of river waters and its implication for the detection of fecal pollution. Water Res 2002; 36:975-981. PMID: 11848369, no PMCID, no DOI.
90. De Bruyne C K, Yde M. Binding of alkyl I-thio-□-D-galactopyranosides to –□-D-galactosidase from *E. coli*. Carbohydrate Res 1977; 56:153-164. PMID: 18283, no PMCID, no DOI.
91. Wallace B D, Wang H, Lane K T, Scott J E, ORans J, Koo J S, Venkatesh M, Jobin C, yeh LA, Mani S, Redinbo M R. Alleviating cancer drug toxicity by inhibiting a bacterial enzyme. Science 2010; 330:831-835. PMID 21051639; PMCID: PMC3110694, DOI: 10.1126/science.1191175
92. Randtke E A, Chen L Q, Corrales L R, Pagel M D. The Hanes-Woolf Linear QUESP method improves the measurements of fast chemical exchange rates with CEST MRI Magn Reson Med 2014; 71:1603-1612. PMID 23780911, PMCID: PMC3784632, DOI: 10.1002/mrm.24792.
93. Fernandez-Cuervo Velasco G. Design, synthesis and application of catalyCEST Mill agents for enzyme detection. PhD Thesis, University of Arizona, 2017. No PIMD, no PMCID, no DOI.

94. Kobes J E, Daryaei I, Howison C M, Bontrager J G, Siriani R S, Meuillet E M, Pagel M D. Improved treatment of pancreatic cancer with drug delivery nanoparticles loaded with a novel AKT/PDK1 inhibitor. Pancreas 2016; 45:1158-1166. PMID: 26918875, PMCID: PMC4983222, DOI: 10.1097/MPA.0000000000000607.

95. Chen L Q, Randtke E A, Jones K M, Moon B F, Howison C M, Pagel M D. Evaluations of tumor acidosis within in vivo tumor models using parametric maps generated with acidoCEST MRI. Mol Imaging Biol 2015; 17:488-496. PMID: 25622809, PMCID: PMC4880367, DOI: 10.1007/s11307-014-0816-2.

96. Miller L R, Marks C, Becker J B, Hurn P D, Chen W J, Woodruff T, McCarthy M M Sohrabji F, Schiebinger L, Wetherington C L, Makris S, Arnold A P, Einstein G, Miller V M, Sandberg K, Maier S, Cornelison T L, Clayton J A. Considering sex as a biological variable in preclinical research. FASEB J, 2017; 31:29-34. PMID: 27682203, no PMCID, DOI: 10.1096/fj.201600781R All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A composition, comprising:

a compound, comprising:

a melanin precursor that spontaneously synthesizes a melanin when in free form in vivo, and a peptide directly covalently bonded to or indirectly linked to the melanin precursor, wherein the direct covalent bond or the indirect link of the peptide to the melanin precursor blocks spontaneous synthesis of the melanin in vivo in the absence of protease activity.

2. The composition of claim 1, wherein the melanin precursor is selected from the group consisting of leucodopachrome, decarboxylated leucodopachrome, and cysteinyldopa.

3. The composition of claim 1, wherein the indirect link comprises a p-hydroxybenzyl moiety.

4. The composition of claim 2, wherein the compound is selected from the group consisting of Agent 1, Agent 2, Agent 3, and Agent 6:

Agent 1

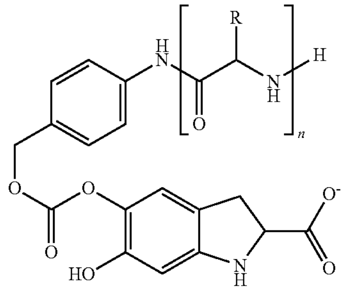

-continued

Agent 2

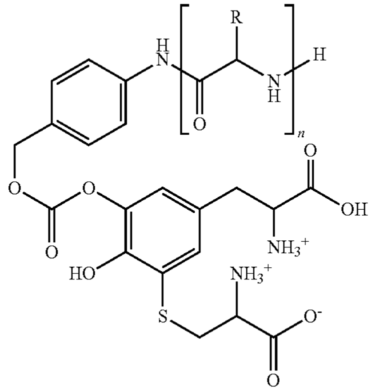

Agent 3

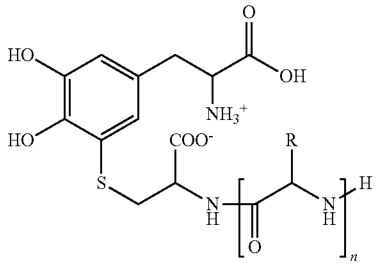

Agent 6

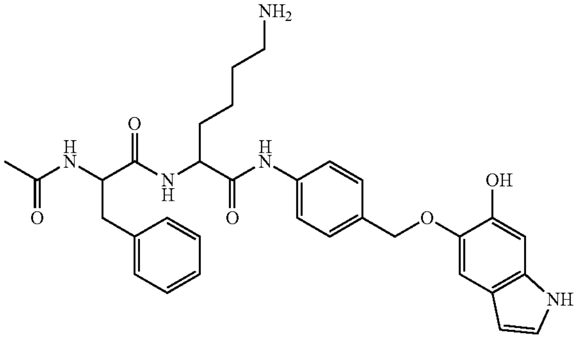

wherein n is greater than or equal to 1 and each R is any organic moiety.

5. The composition of claim 1, further comprising:

a pharmaceutically-acceptable carrier.

6. A method, comprising:

administering, to a patient suffering from a tumor, a composition comprising a compound comprising a melanin precursor that spontaneously synthesizes a melanin when in free form in vivo, and a peptide directly covalently bonded to or indirectly linked to the melanin precursor, wherein the direct covalent bond or the indirect link of the peptide to the melanin precursor blocks spontaneous synthesis of the melanin in vivo in the absence of protease activity; and surgically resecting the tumor, wherein the surgical resection is guided at least in part by contrast imparted by the melanin, wherein the melanin is spontaneously synthesized in the tumor after administering the composition.

7. The method of claim 6, wherein the tumor is a solid tumor comprising cells that express high levels of protease.

8. The method of claim 7, wherein the tumor is of a cancer selected from the group consisting of breast cancer, head-and-neck cancer, pancreatic cancer, ovarian cancer, and thyroid cancer.

9. The method of claim 6, wherein the melanin precursor in the compound in the administered composition is selected from the group consisting of leucodopachrome, decarboxylated leucodopachrome, and cysteinyldopa.

10. The method of claim 6, wherein the indirect link between the melanin precursor and the peptide in the compound in the administered composition comprises a p-hydroxybenzyl moiety.

11. The method of claim 10, wherein the compound in the administered composition is selected from the group consisting of Agent 1, Agent 2, Agent 3, and Agent 6:

Agent 1

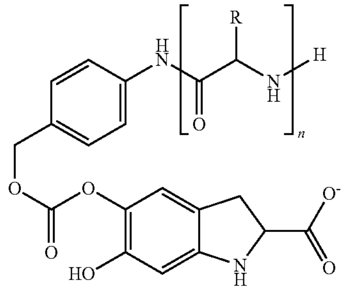

Agent 2

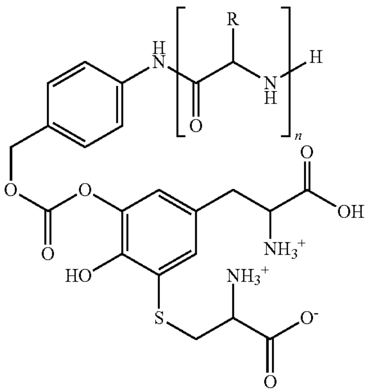

Agent 3

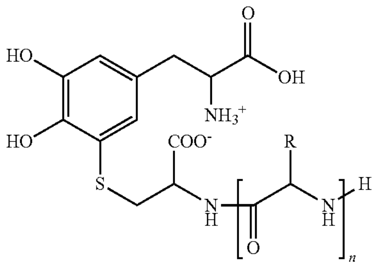

Agent 6

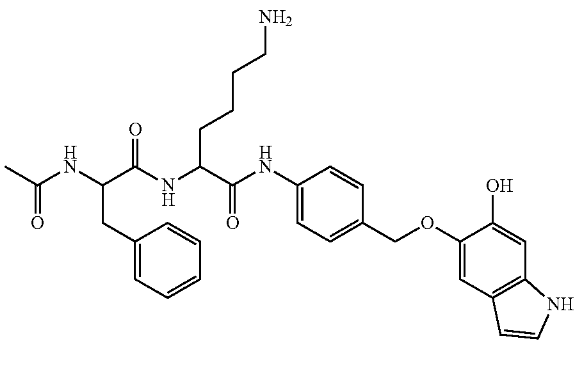

wherein n is greater than or equal to 1 and each R may be any organic moiety.

12. The method of claim 6, further comprising:

administering, to the patient, a cancer treatment modality other than surgical resection.

13. The method of claim 12, wherein the cancer treatment modality other than surgical resection is selected from the group consisting of radiation therapy, chemotherapy, immunotherapy, checkpoint inhibitor therapy, oncolytic virus therapy, peptide therapy, thermal therapy, and two or more thereof.

14. A method, comprising:

administering, to a patient suffering from a tumor, a composition comprising a compound comprising a melanin precursor that spontaneously synthesizes a melanin when in free form in vivo, and a peptide directly covalently bonded to or indirectly linked to the melanin precursor, wherein the direct covalent bond or the indirect link of the peptide to the melanin precursor blocks spontaneous synthesis of the melanin in vivo in the absence of protease activity; and thermally ablating the tumor, wherein the thermal ablating targets cells containing the melanin, wherein the melanin is spontaneously synthesized in the tumor after administering the composition.

15. The method of claim 14, wherein the tumor is a solid tumor comprising cells that express high levels of protease.

16. The method of claim 14, wherein the melanin precursor in the compound in the administered composition is selected from the group consisting of leucodopachrome, decarboxylated leucodopachrome, and cysteinyldopa.

17. The method of claim 14, wherein the indirect link between the melanin precursor and the peptide in the compound in the administered composition comprises a p-hydroxybenzyl moiety.

18. The method of claim 17, wherein the compound in the administered composition is selected from the group consisting of Agent 1, Agent 2, Agent 3, and Agent 6:

Agent 1

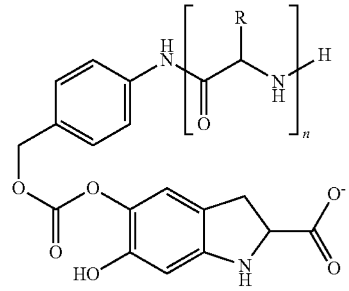

-continued

Agent 2

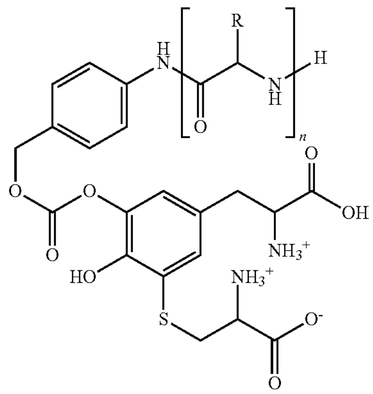

Agent 3

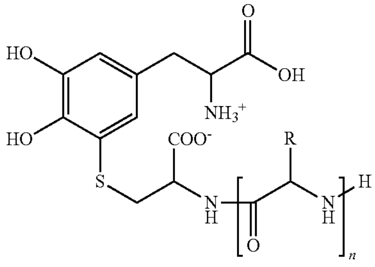

-continued

Agent 6

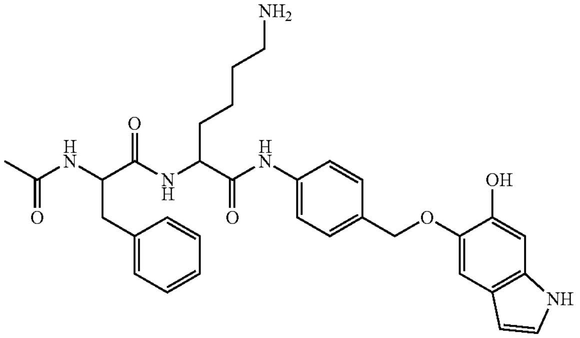

wherein n is greater than or equal to 1 and each R may be any organic moiety.

19. The method of claim 14, further comprising: administering, to the patient, a cancer treatment modality other than thermal ablation.

20. The method of claim 19, wherein the cancer treatment modality other than thermal ablation is selected from the group consisting of radiation therapy, chemotherapy, immunotherapy, checkpoint inhibitor therapy, oncolytic virus therapy, peptide therapy, cryotherapy, and two or more thereof.

* * * * *